US008889884B1

(12) United States Patent
Hermanson et al.

(10) Patent No.: US 8,889,884 B1
(45) Date of Patent: Nov. 18, 2014

(54) PHOSPHINE DERIVATIVES OF FLUORESCENT COMPOUNDS

(75) Inventors: Greg Hermanson, Loves Park, IL (US); Peter T. Czerney, Weimar (DE); Surbhi Desai, Rockford, IL (US); Suk J. Hong, Roscoe, IL (US); Matthias S. Wenzel, Jena (DE); Boguslawa Dworecki, Rockford, IL (US); Frank G. Lehmann, Jena (DE)

(73) Assignees: Pierce Biotechnology, Inc., Rockford, IL (US); Dyomics GmbH, Jena (DE)

( * ) Notice: Subject to any disclaimer, the term of this patent is extended or adjusted under 35 U.S.C. 154(b) by 0 days.

(21) Appl. No.: 13/546,483

(22) Filed: Jul. 11, 2012

Related U.S. Application Data

(60) Provisional application No. 61/507,742, filed on Jul. 14, 2011.

(51) Int. Cl.
*C07F 9/535* (2006.01)
(52) U.S. Cl.
CPC ............................. *C07F 9/535* (2013.01)
USPC .................................................. 548/414
(58) Field of Classification Search
CPC ............................................. C07F 9/535
USPC .................................................. 548/414
See application file for complete search history.

(56) References Cited

U.S. PATENT DOCUMENTS

| | | | |
|---|---|---|---|
| 1,524,791 A | 2/1925 | Konig |
| 4,839,265 A | 6/1989 | Ohno et al. |
| 4,981,977 A | 1/1991 | Southwick et al. |
| 5,268,486 A | 12/1993 | Waggoner et al. |
| 5,486,616 A | 1/1996 | Waggoner et al. |
| 5,556,959 A | 9/1996 | Brush et al. |
| 5,569,587 A | 10/1996 | Waggoner |
| 5,569,766 A | 10/1996 | Waggoner et al. |
| 5,627,027 A | 5/1997 | Waggoner |
| 5,846,737 A | 12/1998 | Kang |
| 5,972,838 A | 10/1999 | Pearce et al. |
| 5,986,086 A | 11/1999 | Brush et al. |
| 6,048,982 A | 4/2000 | Waggoner |
| 6,083,485 A | 7/2000 | Licha et al. |
| 6,136,612 A | 10/2000 | Della Ciana et al. |
| 6,225,050 B1 | 5/2001 | Waggoner |
| 6,258,340 B1 | 7/2001 | Licha et al. |
| 6,342,326 B1 | 1/2002 | Milton |
| 6,534,041 B1 | 3/2003 | Licha et al. |
| 6,641,093 B2 | 11/2003 | Coudrais |
| 6,939,532 B2 | 9/2005 | Achilefu et al. |
| 6,974,873 B2 | 12/2005 | Leung et al. |
| 6,977,305 B2 | 12/2005 | Leung et al. |
| 7,172,907 B2 | 2/2007 | Chen et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |
| 8,431,111 B2 | 4/2013 | Nairne et al. |
| 2001/0055567 A1 | 12/2001 | Licha et al. |
| 2002/0064794 A1 | 5/2002 | Leung et al. |
| 2002/0077487 A1 | 6/2002 | Leung et al. |
| 2004/0241095 A1 | 12/2004 | Achilefu et al. |
| 2006/0004188 A1 | 1/2006 | Leung et al. |
| 2006/0099638 A1 | 5/2006 | Leung et al. |
| 2006/0199949 A1 | 9/2006 | Waggoner |
| 2007/0128659 A1 | 6/2007 | Czerney et al. |
| 2007/0178512 A1 | 8/2007 | Leung et al. |
| 2007/0203343 A1 | 8/2007 | West et al. |
| 2008/0233050 A1 | 9/2008 | Achilefu et al. |
| 2009/0035809 A1 | 2/2009 | Leung et al. |
| 2009/0305410 A1 | 12/2009 | Mao et al. |
| 2010/0040547 A1 | 2/2010 | Frangioni |
| 2010/0196282 A1 | 8/2010 | Nairne et al. |
| 2010/0215585 A1 | 8/2010 | Frangioni |
| 2010/0267937 A1 | 10/2010 | West et al. |
| 2010/0303732 A1 | 12/2010 | Bahner |
| 2011/0065876 A1 | 3/2011 | Okamoto et al. |
| 2011/0065896 A1 | 3/2011 | Licha et al. |
| 2011/0171678 A1 | 7/2011 | Leung et al. |
| 2011/0178397 A1 | 7/2011 | Bahner |
| 2012/0114563 A1 | 5/2012 | Carter et al. |
| 2014/0106349 A1 | 4/2014 | Mao et al. |

FOREIGN PATENT DOCUMENTS

| | | |
|---|---|---|
| AU | 2006200511 | 2/2006 |
| DE | 4445065 A1 | 6/1996 |
| DE | 19717904 A1 | 10/1998 |
| DE | 19926460 A1 | 12/1999 |
| DE | 10046215 A1 | 4/2002 |
| EP | 1 152 008 | 11/2001 |

(Continued)

OTHER PUBLICATIONS

International Search Report and Written Opinion PCT/US2013/028252, issued by the European Patent Office, and mailed Apr. 25, 2013 (12 pages).
Wilchek and Miron. Activation of Sepharose with N,N'-disuccinimidyl carbonate. Applied Biochemistry and Biotechnology, vol. 11, pp. 191-193 (1985).
United Kingdom Search and Examination Report GB1214580.1, dated Nov. 22, 2012, 4 pages.
Hermanson, Bioconjugate Techniques, 2nd Ed., London, Elsevier Inc. 2008, pp. 464-474; 690-697.
International Search Report of the World Intellectual Property Bureau for PCT/US2011/065975, dated Mar. 15, 2012.
Written Opinion of the World Intellectual Property Bureau for PCT/US2011/065975, dated Mar. 15, 2012.

(Continued)

Primary Examiner — Shawquia Young
(74) Attorney, Agent, or Firm — Thompson Hine LLP

(57) ABSTRACT

A phosphine derivative of DyLight dyes modified with ethylene glycol or (poly)ethylene glycol groups. In one embodiment, the compounds are useful in chemoselective ligation reactions.

20 Claims, 68 Drawing Sheets
(51 of 68 Drawing Sheet(s) Filed in Color)

(56) References Cited

FOREIGN PATENT DOCUMENTS

| | | |
|---|---|---|
| EP | 1181940 | 2/2002 |
| EP | 1322710 | 7/2003 |
| EP | 1770129 | 4/2007 |
| EP | 1792949 | 6/2007 |
| EP | 1801165 | 6/2007 |
| EP | 2325263 | 7/2010 |
| GB | 434875 | 9/1935 |
| JP | 03217837 | 9/1991 |
| JP | Hei 5-313304 | 11/1993 |
| WO | 96/17628 | 6/1996 |
| WO | 98/48838 | 11/1998 |
| WO | 00/75237 | 12/2000 |
| WO | 02/26891 | 4/2002 |
| WO | 02/32466 A1 | 4/2002 |
| WO | 2004/065491 | 8/2004 |
| WO | 2005/044923 | 5/2005 |
| WO | 2005/103162 | 11/2005 |
| WO | 2006/020947 | 2/2006 |
| WO | 2009/016180 | 2/2009 |
| WO | 2009/016181 | 2/2009 |
| WO | 2009/078970 | 6/2009 |
| WO | 2009/078970 A1 | 6/2009 |
| WO | 2010/091126 | 8/2010 |
| WO | 2010/106169 | 9/2010 |
| WO | 2012/088007 A1 | 6/2012 |
| WO | 2012/129128 A1 | 9/2012 |

OTHER PUBLICATIONS

Search Report issued by the German Patent Office regarding App #10 2006 029 454.8 issued Oct. 10, 2006 (with English language summary).

Search Report issued by the German Patent Office regarding App #10 2006 057 345.5 issued May 21, 2007 (with English language summary).

Alvarez-Maubecin, V. et al. Functional Coupling Between Neurons and Glia. The Journal of Neuroscience. Jun. 1, 2000, 20(11):4091-4098.

Bharaj, B.S. et al. Rapid sequencing of the *p53* gene with a new automated DNA sequencer. Clinical Chemistry. 44:7 1397-1403 1998.

Biotium. Product brochure titled CF™ Dyes the next-generation dyes for protein labeling. Apr. 6, 2009.

Burns, M.A. et al. An Integrated Nanoliter DNA Analysis Device. Science. vol. 282, pp. 484-487, Oct. 16, 1998.

DeRisi, J.L. et al. Exploring the Metabolic and Genetic Control of Gene Expression on a Genomic Scale. Science. vol. 278, ppl. 680-686, Oct. 24, 1997.

Fradelizi, J. et al. Quantitative Measurement of Proteins by Western Blotting with Cy5™-Coupled Secondary Antibodies. BioTechniques. 26:484-494 Mar. 1999.

Gragg, J. L. Synthesis of Near-Infrared Heptamethine Cyanine Dyes. Chemistry Theses. Paper 28 (2010). http://digitalarchive.gsu.edu/chemistry_theses/28.

MacBeath, G. and S.L. Schreiber. Printing Proteins as Microarrays for High-Throughput Function Determination. Science. vol. 289, pp. 1760-1763, Sep. 8, 2000.

Manders, E.M.M. et al. Direct Imaging of DNA in Living Cells Reveals the Dynamics of Chromosome Formation. The Journal of Cell Biology. vol. 144, No. 5, Mar. 8, 1999 813-821.

Mank, A.J.G. et al., Visible Diode Laser-Induced Fluorescence Detection in Liquid Chromatography after Precolumn Derivatization of Amines. Anal. Chem. vol. 67, pp. 1742-1748, 1995.

Mujumdar, R.B. et al. Cyanine Dye Labeling Reagents: Sulfoindocyanine Succinimidyl Esters. Bioconjug Chem. vol. 4, No. 2, pp. 105-111, Mar./Apr. 1993.

Patonay, G., et al. Noncovalent Labeling of Biomolecules with Red and Near-Infrared Dyes. Molecules. 9, 40-49, 2004.

Pharmacia Biotech. Table of Contents p. 294 and p. 295 of the Pharmacia Biotech Catalogue. 1994.

Roman, B.L. et al. Non-Radioisotopic AFLP Method Using PCR Primers Fluorescently Labeled with Cy™5. BioTechniques. vol. 26, No. 2, pp. 236-238, Feb. 1999.

Schena, M. et al. Parallel human genome analysis: Microarray-based expression monitoring of 1000 genes. Proc. Natl. Acad. Sci. USA. vol. 93, pp. 10614-10619, Oct. 1996.

Shao, F. et al. Monofunctional Carbocyanine Dyes for Bio- and Bioorthogonal Conjugation. Bioconjugate Chemistry. 19(12): 2487-2491, Dec. 2008.

Voss, H. et al. Automated Cycle Sequencing with Taquenase™: Protocols for Internal Labeling, Dye Primer and "Doublex" Simultaneous Sequencing. BioTechniques. vol. 23, No. 2, pp. 312-318, Aug. 1997.

International Preliminary Report on Patentability, PCT/US/2011/065975, mailed Jul. 4, 2013 (8 pages).

Hermanson, Bioconjugate Techniques, 2nd Ed., London, Elsevier Inc. 2008, pp., 464-474; 690-697.

Strekowski (ed.), Heterocyclic Polymethine Dyes: Synthesis, Properties and Applications, (2008) Springer-Verlag, Berlin Heidelberg, pp. 1-241.

Licha et al. Synthesis and Characterization of Cyanine Dye-Poly(ethylene Glycol) Conjugates as Contrast Agents for In Vivo Fluorescence Imaging. SPIE 3196 (1998) 98-102.

Riefke et al. Tumor Detection with Cyanine Dye-Poly(ethylene Glycol) Conjugates as Contrast Agents for Near-Infrared Imaging. SPIE 3196 (1998) 103-110.

Before Imperial Stain

After Imperial Stain

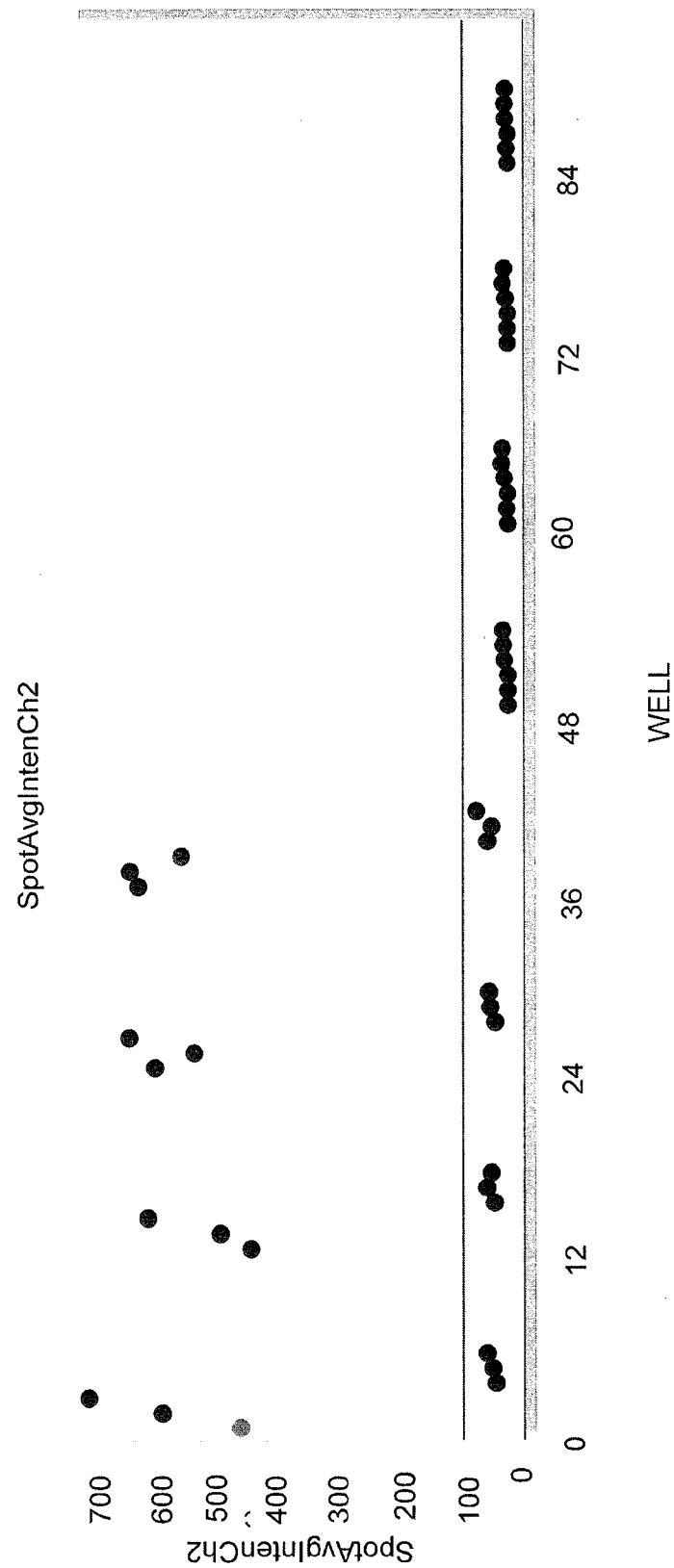

FIG. 40
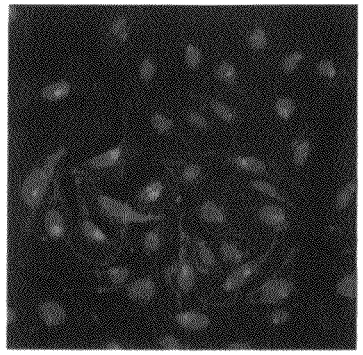
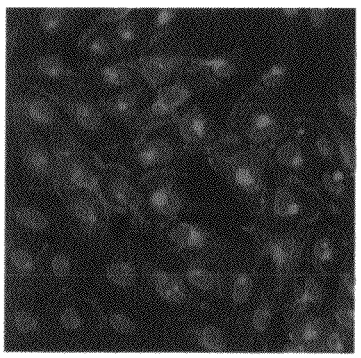
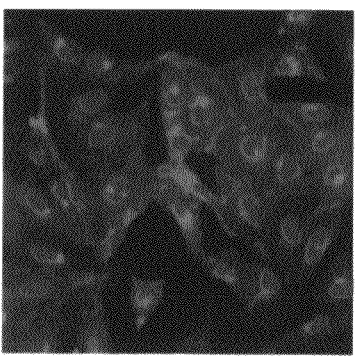
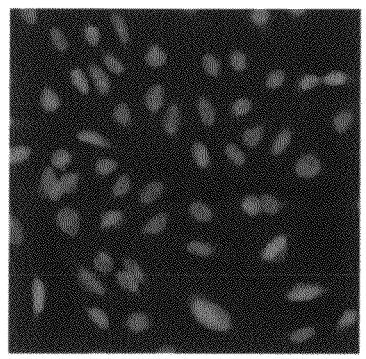
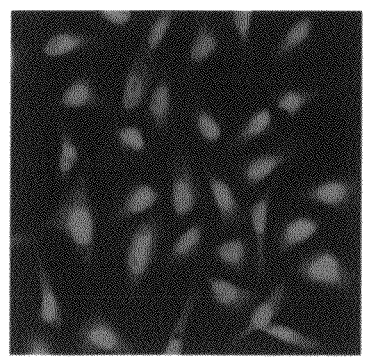

FIG. 44
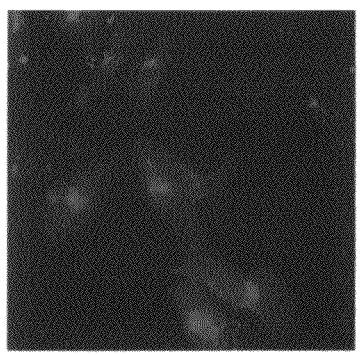
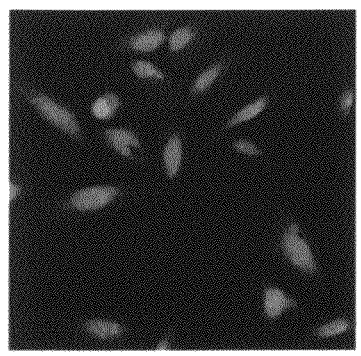
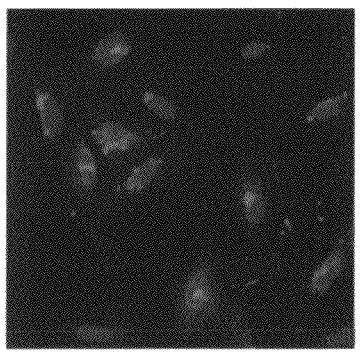
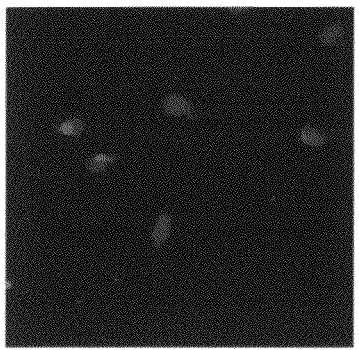
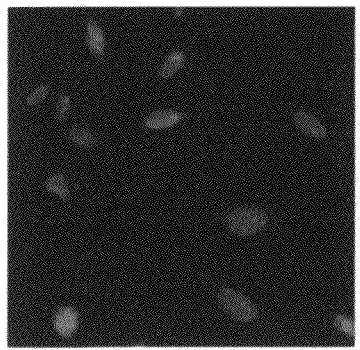

FIG. 45A

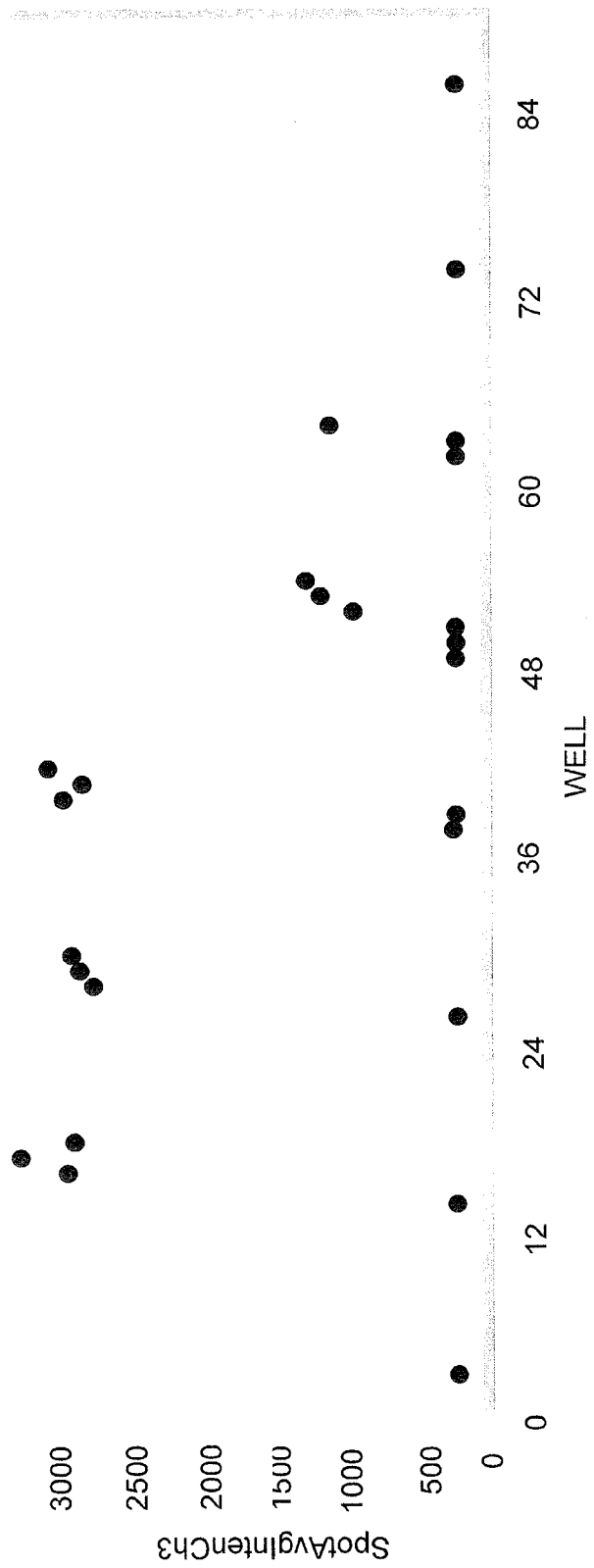

FIG. 58
A  B
1 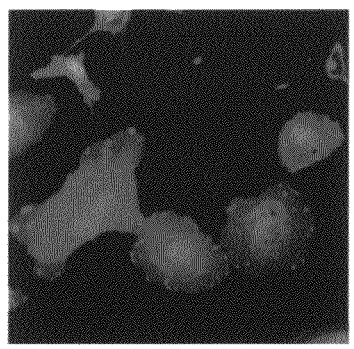 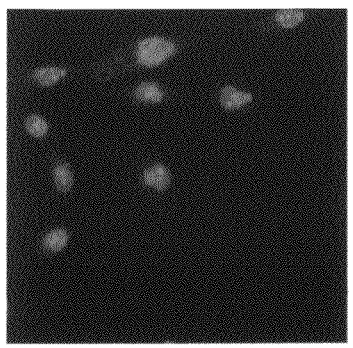
2 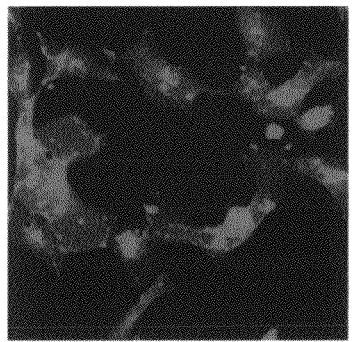 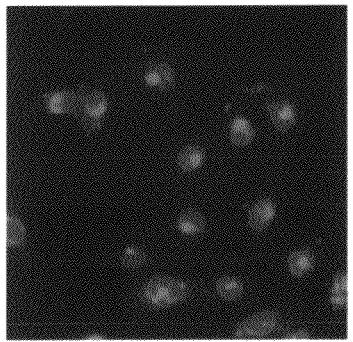
3 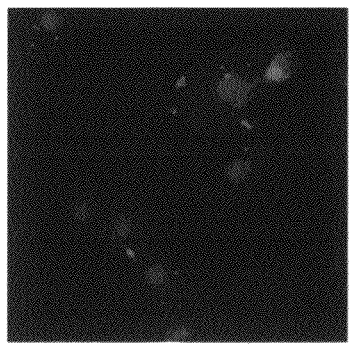 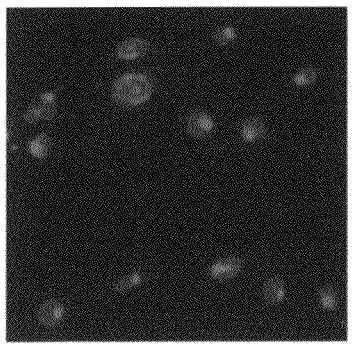

PHOSPHINE DERIVATIVES OF FLUORESCENT COMPOUNDS

This application claims priority to U.S. Provisional Application No. 61/507,742, filed Jul. 14, 2011, which is incorporated by reference herein in its entirety.

A phosphine derivative of DyLight dyes modified with ethylene glycol or (poly)ethylene glycol groups. Phosphine derivatives of DyLight 550, 650, and 755, which contain ethylene glycol or (poly)ethylene glycol, are disclosed. The phosphine derivatives are useful in chemoselective ligation reactions, also termed bioorthogonal reactions, e.g., with azido groups to form a covalent bond, with applications to "Click" chemistry producing reactions that are high yielding, wide in scope, creating only byproducts that can be removed without chromatography, are stereospecific, are simple to perform, and can be conducted in easily removable or benign solvents, as known to one skilled in the art.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their t-system. Compounds that have insufficient hydrophilicity undergo non-specific interactions with various surfaces, resulting in problems when attempting purify the corresponding conjugate, and an unsatisfactory signal to noise ratio.

Efforts are directed to reducing undesirable properties by introducing substituents that increase the hydrophilicity of the compounds. For example, sulfonic acid function substituents have been introduced into the cyanine chromophore. U.S. Pat. No. 6,083,485 (Licha) and U.S. application Ser. Nos. 09/968,401 and 09/989,853 (Molecular Probes) disclose cyanine compounds having one of the common methyl groups in the 3-position of the terminal indole heterocycle substituted by an ω-carboxyalkyl function, and in which the previously present (e.g. in Cy3 or Cy5) N-alkyl or N-ω-carboxyalkyl functions are replaced by N-ω-alkyl sulfonic acid functions. WO 05/044923 discloses cyanine compounds having the common methyl substituent in the 3-position of the terminal indole heterocycle substituted by a N-ω-alkyl sulfonic acid function. In these publications, cyanine compounds having more than two sulfonic acid function substituents exhibited higher solubility and correspondingly a lower tendency to dimer formation, in comparison to cyanine compounds (Cy3, Cy5) described in U.S. Pat. No. 5,627,027.

The disclosed cyanine compounds are useful as labels in optical, especially fluorescence optical, determination and detection methods. The compounds have high hydrophilicity, high molar absorbance, high photo-stability, and high storage stability. These compounds can be excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules such as proteins (e.g., antigens, antibodies, etc.), DNA and/or RNA segments, etc. with the corresponding complimentary species. Thus, among other embodiments, the compounds are useful to measure enzyme kinetics, receptor-ligand interactions, and nucleic acid hybridization kinetics in vitro and/or in vivo.

The compounds are useful for the pharmacological characterization of receptors and/or drugs. Applications include, but are not limited to, uses in medicine, pharmacy, biological sciences, materials sciences, environmental control, detection of organic and inorganic micro samples occurring in nature, etc.

The patent or application file contains at least one drawing executed in color. Copies of this patent or patent application publication with color drawing(s) will be provided by the Office upon request and payment of the necessary fee.

FIG. 1 schematically shows conjugation between an azide-modified molecule and a fluorophore.

FIG. 2 schematically shows another conjugation between an azide-modified molecule and a fluorophore.

FIG. 3 schematically shows another conjugation between a phosphine-activated compound and an azide-labeled molecule.

FIG. 29A shows Spot Average Intensity of images of FIG. 28.

FIG. 40 shows fluorescence images of cells labeled with various phosphine-containing compounds.

FIG. 44 shows fluorescence images of cells labeled with various phosphine-containing compounds.

FIG. 45A shows Spot Average Intensity of images of FIG. 44.

FIG. 49B shows Spot Average Intensity of images of FIG. 48.

FIG. 58 shows fluorescence images of cells labeled with various phosphine-containing compounds.

Figure 1:
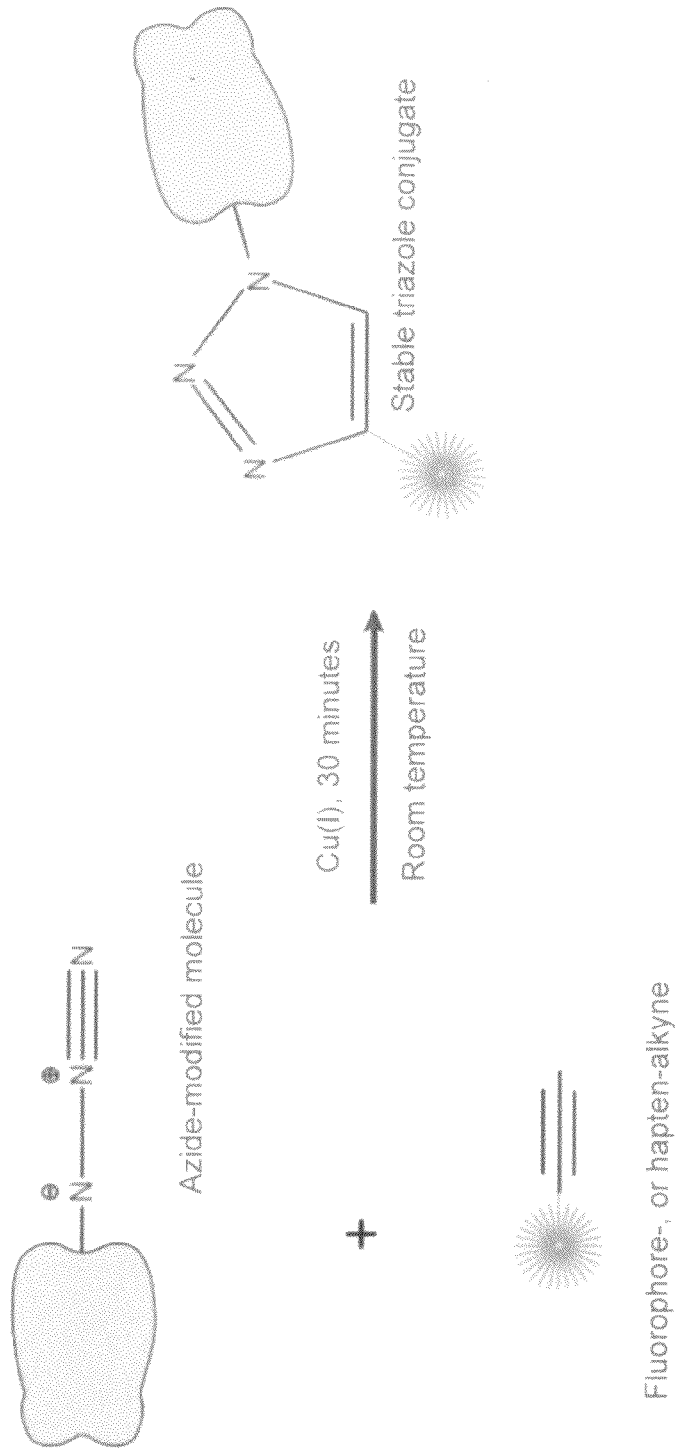

In one embodiment, the cyanine compounds have, in an N-position of one heterocycle, an ethylene glycol group, and the other heterocycle has, in a N-position, a function for conjugating the compound to a biomolecule.

In one embodiment, the cyanine compounds have, in an N-position of one heterocycle, an ethylene glycol polymer (i.e., poly(ethylene) glycol abbreviated as PEG), and the other heterocycle has, in a N-position, a function for conjugating the compound to a biomolecule.

In one embodiment, the compound is according to general formula I

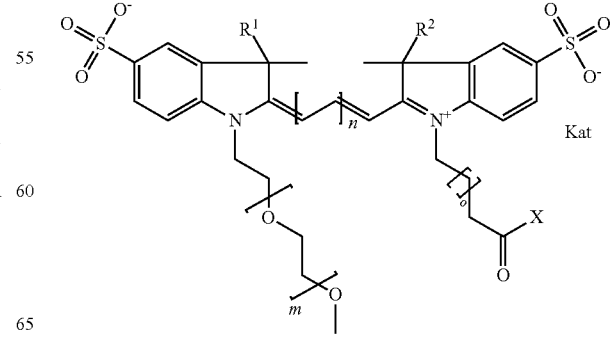

where each of $R^1$ and $R^2$ is the same or different and is independently selected from the group consisting of an aliphatic, heteroaliphatic, sulfoalkyl group, or heteroaliphatic with terminal $SO_3$; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. The benzocyanine form of the above compound is

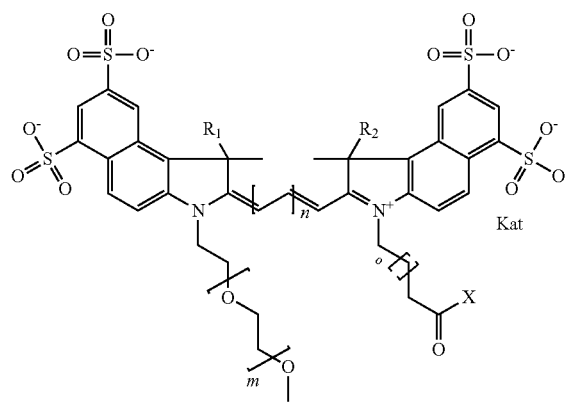

where the substituents are as described above.

In one embodiment, the compound is according to general formula I, where each of R1 is R2 is sulfoalkyl; X is —OH, —NHS, —O-TFP, or —NR-L-maleimide; m is 0; o is 3; and n is 1. In one embodiment, the compound is according to general formula I, where each of R1 is R2 is sulfoalkyl; X is —OH, —NHS, —O-TFP, or —NR-L-maleimide; m is 1; o is 3; and n is 1. In one embodiment, the compound is according to general formula I, where each of R1 is R2 is sulfoalkyl; X is —OH, —NHS, —O-TFP, or —NR-L-maleimide; m is 2; o is 3; and n is 1. In one embodiment, the compound is according to general formula I, where each of R1 is R2 is sulfoalkyl; X is —OH, —NHS, —O-TFP, or —NR-L-maleimide; m is 3; o is 3; and n is 1. In one embodiment, the compound is according to general formula I, where each of R1 is R2 is sulfoalkyl; X is —OH, —NHS, —O-TFP, or —NR-L-maleimide; m is 4; o is 3; and n is 1. In one embodiment, the compound is according to general formula I, where each of R1 is R2 is sulfoalkyl; X is —OH, —NHS, —O-TFP, or —NR-L-maleimide; m is 5; o is 3; and n is 1.

In one embodiment, the compound is according to general formula I, where each of R1 is R2 is sulfoalkyl; X is —OH, —NHS, —O-TFP, or —NR-L-maleimide; m is 0; o is 3; and n is 2. In one embodiment, the compound is according to general formula I, where each of R1 and R2 is sulfoalkyl; X is —OH, —NHS, —O-TFP, or —NR-L-maleimide; m is 1; o is 3; and n is 2. In one embodiment, the compound is according to general formula I, where each of R1 and R2 is sulfoalkyl; X is —OH, —NHS, —O-TFP, or —NR-L-maleimide; m is 2; o is 3; and n is 2. In one embodiment, the compound is according to general formula I, where each of R1 and R2 is sulfoalkyl; X is —OH, —NHS, —O-TFP, or —NR-L-maleimide; m is 3; o is 3; and n is 2. In one embodiment, the compound is according to general formula I, where each of R1 and R2 is sulfoalkyl; X is —OH, —NHS, —O-TFP, or —NR-L-maleimide; m is 4; o is 3; and n is 2. In one embodiment, the compound is according to general formula I, where each of R1 and R2 is sulfoalkyl; X is —OH, —NHS, —O-TFP, or —NR-L-maleimide; m is 5; o is 3; and n is 2.

In one embodiment, the compound is according to general formula I, where each of R1 and R2 is sulfoalkyl; X is —OH, —NHS, —O-TFP, or —NR-L-maleimide; m is 0; o is 3; and n is 3. In one embodiment, the compound is according to general formula I, where each of R1 and R2 is sulfoalkyl; X is —OH, —NHS, —O-TFP, or —NR-L-maleimide; m is 1; o is 3; and n is 3. In one embodiment, the compound is according to general formula I, where each of R1 and R2 is sulfoalkyl; X is —OH, —NHS, —O-TFP, or —NR-L-maleimide; m is 2; o is 3; and n is 3. In one embodiment, the compound is according to general formula I, where each of R1 and R2 is sulfoalkyl; X is —OH, —NHS, —O-TFP, or —NR-L-maleimide; m is 3; o is 3; and n is 3. In one embodiment, the compound is according to general formula I, where each of R1 and R2 is sulfoalkyl; X is —OH, —NHS, —O-TFP, or —NR-L-maleimide; m is 4; o is 3; and n is 3. In one embodiment, the compound is according to general formula I, where each of R1 and R2 is sulfoalkyl; X is —OH, —NHS, —O-TFP, or —NR-L-maleimide; m is 5; o is 3; and n is 3.

In one embodiment, the compound has general formula II

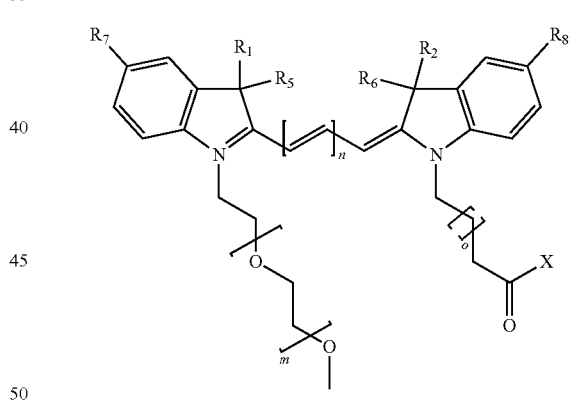

where each of $R^1$, $R^2$, $R^5$, and $R^6$ is the same or different and is independently selected from the group consisting of an aliphatic, heteroaliphatic, sulfoalkyl group, or heteroaliphatic with terminal $SO_3$; each of $R^7$ and $R^8$ is the same or different and is independently selected from either H, $SO_3$, sulfoalkyl, heteroaliphatic, or heteroaliphatic with terminal $SO_3$; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—CH2-I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. The benzocyanine form of the above compound is

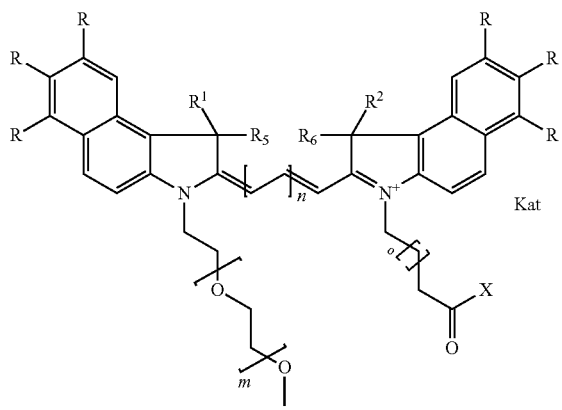

as described above, where each R is selected from the group described for R7 and R8.

In one embodiment, the compound has general formula III

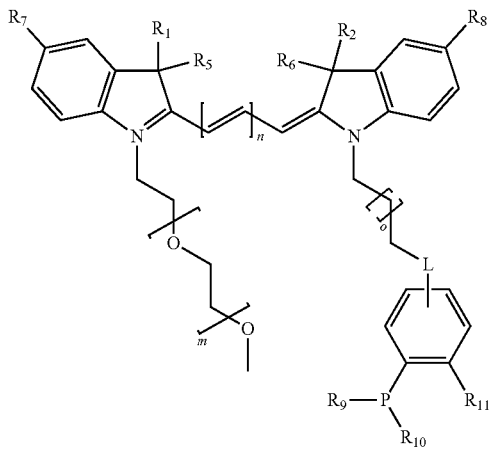

where each of $R^1$, $R^2$, $R^5$, and $R^6$ is the same or different and is independently selected from the group consisting of an aliphatic, heteroaliphatic, sulfoalkyl group, or heteroaliphatic with terminal $SO_3$; each of $R^7$ and $R^8$ is the same or different and is independently selected from either H, $SO_3$, sulfoalkyl, heteroaliphatic, or heteroaliphatic with terminal $SO_3$; each of R9 and R10 is the same or different and is independently selected from either aryl groups, substituted aryl groups, or cycloalkyl groups; R11 is an electrophilic group selected from the group consisting of a carboxylic acid, an alkyl ester, an aryl ester, a substituted aryl ester, an aldehyde, and amide, an aryl amide, an alkyl halide, a thioester, a sulfonyl ester, and alkyl ketone, an aryl ketone, a substituted aryl ketone, a halosulfonyl, a nitrile, and a nitro; L is a linking group that forms a covalent bond between the dye and the phosphine; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. The benzocyanine form of the above compound is

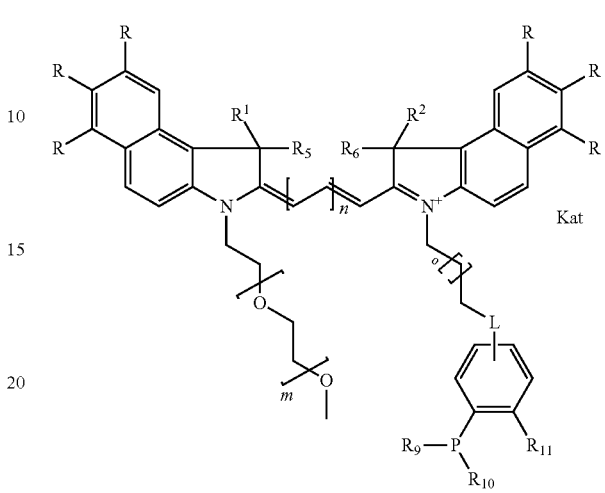

as described above, where each R is selected from the group described for R7 and R8.

In one embodiment, the compound is according to general formula III, where each of R1 and R2 is sulfoalkyl; each of R5 and R6 is methyl; each of R7 and R8 is $SO_3$; m is 0; o is 3; and n is 1. In one embodiment, the compound is according to general formula III, where each of R1 and R2 is sulfoalkyl; each of R5 and R6 is methyl; each of R7 and R8 is $SO_3$; m is 1; o is 3; and n is 1. In one embodiment, the compound is according to general formula III, where each of R1 and R2 is sulfoalkyl; each of R5 and R6 is methyl; each of R7 and R8 is $SO_3$; m is 2; o is 3; and n is 1. In one embodiment, the compound is according to general formula III, where each of R1 and R2 is sulfoalkyl; each of R5 and R6 is methyl; each of R7 and R8 is $SO_3$; m is 3; o is 3; and n is 1. In one embodiment, the compound is according to general formula III, where each of R1 and R2 is sulfoalkyl; each of R5 and R6 is methyl; each of R7 and R8 is $SO_3$; m is 4; o is 3; and n is 1. In one embodiment, the compound is according to general formula III, where each of R1 and R2 is sulfoalkyl; each of R5 and R6 is methyl; each of R7 and R8 is $SO_3$; m is 5; o is 3; and n is 1.

In one embodiment, the compound is according to general formula III, where each of R1 and R2 is sulfoalkyl; each of R5 and R6 is methyl; each of R7 and R8 is $SO_3$; m is 0; o is 3; and n is 2. In one embodiment, the compound is according to general formula III, where each of R1 and R2 is sulfoalkyl; each of R5 and R6 is methyl; each of R7 and R8 is $SO_3$; m is 1; o is 3; and n is 2. In one embodiment, the compound is according to general formula III, where each of R1 and R2 is sulfoalkyl; each of R5 and R6 is methyl; each of R7 and R8 is $SO_3$; m is 2; o is 3; and n is 2. In one embodiment, the compound is according to general formula III, where each of R1 and R2 is sulfoalkyl; each of R5 and R6 is methyl; each of R7 and R8 is $SO_3$; m is 3; o is 3; and n is 2. In one embodiment, the compound is according to general formula III, where each of R1 and R2 is sulfoalkyl; each of R5 and R6 is methyl; each of R7 and R8 is $SO_3$; m is 4; o is 3; and n is 2. In one embodiment, the compound is according to general formula III, where each of R1 and R2 is sulfoalkyl; each of R5 and R6 is methyl; each of R7 and R8 is $SO_3$; m is 5; o is 3; and n is 2.

In one embodiment, the compound is according to general formula III, where each of R1 and R2 is sulfoalkyl; each of R5 and R6 is methyl; each of R7 and R8 is SO₃; m is 0; o is 3; and n is 3. In one embodiment, the compound is according to general formula III, where each of R1 and R2 is sulfoalkyl; each of R5 and R6 is methyl; each of R7 and R8 is SO₃; m is 1; o is 3; and n is 3. In one embodiment, the compound is according to general formula III, where each of R1 and R2 is sulfoalkyl; each of R5 and R6 is methyl; each of R7 and R8 is SO₃; m is 2; o is 3; and n is 3. In one embodiment, the compound is according to general formula III, where each of R1 and R2 is sulfoalkyl; each of R5 and R6 is methyl; each of R7 and R8 is SO₃; m is 3; o is 3; and n is 3. In one embodiment, the compound is according to general formula III, where each of R1 and R2 is sulfoalkyl; each of R5 and R6 is methyl; each of R7 and R8 is SO₃; m is 4; o is 3; and n is 3. In one embodiment, the compound is according to general formula III, where each of R1 and R2 is sulfoalkyl; each of R5 and R6 is methyl; each of R7 and R8 is SO₃; m is 5; o is 3; and n is 3.

In one embodiment, the compound is according to general formula III, where each of R1 and R2 is sulfoalkyl; each of R5 and R6 is methyl; each of R7 and R8 is SO₃; m is 0; o is 3; L is —CONH—CH₂—CH₂—NHCO—; each of R9 and R10 is phenyl; R11 is COOCH₃; and n is 1. In one embodiment, the compound is according to general formula III, where each of R1 and R2 is sulfoalkyl; each of R5 and R6 is methyl; each of R7 and R8 is SO₃; m is 1; o is 3; L is —CONH—CH₂—CH₂—NHCO—; each of R9 and R10 is phenyl; R11 is COOCH₃; and n is 1. In one embodiment, the compound is according to general formula III, where each of R1 and R2 is sulfoalkyl; each of R5 and R6 is methyl; each of R7 and R8 is SO₃; m is 2; o is 3; L is —CONH—CH₂—CH₂—NHCO—; each of R9 and R10 is phenyl; R11 is COOCH₃; and n is 1. In one embodiment, the compound is according to general formula III, where each of R1 and R2 is sulfoalkyl; each of R5 and R6 is methyl; each of R7 and R8 is SO₃; m is 3; o is 3; L is —CONH—CH₂—CH₂—NHCO—; each of R9 and R10 is phenyl; R11 is COOCH₃; and n is 1. In one embodiment, the compound is according to general formula III, where each of R1 and R2 is sulfoalkyl; each of R5 and R6 is methyl; each of R7 and R8 is SO₃; m is 4; o is 3; L is —CONH—CH₂—CH₂—NHCO—; each of R9 and R10 is phenyl; R11 is COOCH₃; and n is 1. In one embodiment, the compound is according to general formula III, where each of R1 and R2 is sulfoalkyl; each of R5 and R6 is methyl; each of R7 and R8 is SO₃; m is 5; o is 3; L is —CONH—CH₂—CH₂—NHCO—; each of R9 and R10 is phenyl; R11 is COOCH₃; and n is 1.

In one embodiment, the compound is according to general formula III, where each of R1 and R2 is sulfoalkyl; each of R5 and R6 is methyl; each of R7 and R8 is SO₃; m is 0; o is 3; L is —CONH—CH₂—CH₂—NHCO—; each of R9 and R10 is phenyl; R11 is COOCH₃; and n is 2. In one embodiment, the compound is according to general formula III, where each of R1 and R2 is sulfoalkyl; each of R5 and R6 is methyl; each of R7 and R8 is SO₃; m is 1; o is 3; L is —CONH—CH₂—CH₂—NHCO—; each of R9 and R10 is phenyl; R11 is COOCH₃; and n is 2. In one embodiment, the compound is according to general formula III, where each of R1 and R2 is sulfoalkyl; each of R5 and R6 is methyl; each of R7 and R8 is SO₃; m is 2; o is 3; L is —CONH—CH₂—CH₂—NHCO—; each of R9 and R10 is phenyl; R11 is COOCH₃; and n is 2. In one embodiment, the compound is according to general formula III, where each of R1 and R2 is sulfoalkyl; each of R5 and R6 is methyl; each of R7 and R8 is SO₃; m is 3; o is 3; L is —CONH—CH₂—CH₂—NHCO—; each of R9 and R10 is phenyl; R11 is COOCH₃; and n is 2. In one embodiment, the compound is according to general formula III, where each of R1 and R2 is sulfoalkyl; each of R5 and R6 is methyl; each of R7 and R8 is SO₃; m is 4; o is 3; L is —CONH—CH₂—CH₂—NHCO—; each of R9 and R10 is phenyl; R11 is COOCH₃; and n is 2. In one embodiment, the compound is according to general formula III, where each of R1 and R2 is sulfoalkyl; each of R5 and R6 is methyl; each of R7 and R8 is SO₃; m is 5; o is 3; L is —CONH—CH₂—CH₂—NHCO—; each of R9 and R10 is phenyl; R11 is COOCH₃; and n is 2.

In one embodiment, the compound is according to general formula III, where each of R1 and R2 is sulfoalkyl; each of R5 and R6 is methyl; each of R7 and R8 is SO₃; m is 0; o is 3; L is —CONH—CH₂—CH₂—NHCO—; each of R9 and R10 is phenyl; R11 is COOCH₃; and n is 3. In one embodiment, the compound is according to general formula III, where each of R1 and R2 is sulfoalkyl; each of R5 and R6 is methyl; each of R7 and R8 is SO₃; m is 1; o is 3; L is —CONH—CH₂—CH₂—NHCO—; each of R9 and R10 is phenyl; R11 is COOCH₃; and n is 3. In one embodiment, the compound is according to general formula III, where each of R1 and R2 is sulfoalkyl; each of R5 and R6 is methyl; each of R7 and R8 is SO₃; m is 2; o is 3; L is —CONH—CH₂—CH₂—NHCO—; each of R9 and R10 is phenyl; R11 is COOCH₃; and n is 3. In one embodiment, the compound is according to general formula III, where each of R1 and R2 is sulfoalkyl; each of R5 and R6 is methyl; each of R7 and R8 is SO₃; m is 3; o is 3; L is —CONH—CH₂—CH₂—NHCO—; each of R9 and R10 is phenyl; R11 is COOCH₃; and n is 3. In one embodiment, the compound is according to general formula III, where each of R1 and R2 is sulfoalkyl; each of R5 and R6 is methyl; each of R7 and R8 is SO₃; m is 4; o is 3; L is —CONH—CH₂—CH₂—NHCO—; each of R9 and R10 is phenyl; R11 is COOCH₃; and n is 3. In one embodiment, the compound is according to general formula III, where each of R1 and R2 is sulfoalkyl; each of R5 and R6 is methyl; each of R7 and R8 is SO₃; m is 5; o is 3; L is —CONH—CH₂—CH₂—NHCO—; each of R9 and R10 is phenyl; R11 is COOCH₃; and n is 3.

In one embodiment, the compound is according to general formula III, where each of $R^1$, $R^2$, $R^5$, and $R^6$ is the same or different and is independently selected from an aliphatic, heteroaliphatic, sulfoalkyl group, heteroaliphatic with terminal SO₃, a PEG group P-$L^1$-Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -$L^1$-SO₂NH—P-$L^1$-Z, and a carboxamide group -$L^1$-CONH—P-$L^1$-Z; each of $R^7$ and $R^8$, and each R in the benzocyanine form is the same or different and is independently selected from H, SO₃, a PEG group P-$L^1$-Z where P is selected from an ethylene glycol group, a diethylene glycol group, and a polyethylene glycol group, where the polyethylene glycol group is $(CH_2CH_2O)_5$, where s is an integer from 3-6 inclusive, a sulfonamide group —C—SO₂NH—P-$L^1$-Z, and a carboxamide group -$L^1$-CONH—P-$L^1$-Z; where C is selected from a divalent linear (—(CH₂)$_o$—, o=0 to 15), branched, or cyclic alkane group that can be substituted by at least one atom selected from oxygen, substituted nitrogen, and/or sulfur; where Z is selected from H, CH₃, an alkyl group, and a heteroalkyl group; Kat is a number of Na⁺, K⁺, Ca²⁺, ammonia, or other cation(s) needed to compensate the negative charge brought by the cyanine; m is an integer from 0 to 5 inclusive; o is an integer from 0 to 12 inclusive; and n is an integer from 1 to 3 inclusive; with the proviso that at least one of $R^1$, $R^2$, $R^5$, $R^6$, $R^7$, and $R^8$ contains a PEG group.

In one embodiment, the compound is 550 Compound 1-phosphine

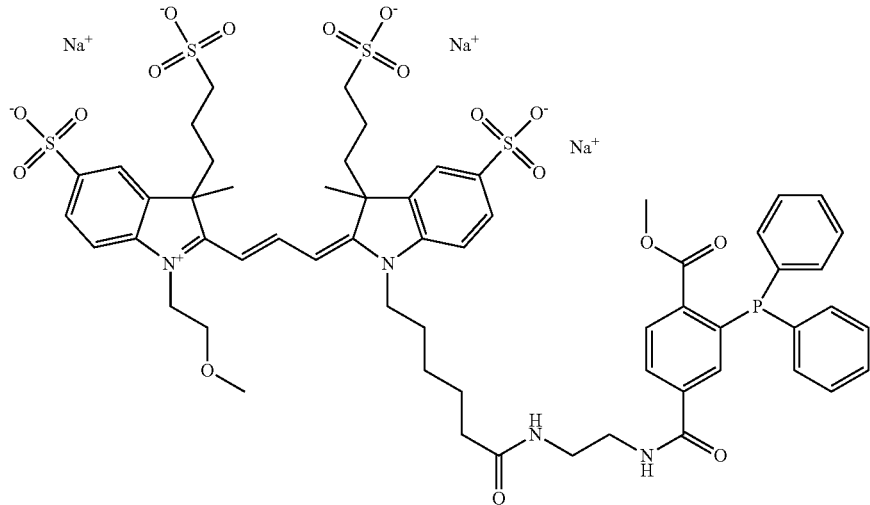

550 Compound 1-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-1-(2-methoxyethyl)-3-methyl-3-(3-sulfonatopropyl)-3H-indolium-5-sulfonate) contains an ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In one embodiment, the compound is 550 Compound 2-phosphine

550 Compound 2-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-1-(2-(2-methoxyethoxy)ethyl)-3-methyl-3-(3-sulfonatopropyl)-3H-indolium-5-sulfonate) contains a diethylene glycol on the indole N of the left heterocycle. The methyl group on the diethylene glycol prevents the terminal —OH from oxidation. Oxidation is known to occur, over time, on an unprotected PEG terminus. Adding a methyl ether provides this protection, and prevents reaction with electrophilic reactive groups.

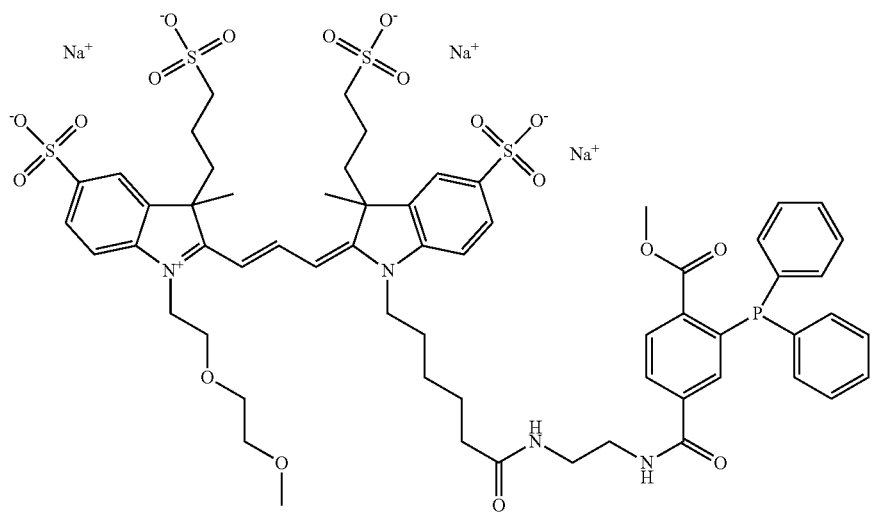

In one embodiment, the compound is 550 Compound 3-phosphine

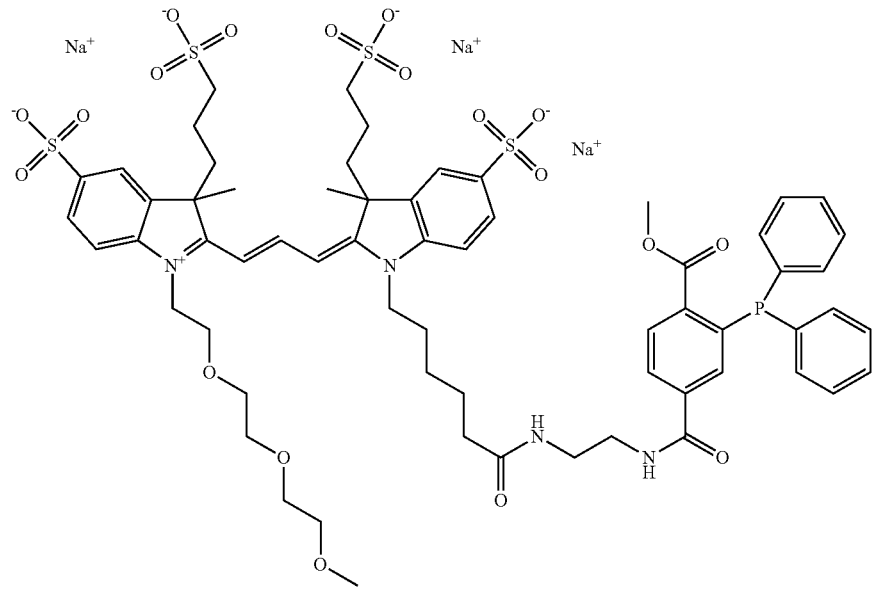

550 Compound 3-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-1-(2-(2-(2-methoxyethoxy)ethoxy)ethyl)-3-methyl-3-(3-sulfonatopropyl)-3H-indolium-5-sulfonate) contains a polyethylene glycol on the indole N of the left heterocycle. The methyl group on the polyethylene glycol prevents the terminal —OH from oxidation. Oxidation is known to occur, over time, on an unprotected PEG terminus. Adding a methyl ether provides this protection, and prevents reaction with electrophilic reactive groups.

In one embodiment, the compound is 550 Compound 4-phosphine

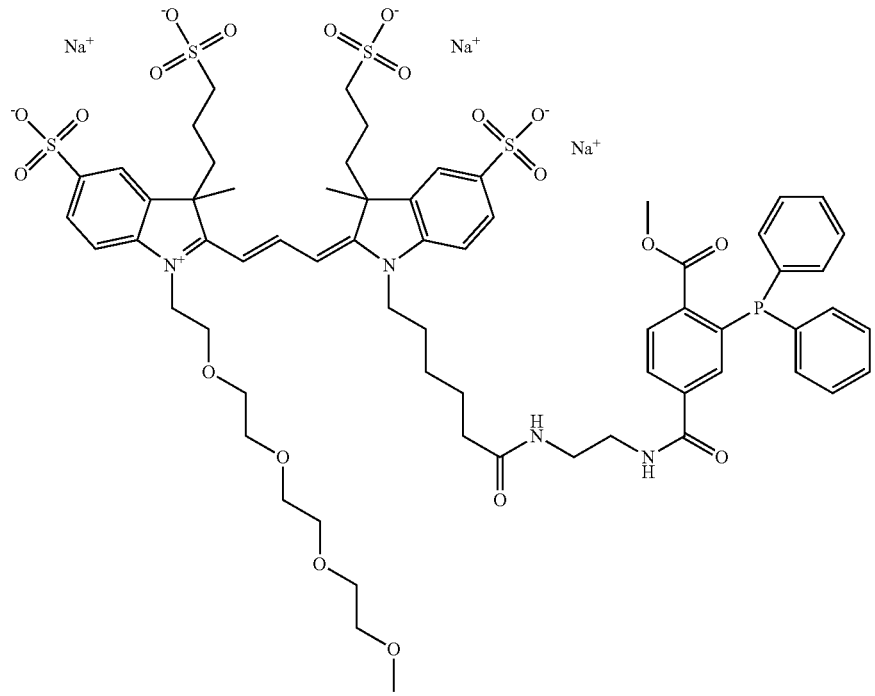

550 Compound 4-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-3-methyl-3-(3- sulfonatopropyl)-1-(2,5,8,11-tetraoxamidecan-13-yl)-3H-indolium-5-sulfonate) contains a polyethylene glycol on the indole N of the left heterocycle.

In one embodiment, the compound is 550 Compound 5-phosphine

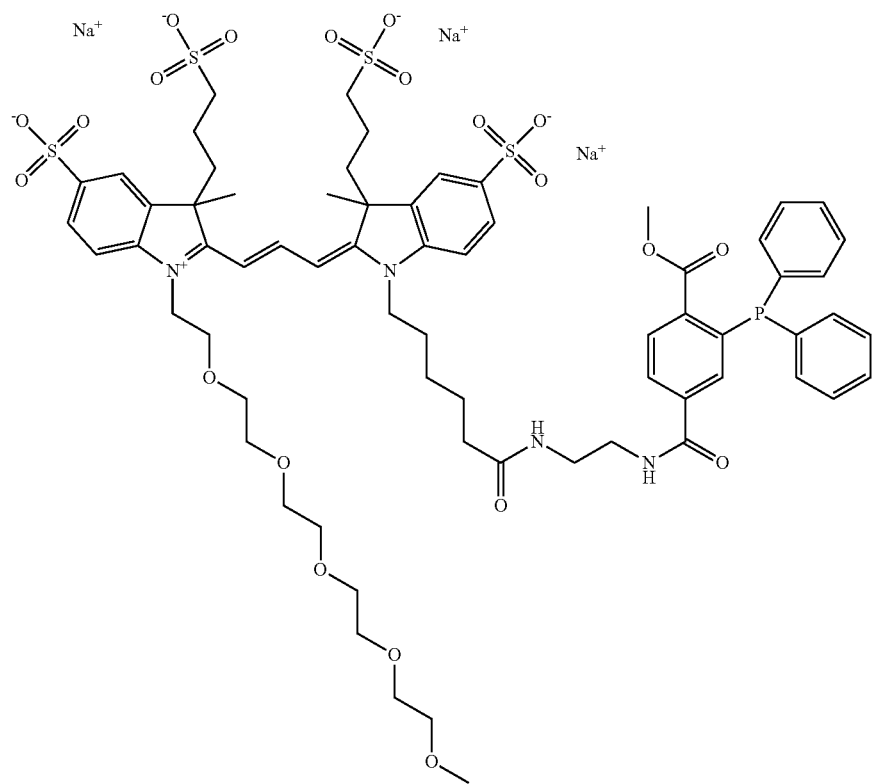

550 Compound 5-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-1-(2,5,8,11,14-pentaoxahexadecan-16-yl)-3-methyl-3-(3-sulfonatopropyl)-3H-indolium-5-sulfonate) contains a polyethylene glycol on the indole N of the left heterocycle.

In one embodiment, the compound is 550 Compound 6-phosphine

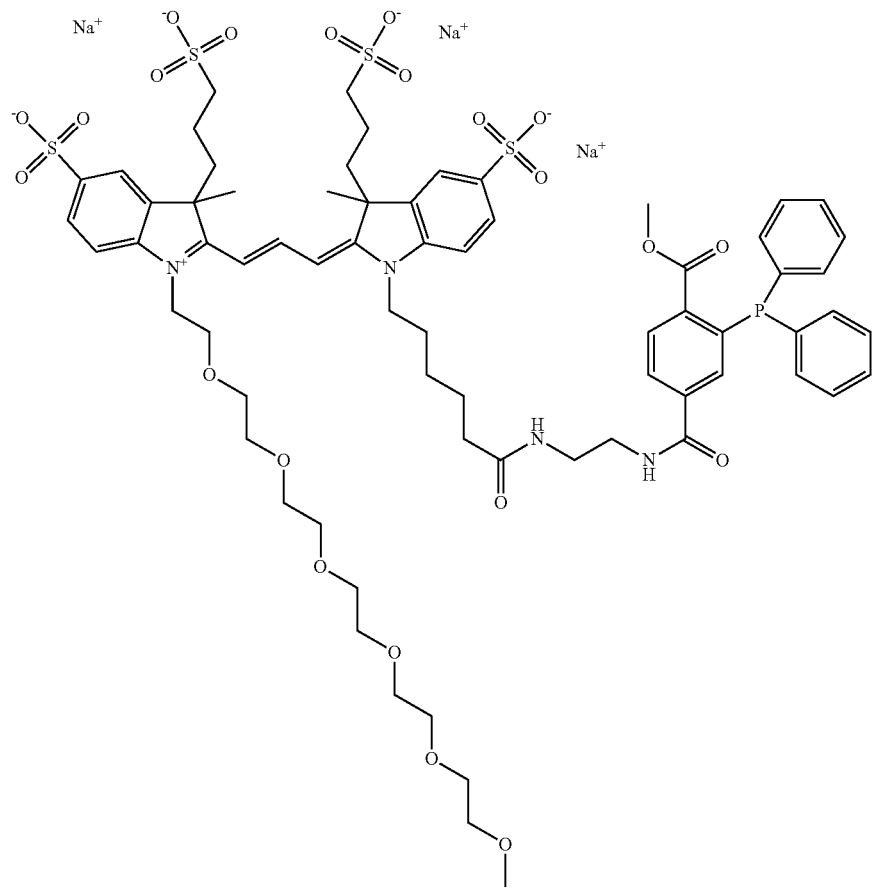

550 Compound 6-phosphine (2-((1E,3E)-3-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)prop-1-enyl)-3-methyl-1-(2,5,8,11,14,17-hexaoxanonadecan-19-yl)-3-(3-sulfonatopropyl)-3H-indolium-5-sulfonate) contains a polyethylene glycol on the indole N of the left heterocycle.

In embodiments, the degree of sulfonation is varied to, e.g., vary the compound's degree of hydrophilicity or hydrophobicity. One non-limiting example is a monosulfonate form of 550 Compound 1-phosphine, shown below, but it is understood that the single sulfo group can be at any of the described positions:

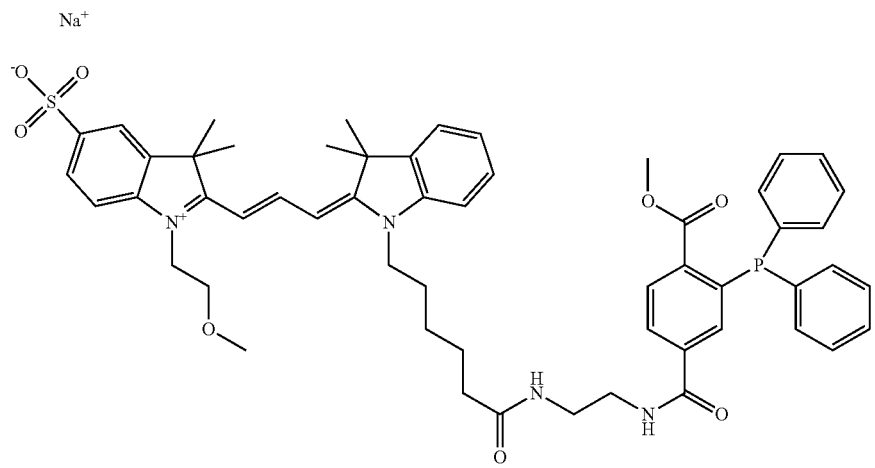

One non-limiting example is a disulfonate form of 550 Compound 1-phosphine, shown below, but it is understood that each of the two sulfo groups can be at any of the described positions:

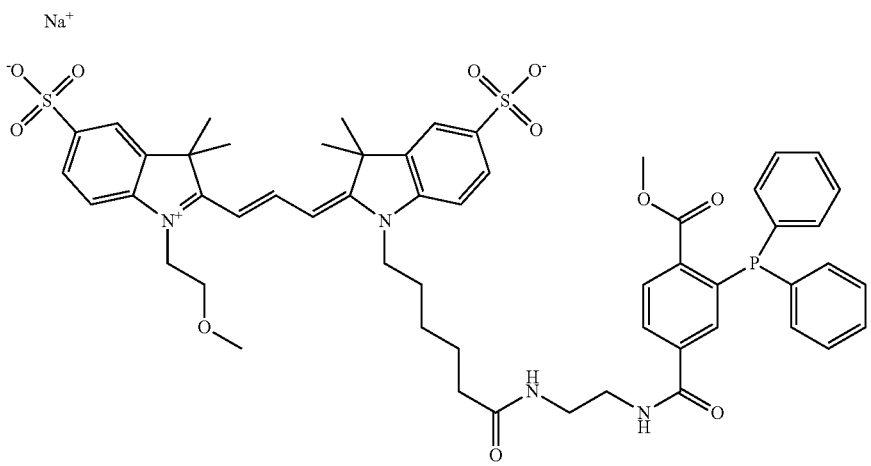
One non-limiting example is a trisulfonate form of 550 Compound 1-phosphine, shown below, but it is understood that each of the three sulfo groups can be at any of the described positions:
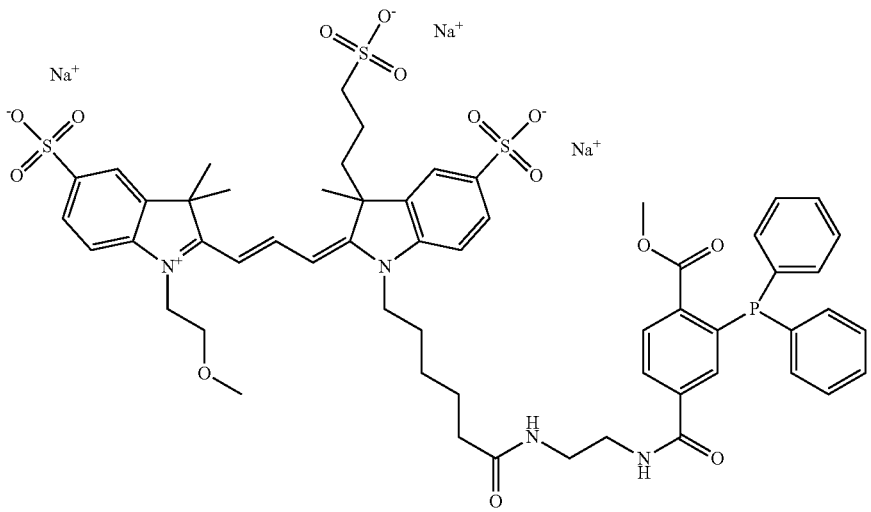
One non-limiting example is a tetrasulfonate form of 550 Compound 1-phosphine, shown below, but it is understood that each of the four sulfo groups can be at any of the described positions:
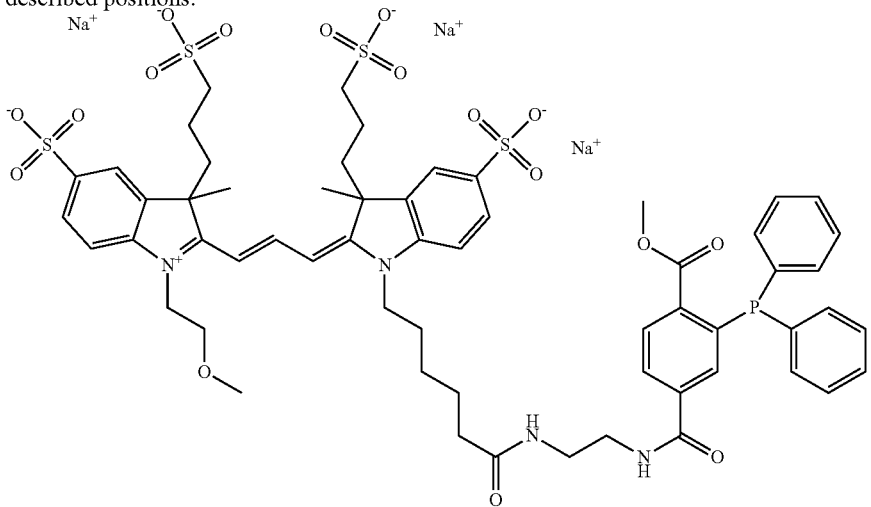

In one embodiment, the compound is 650 Compound 1-phosphine

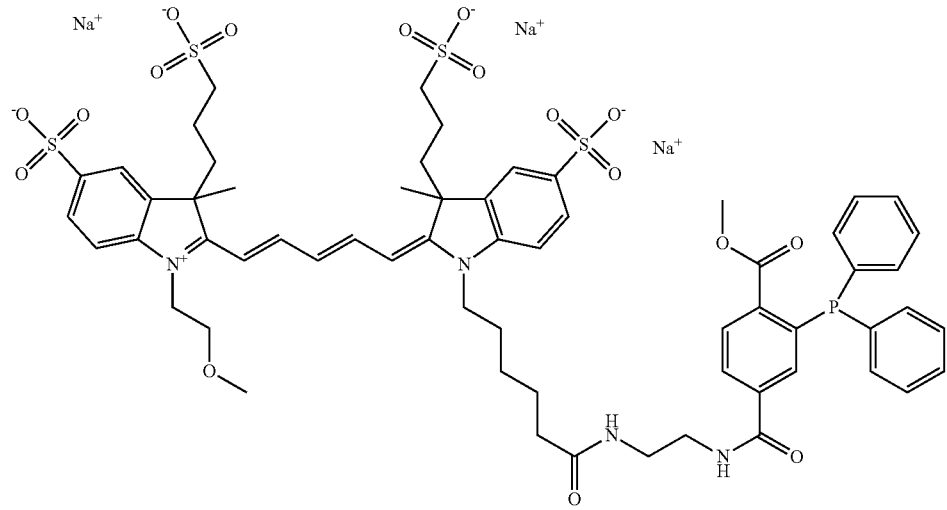

650 Compound 1-phosphine (2-((1E,3E,5E)-5-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)penta-1,3-dienyl)-1-(2-methoxyethyl)-3-methyl-3-(3-sulfonatopropyl)-3H-indolium-5-sulfonate) contains an ethylene glycol on the indole N of the left heterocycle.

In one embodiment, the compound is 650 Compound 2-phosphine

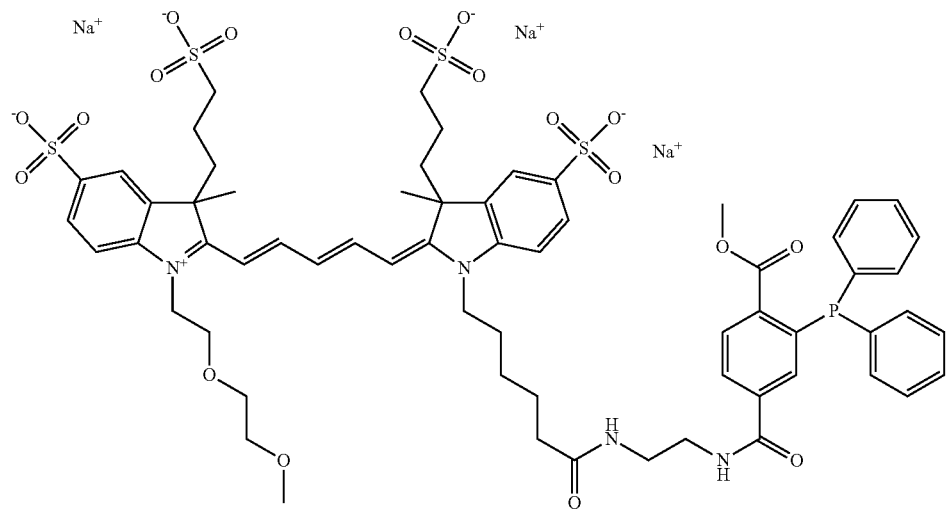

650 Compound 2-phosphine (2-((1E,3E,5E)-5-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)penta-1,3-dienyl)-1-(2-(2-methoxyethoxy)ethyl)-3-methyl-3-(3-sulfonatopropyl)-3H-indolium-5-sulfonate) contains a diethylene glycol on the indole N of the left heterocycle.

In one embodiment, the compound is 650 Compound 3-phosphine

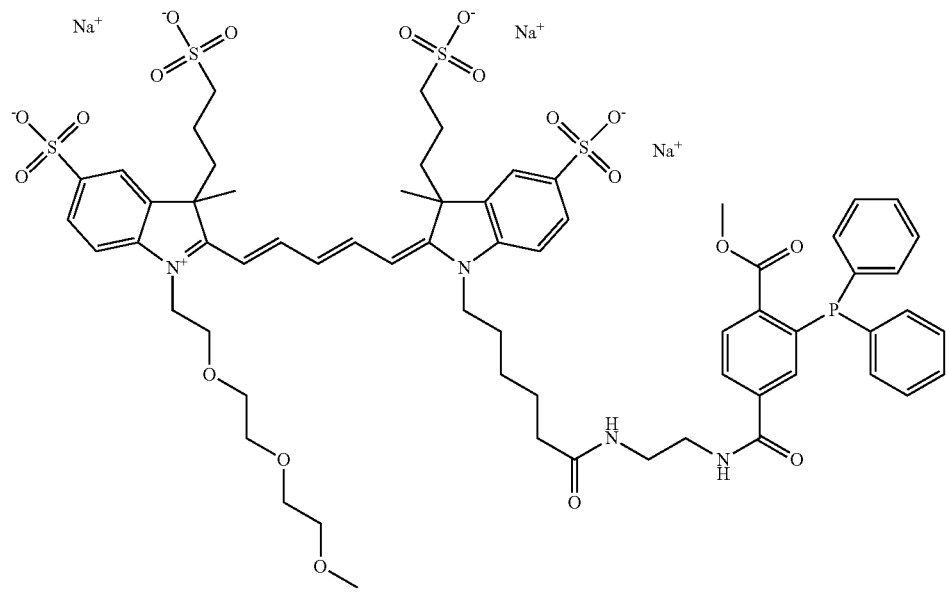

650 Compound 3-phosphine (2-((1E,3E,5E)-5-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)penta-1,3-dienyl)-1-(2-(2-(2-methoxyethoxy)ethoxy)ethyl)-3-methyl-3-(3-sulfonatopropyl)-3H-indolium-5-sulfonate) contains a polyethylene glycol on the indole N of the left heterocycle.

In one embodiment, the compound is 650 Compound 4-phosphine

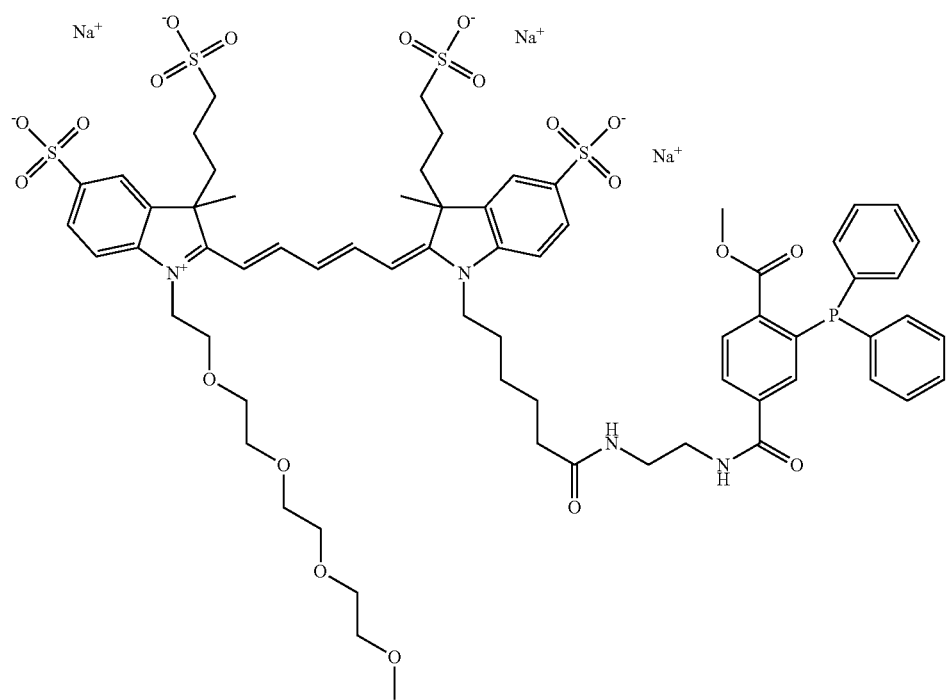

650 Compound 4-phosphine (2-((1E,3E,5E)-5-(1-(6-(2-(3-(diphenylphosphino)-4-(methoxycarbonyl)benzamido) ethylamino)-6-oxohexyl)-3-methyl-5-sulfonato-3-(3-sulfonatopropyl)indolin-2-ylidene)penta-1,3-dienyl)-3-methyl-3-(3-sulfonatopropyl)-1-(2,5,8,11-tetraoxamidecan-13-yl)-3H-indolium-5-sulfonate) contains a polyethylene glycol on the indole N of the left heterocycle.

In one embodiment, the compound is 650 Compound 5-phosphine

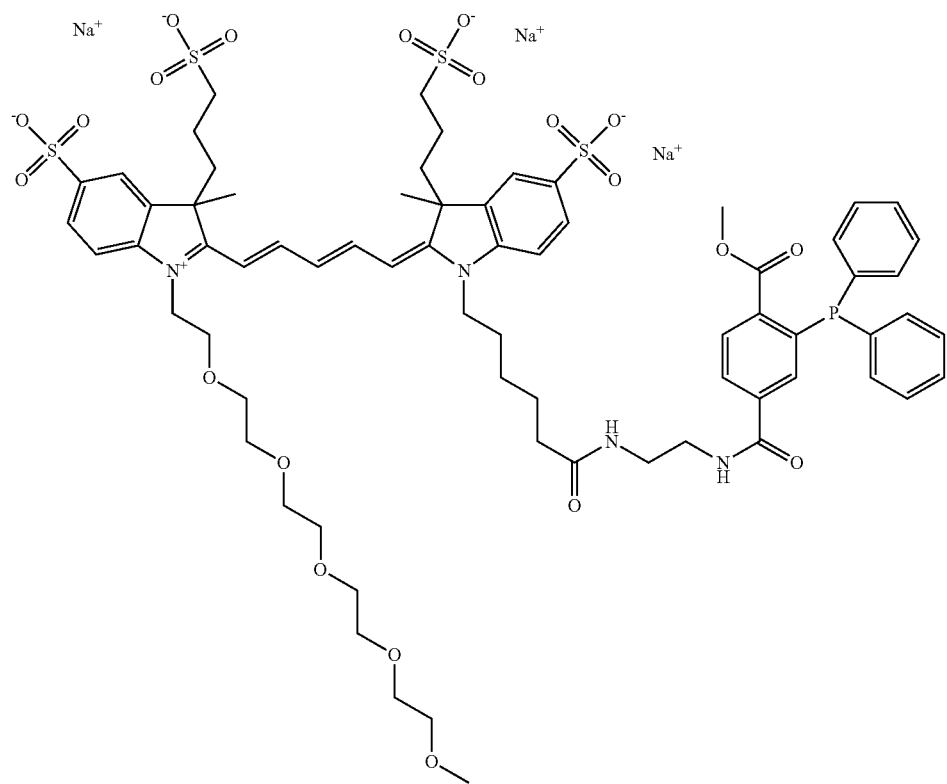

650 Compound 5-phosphine (2-((1E,3E,5E)-5-(1-(6-(2-(3-(diphenylphosphino)-4-(methoxycarbonyl)benzamido) ethylamino)-6-oxohexyl)-3-methyl-5-sulfonato-3-(3-sulfonatopropyl)indolin-2-ylidene)penta-1,3-dienyl)-1-(2,5,8,11,14-pentaoxahexadecan-16-yl)-3-methyl-3-(3-sulfonatopropyl)-3H-indolium-5-sulfonate) contains a polyethylene glycol on the indole N of the left heterocycle.

In one embodiment, the compound is 650 Compound 6-phosphine

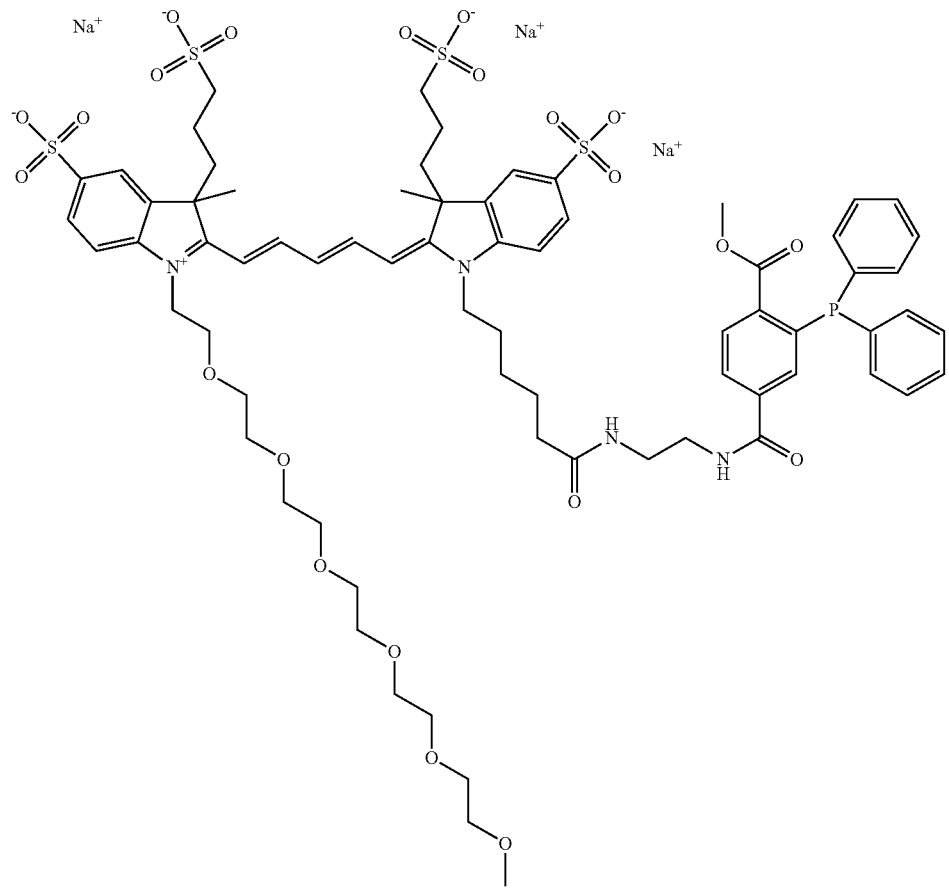

650 Compound 6-phosphine (2-((1E,3E,5E)-5-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)penta-1,3-dienyl)-3-methyl-1-(2,5,8,11,14,17-hexaoxanonadecan-19-yl)-3-(3-sulfonatopropyl)-3H-indolium-5-sulfonate) contains a polyethylene glycol on the indole N of the left heterocycle.

In embodiments, the degree of sulfonation is varied to, e.g., vary the compound's degree of hydrophilicity or hydrophobicity. One non-limiting example is a monosulfonate form of 650 Compound 1-phosphine, shown below, but it is understood that the single sulfo group can be at any of the described positions:

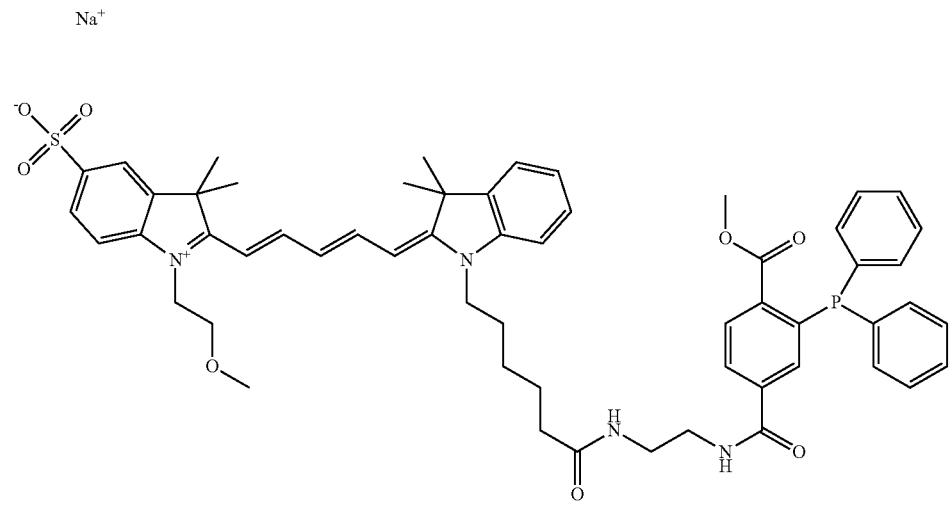

One non-limiting example is a disulfonate form of 650 Compound 1-phosphine, shown below, but it is understood that each of the two sulfo groups can be at any of the described positions:

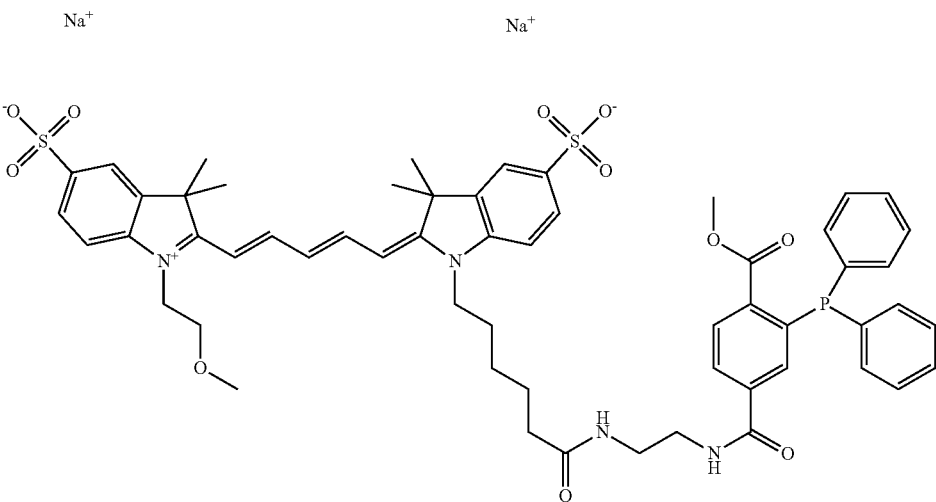
One non-limiting example is a trisulfonate form of 650 Compound 1-phosphine, shown below, but it is understood that each of the three sulfo groups can be at any of the described positions:
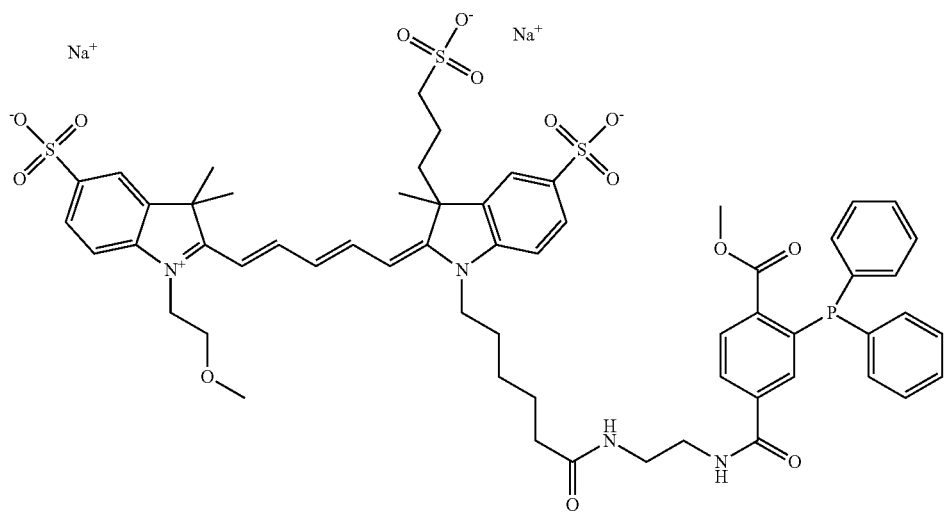
One non-limiting example is a tetrasulfonate form of 650 Compound 1-phosphine, shown below, but it is understood that each of the four sulfo groups can be at any of the described positions:

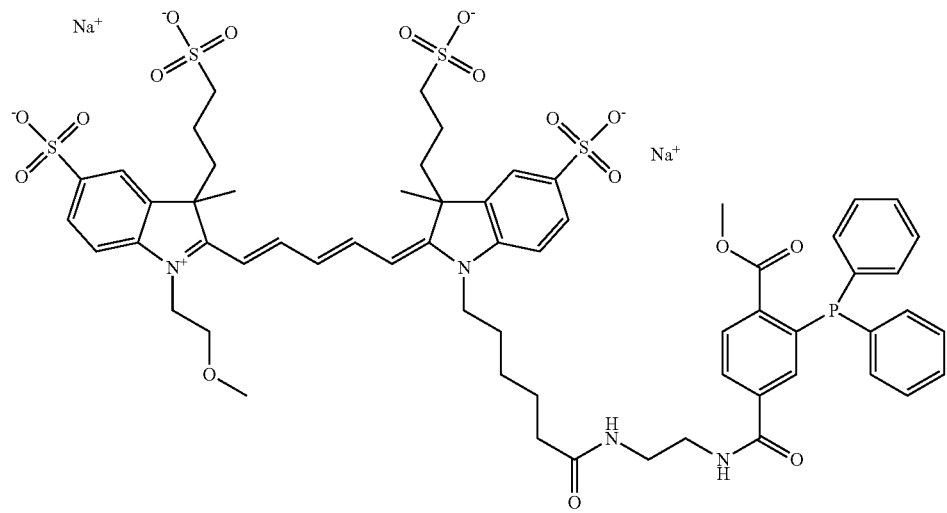

In one embodiment, the compound is 755 Compound 1-phosphine

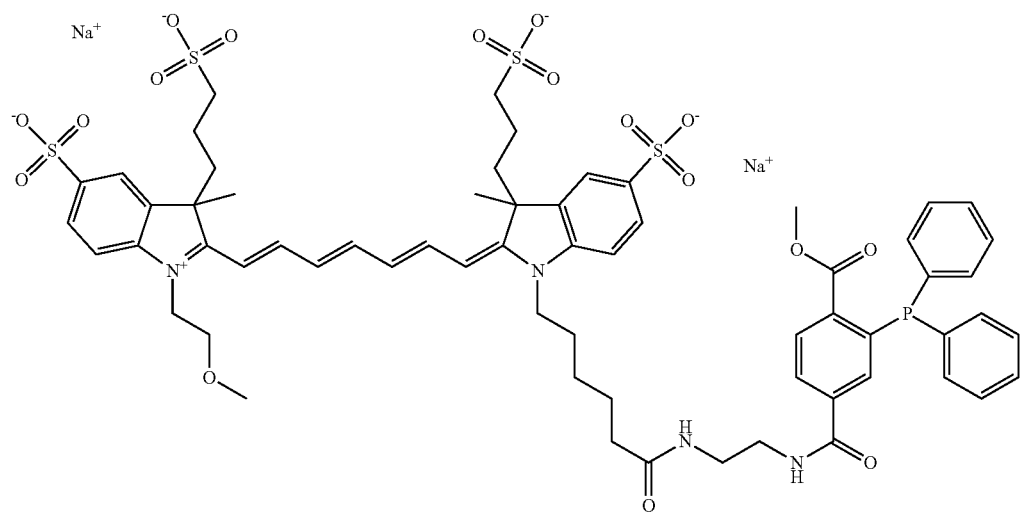

755 Compound 1-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-1-(2-methoxyethyl)-3-methyl-3-(3-sulfonatopropyl)-3H-indolium-5-sulfonate) contains an ethylene glycol on the indole N of the left heterocycle.

In one embodiment, the compound is 755 Compound 2-phosphine

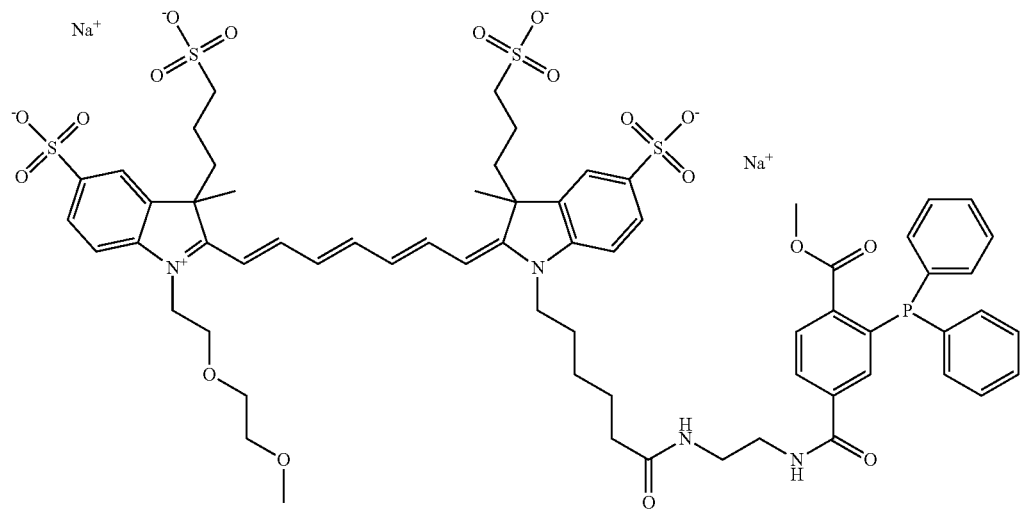

755 Compound 2-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-1-(2-(2-methoxyethoxy)ethyl)-3-methyl-3-(3-sulfonatopropyl)-3H-indolium-5-sulfonate) contains a diethylene glycol on the indole N of the left heterocycle.

In one embodiment, the compound is 755 Compound 3-phosphine

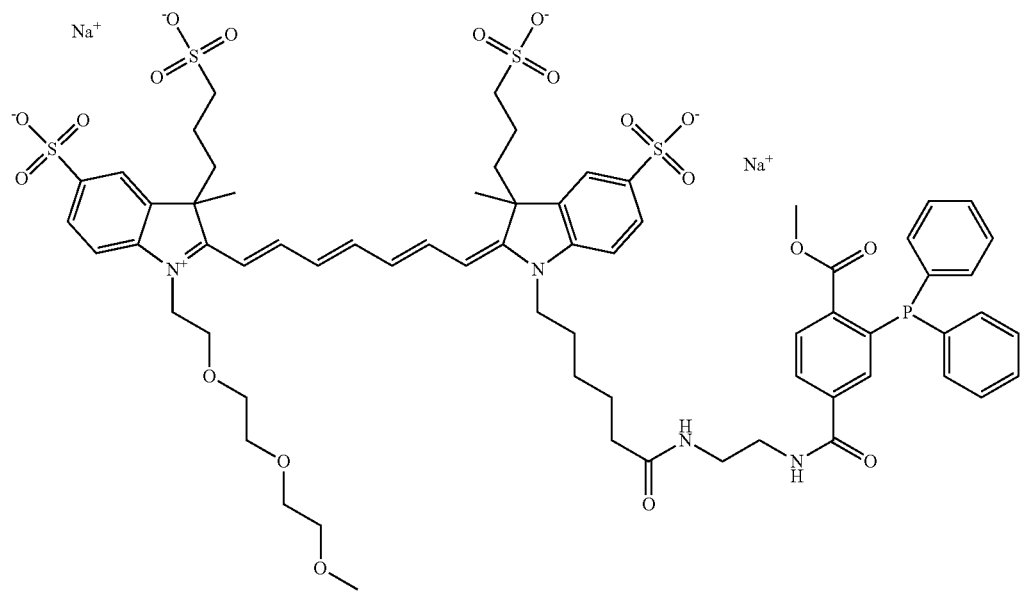

755 Compound 3-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-1-(2-(2-(2-methoxyethoxy)ethoxy)ethyl)-3-methyl-3-(3-sulfonatopropyl)-3H-indolium-5-sulfonate) contains a polyethylene glycol on the indole N of the left heterocycle.

In one embodiment, the compound is 755 Compound 4-phosphine

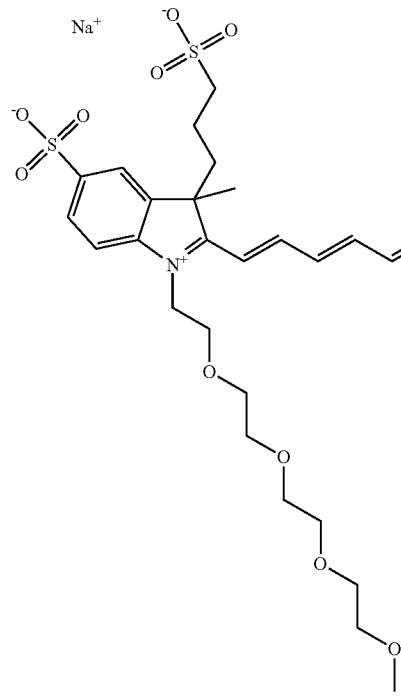
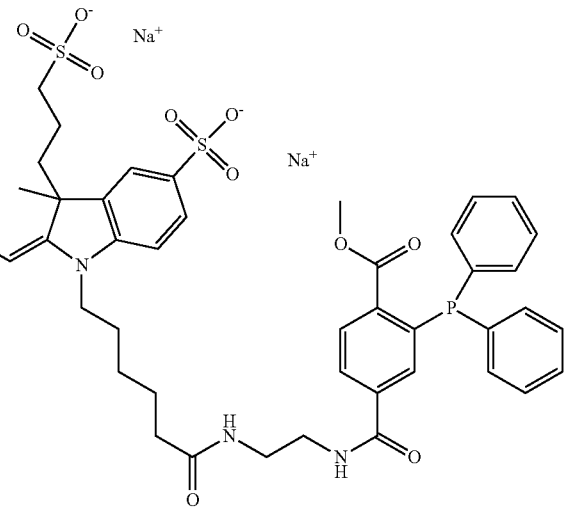
755 Compound 4-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-3-methyl-3-(3-sulfonatopropyl)-1-(2,5,8,11-tetraoxamidecan-13-yl)-3H-indolium-5-sulfonate) contains a polyethylene glycol on the indole N of the left heterocycle.
In one embodiment, the compound is 755 Compound 5-phosphine
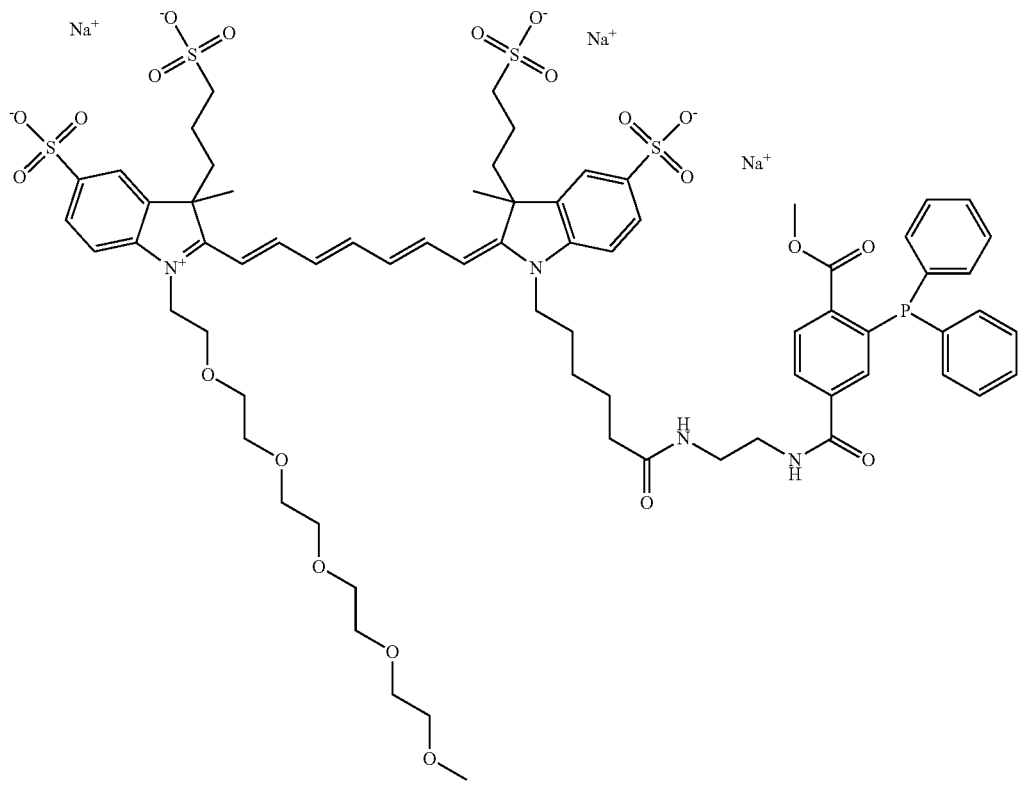

755 Compound 5-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-1-(2,5,8,11,14-pentaoxahexadecan-16-yl)-3-methyl-3-(3-sulfonatopropyl)-3H-indolium-5-sulfonate) contains a polyethylene glycol on the indole N of the left heterocycle.

In one embodiment, the compound is 755 Compound 6-phosphine

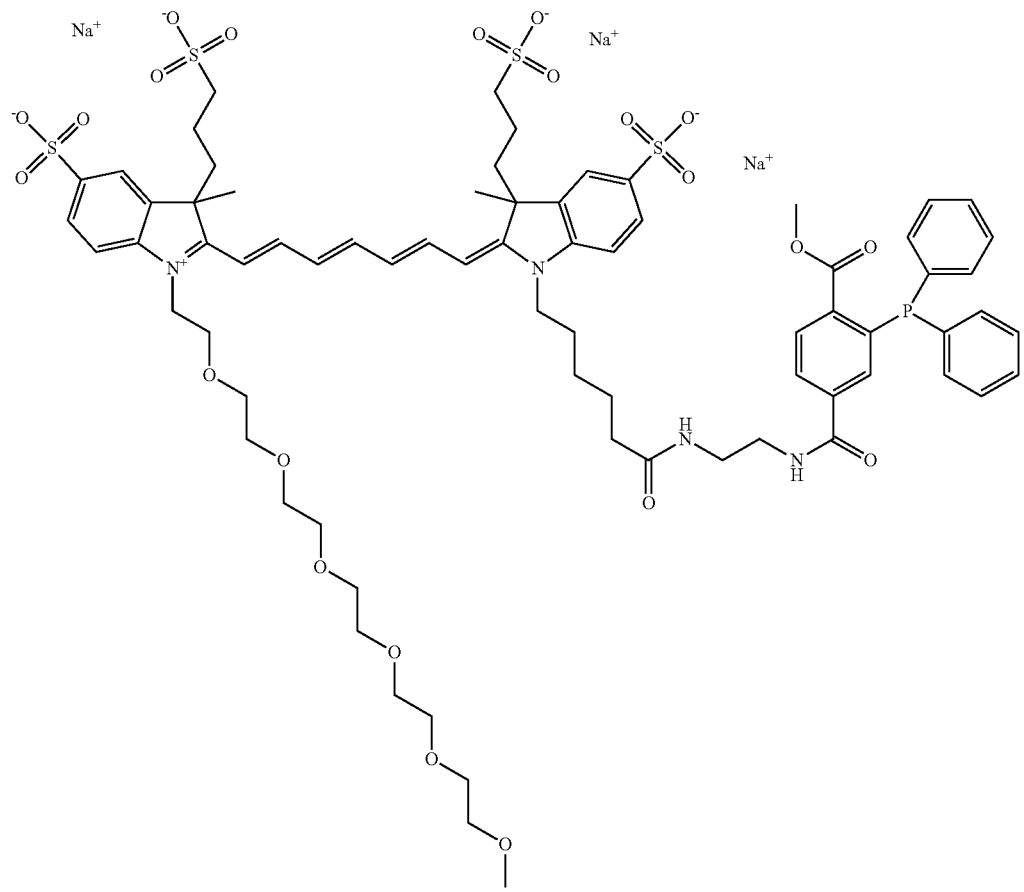

755 Compound 6-phosphine (2-((1E,3E,5E,7E)-7-(1-(6-(2-(3-(diphenylphosphino)-4-(methoxycarbonyl)benzamido)ethylamino)-6-oxohexyl)-3-methyl-5-sulfonato-3-(3-sulfonatopropyl)indolin-2-ylidene)hepta-1,3,5-trienyl)-3-methyl-1-(2,5,8,11,14,17-hexaoxanonadecan-19-yl)-3-(3-sulfonatopropyl)-3H-indolium-5-sulfonate) contains a polyethylene glycol on the indole N of the left heterocycle.

In embodiments, the degree of sulfonation is varied to, e.g., vary the compound's degree of hydrophilicity or hydrophobicity. One non-limiting example is a monosulfonate form of 755 Compound 1-phosphine, shown below, but it is understood that the single sulfo group can be at any of the described positions:

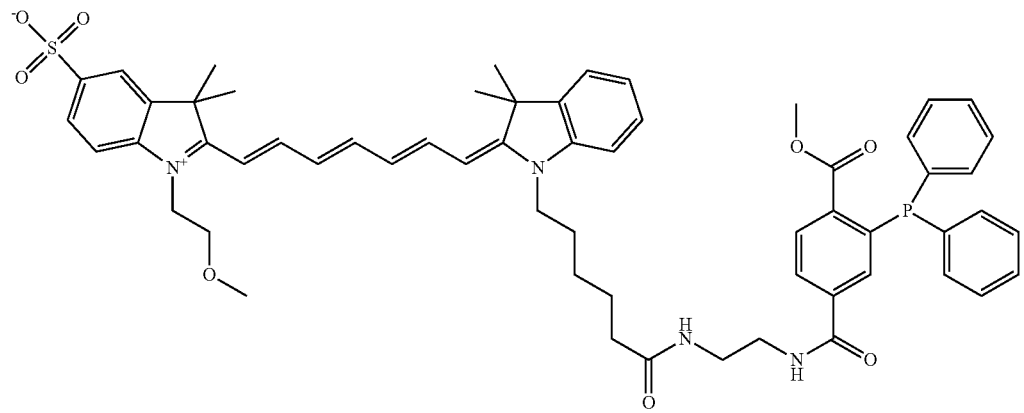
One non-limiting example is a disulfonate form of 755 Compound 1-phosphine, shown below, but it is understood that the each of the two sulfo groups can be at any of the described positions:
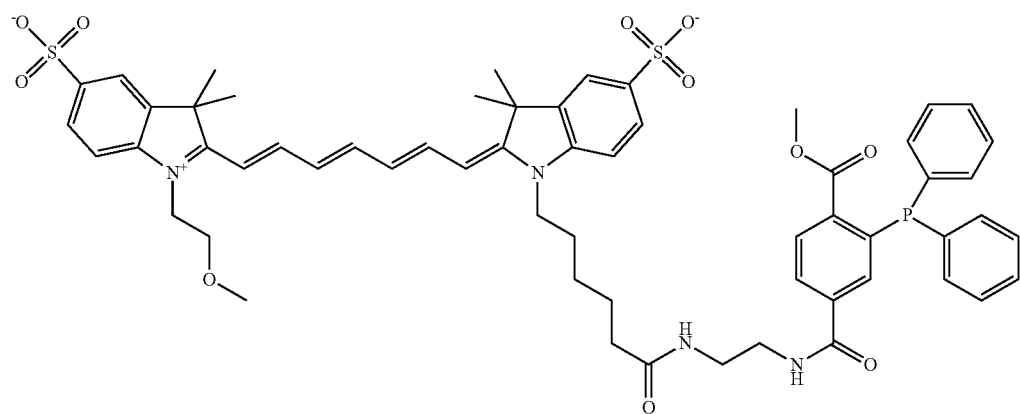
One non-limiting example is a trisulfonate form of 755 Compound 1-phosphine, shown below, but it is understood that the each of the three sulfo groups can be at any of the described positions:

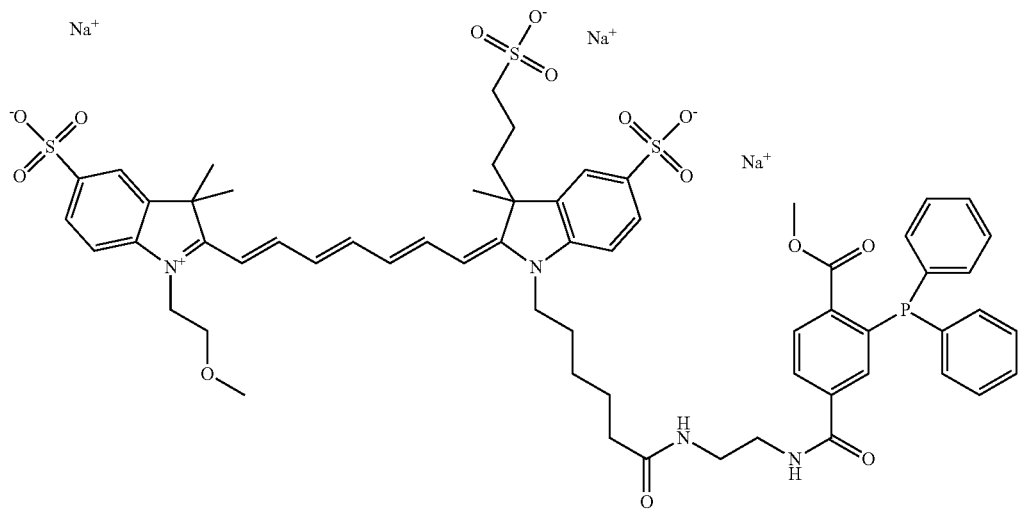

One non-limiting example is a tetrasulfonate form of 755 Compound 1-phosphine, shown below, but it is understood that the each of the four sulfo groups can be at any of the described positions:

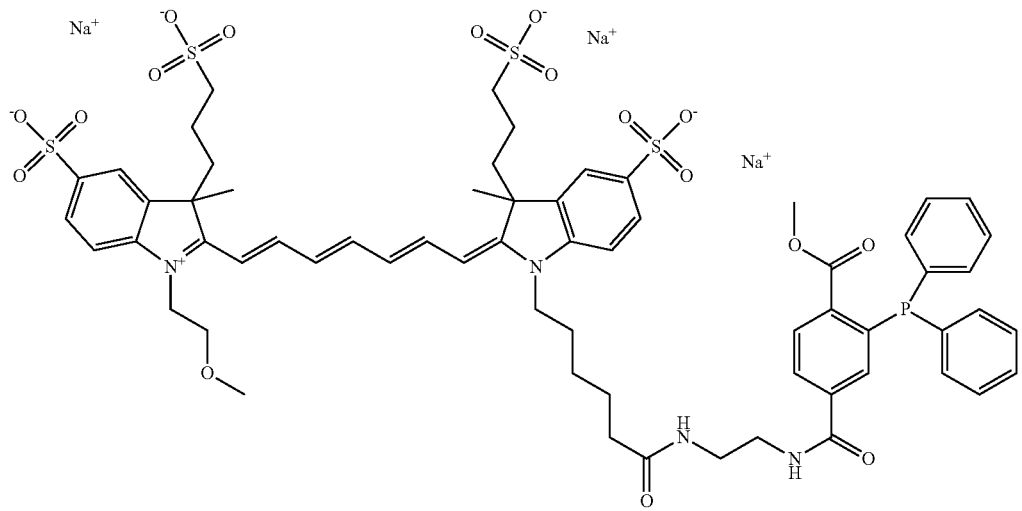

In one embodiment, the compound has general formula IV

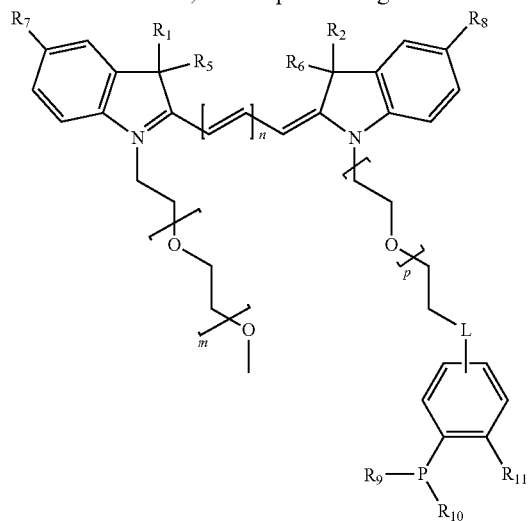

where each of $R^1$, $R^2$, $R^5$, and $R^6$ is the same or different and is independently selected from the group consisting of an aliphatic, heteroaliphatic, sulfoalkyl group, or heteroaliphatic with terminal $SO_3$; each of $R^7$ and $R^8$ is the same or different and is independently selected from either H, $SO_3$, sulfoalkyl, heteroaliphatic, or heteroaliphatic with terminal $SO_3$; each of R9 and R10 is the same or different and is independently selected from either aryl groups, substituted aryl groups, or cycloalkyl groups; R11 is an electrophilic group selected from the group consisting of a carboxylic acid, an alkyl ester, an aryl ester, a substituted aryl ester, an aldehyde, and amide, an aryl amide, an alkyl halide, a thioester, a sulfonyl ester, and alkyl ketone, an aryl ketone, a substituted aryl ketone, a halosulfonyl, a nitrile, and a nitro; L is a linking group that forms a covalent bond between the dye and the phosphine; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; and n is an integer from 1 to 3 inclusive. The benzocyanine form of the above compound is as described above, where each R is selected from the group described for R7 and R8.

In one embodiment, the compound is according to general formula IV, where each of R1 and R2 is sulfoalkyl; each of R5 and R6 is methyl; each of R7 and R8 is SO$_3$; m is 0; p is 1; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 0; p is 2; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 0; p is 3; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 0; p is 4; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 0; p is 5; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 0; p is 6; L is —CONH—CH$_2$—CH$_2$—NHCO—; each of R9 and R10 is phenyl; R11 is COOCH$_3$; and n is 1.

In one embodiment, the compound is according to general formula IV, where each of R1 and R2 is sulfoalkyl; each of R5 and R6 is methyl; each of R7 and R8 is SO$_3$; m is 0; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 are sulfoalkyl; each of R5 and R6 is methyl; each of R7 and R8 are SO$_3$; m is 0; p is 2; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 are sulfoalkyl; each of R5 and R6 is methyl; each of R7 and R8 are SO$_3$; m is 0; p is 3; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 0; p is 4; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 0; p is 5; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 0; p is 6; L is —CONH—CH$_2$—CH$_2$—NHCO—; each of R9 and R10 is phenyl; R11 is COOCH$_3$; and n is 2.

In one embodiment, the compound is according to general formula IV, where each of R1 and R2 are sulfoalkyl; each of R5 and R6 are methyl; each of R7 and R8 are SO$_3$; m is 0; p is 1; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 0; p is 2; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 0; p is 3; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 sulfoalkyl; each of R5 and R6 is methyl; each of R7 and R8 is SO$_3$; m is 0; p is 4; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 0; p is 5; L is —CONH—CH$_2$—CH$_2$—NHCO—; each of R9 and R10 is phenyl; R11 is COOCH$_3$; and n is 3. In one embodiment, the compound is according to general formula III, where each of R1 and R2 is sulfoalkyl; each of R5 and R6 is methyl; each of R7 and R8 is SO$_3$; m is 0; p is 6; L is —CONH—CH$_2$—CH$_2$—NHCO—; each of R9 and R10 is phenyl; R11 is COOCH$_3$; and n is 3.

In one embodiment, the compound is according to general formula IV, where each of R1 and R2 is sulfoalkyl; each of R5 and R6 is methyl; each of R7 and R8 is SO$_3$; m is 0; p is 1; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 sulfoalkyl; each of R5 and R6 is methyl; each of R7 and R8 is SO$_3$; m is 1; p is 1; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 2; p is 1; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 3; p is 1; L is —CONH—CH$_2$—CH$_2$—NHCO—; each of R9 and R10 is phenyl; R11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 4; p is 1; L is —CONH—CH$_2$—CH$_2$—NHCO—; each of R9 and R10 is phenyl; 11 is COOCH$_3$; and n is 1. In one embodiment, the compound is according to general formula IV, where each of R1 and R2 is sulfoalkyl; each of R5 and R6 is methyl; each of R7 and R8 is SO$_3$; m is 5; p is 1; L is —CONH—CH$_2$—CH$_2$—NHCO—; each of R9 and R10 is phenyl; R11 is COOCH$_3$; and n is 1.

In one embodiment, the compound is according to general formula IV, where each of R1 and R2 is sulfoalkyl; each of R5 and R6 is methyl; each of R7 and R8 is SO$_3$; m is 0; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 1; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 2; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 3; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 4; p is 1; L is —CONH—CH$_2$—CH$_2$—NHCO—; each of R9 and R10 is phenyl; R11 is COOCH$_3$; and n is 2. In one embodiment, the compound is according to general formula IV, where each of R1 and R2 is sulfoalkyl; each of R5 and R6 is methyl; each of R7 and R8 is SO$_3$; m is 5; p is 1; L is —CONH—CH$_2$—CH$_2$—NHCO—; each of R9 is R10 are phenyl; R11 is COOCH$_3$; and n is 2.

In one embodiment, the compound is according to general formula IV, where each of R1 and R2 is sulfoalkyl; each of R5 and R6 is methyl; each of R7 and R8 is SO$_3$; m is 0; p is 1; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 1; p is 1; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 2; p is 1; L is —CONH—CH$_2$—CH$_2$—NHCO—; R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 3; p is 1; L is —CONH—CH$_2$—CH$_2$—NHCO—; each of R9 and R10 is phenyl; R11 is COOCH$_3$; and n is 3. In one embodiment, the compound is according to general formula IV, where each of R1 and R2 is sulfoalkyl; each of R5 and R6 is methyl; each of R7 and R8 is SO$_3$; m is 4; p is 1; L is —CONH—CH$_2$—CH$_2$—NHCO—; each of R9 and R10 is phenyl; R11 is COOCH$_3$; and n is 3. In one embodiment, the compound is according to general formula III, where each of R1 and R2 is sulfoalkyl; each of R5 and R6 is methyl; each of R7 and R8 is SO$_3$; m is 5; p is 1; L is —CONH—CH$_2$—CH$_2$—NHCO—; each of R9 and R10 is phenyl; R11 is COOCH$_3$; and n is 3.

In one embodiment, the compound is according to general formula IV, where each of $R^1$, $R^2$, $R^5$, and $R^6$ is the same or different and is independently selected from an aliphatic, heteroaliphatic, sulfoalkyl group, heteroaliphatic with terminal SO$_3$, a PEG group P-L$^1$-Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L$^1$-SO$_2$NH—P-L$^1$-Z, and a carboxamide group -L$^1$-CONH—P-L$^1$-Z; each of $R^7$ and $R^8$ and each R in the benzocyanine form is the same or different and is independently selected from H, SO$_3$, a PEG group P-L$^1$-Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L$^1$-SO$_2$NH—P-L$^1$-Z, and a carboxamide group -L$^1$-CONH—P-L$^1$-Z; where L$^1$ is selected from a divalent linear (—(CH$_2$)$_o$—, o=0 to 15), branched, or cyclic alkane group that can be substituted by at least one atom selected from oxygen, substituted nitrogen, and/or sulfur; where Z is selected from H, CH$_3$, an alkyl group, and a heteroalkyl group; Kat is a number of Na$^+$, K$^+$, Ca$^{2+}$, ammonia, or other cation(s) needed to compensate the negative charge brought by the cyanine; m is an integer from 0 to 5 inclusive; p is an integer from 1 to 6 inclusive; and n is an integer from 1 to 3 inclusive; with the proviso that at least one of $R^1$, $R^2$, $R^5$, $R^6$, $R^7$, and $R^8$ contains a PEG group.

In various embodiments, an ethylene glycol group, diethylene glycol group, and/or a polyethylene glycol group, which will collectively be referred to as a PEG group, unless specifically defined, may be present at position(s) in addition to such groups being present on the N atom(s) of the indole structure.

In embodiments, the degree of sulfonation is varied to, e.g., vary the compound's degree of hydrophilicity or hydrophobicity. In embodiments, e.g., for functional assays, the inventive compounds are activated. Activation of the compound adds a chemical moiety such that the compound is in a form that can be conjugated to a biological moiety. In one example, a phosphine group, as shown in general formulas III and IV, is present on the inventive compounds. In embodiments, the compound may contain one or more substitutions of the polymethine linker.

The disclosed compounds are useful as chromophores and/or fluorophores. For example, they can be used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

The compounds containing the disclosed functionality or functionalities are synthesized using methods known in the art and as subsequently described.

König U.S. Pat. No. 1,524,791 and GB 434875 describes the core indocyanine without additional functionalities, its synthesis, and 3-, 5-, and 7-membered polymethine chains.

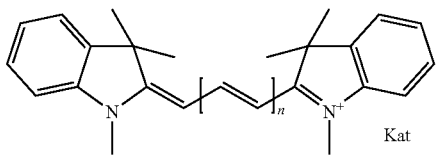

Synthesis of numerous modifications of the core indocyanine structure have been described. Such modifications provided various functionalities, e.g., synthesis of N-isothiocyanato-alkyl- and aromatic-carboxyalkyl-functionalized indocyanines, are described in U.S. Pat. Nos. 5,627,027; 6,048,982; 4,981,977; U.S. Publication No. 2006/0199949; MANK, A. J. G. et al., Visible Diode Laser-Induced Fluorescence Detection in Liquid Chromatography after Precolumn Derivatization of Amines. Anal. Chem. vol. 67, pp. 1742-1748, 1995.

Synthesis of indocyanines containing C-carboxyalkyl groups were described in JP 05-313304; U.S. Publication Nos. 2006/0099638, 2006/0004188; 2002/0077487; 2002/0064794; and U.S. Pat. Nos. 6,977,305 and 6,974,873.

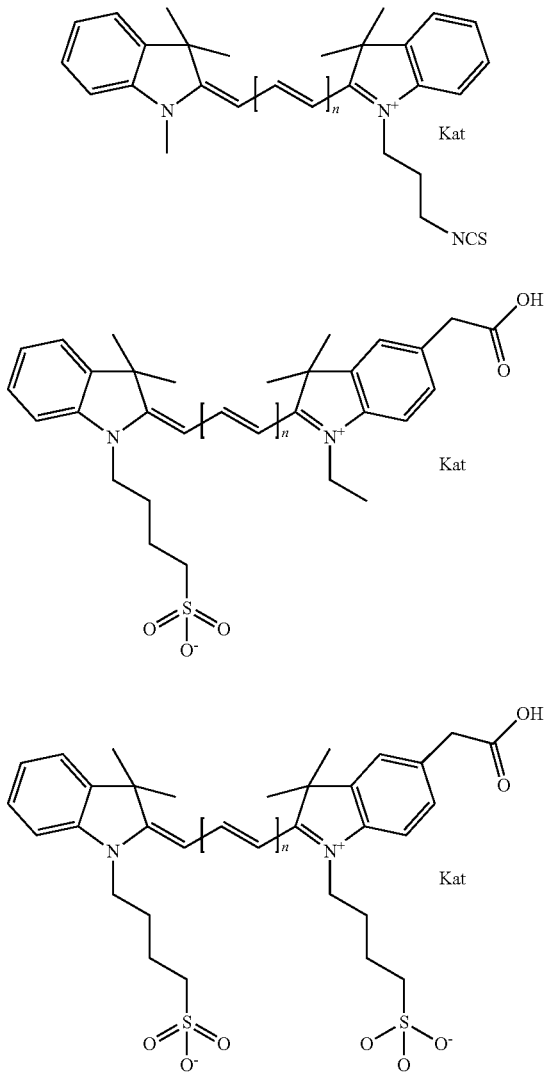

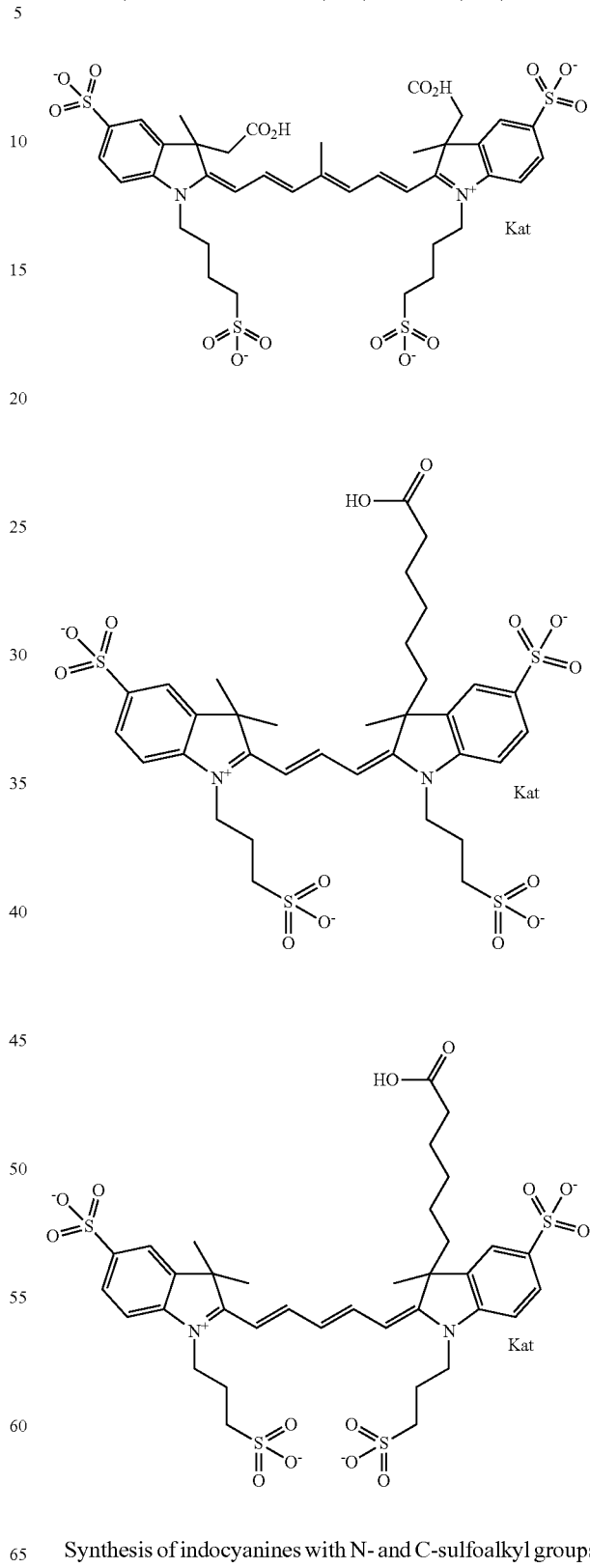

Synthesis of indocyanines with one or two N-carboxyalkyl functionalities were described in U.S. Pat. Nos. 5,268,486; 5,486,616; 5,569,587; 5,569,766, and JP 03217837.

Synthesis of indocyanines with N- and C-sulfoalkyl groups were described in JP 05-313304; WO 2005/044923; and U.S. Publication No. 2007/0203343.

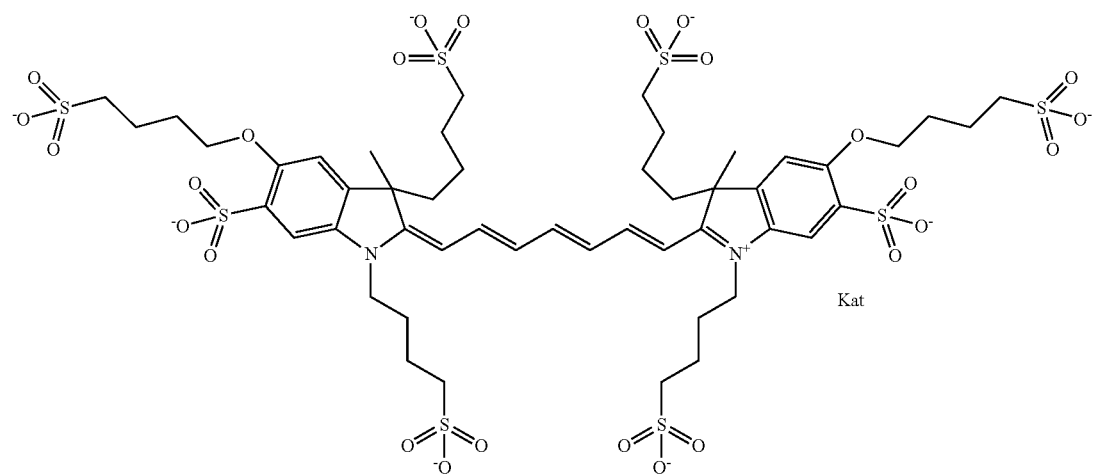
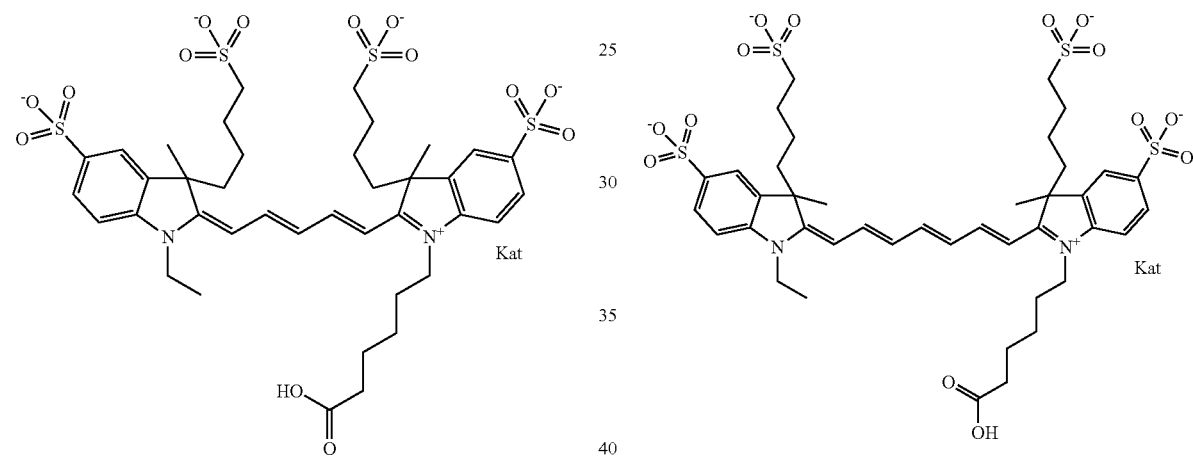
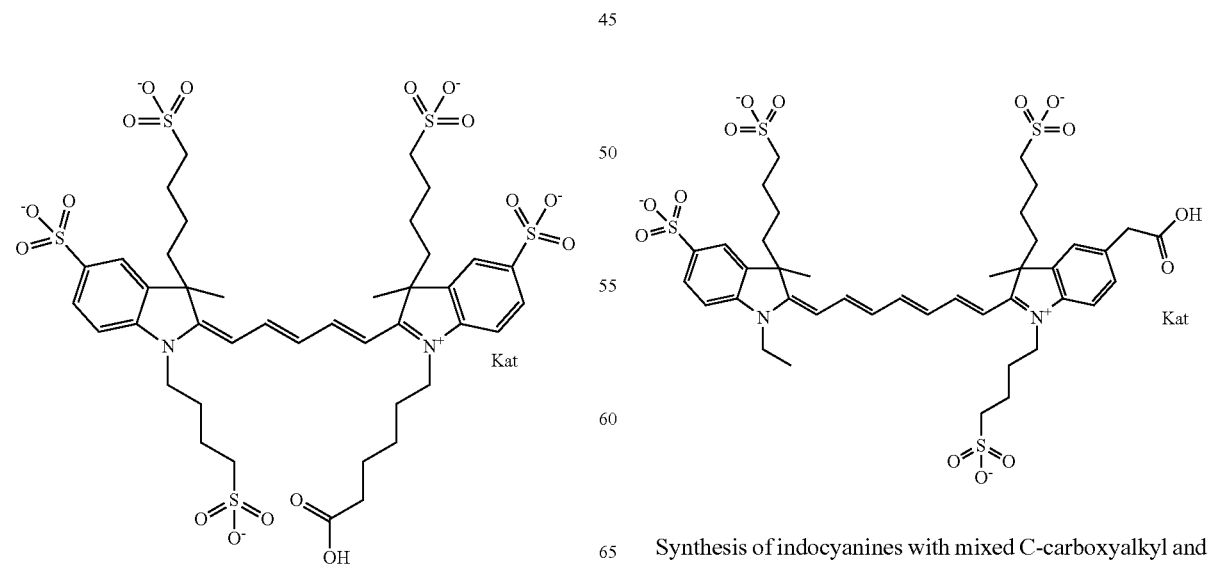
Synthesis of indocyanines with mixed C-carboxyalkyl and C-sulfoalkyl were described in EP 1792949 and U.S. Pat. No. 7,745,640.

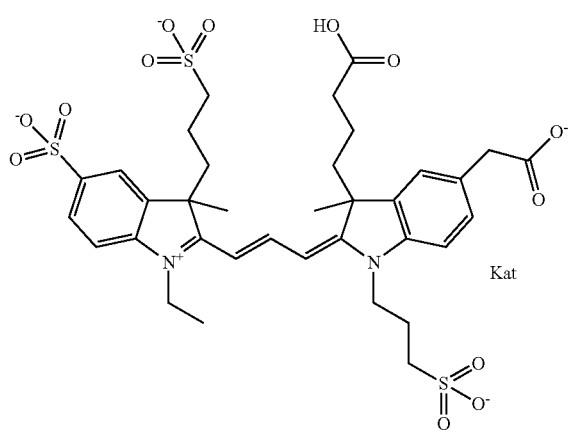
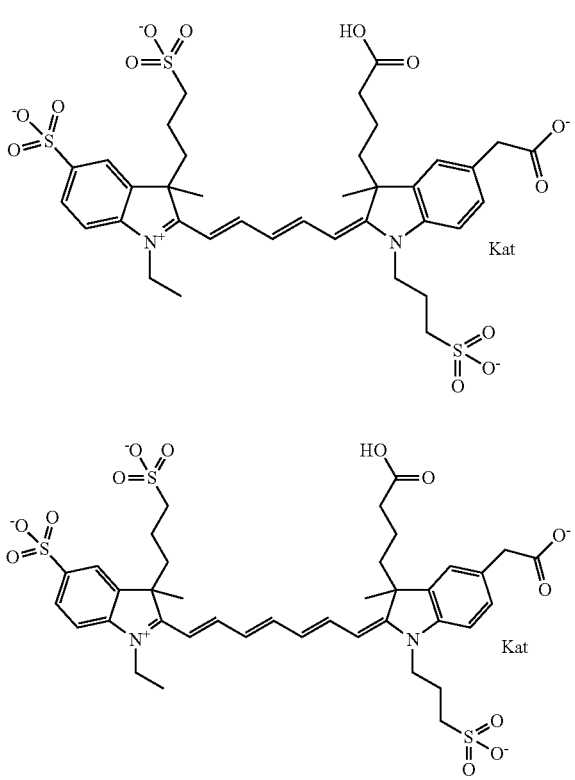
Synthesis of indocyanaines having a PEG-containing N-carboxyalkyl spacer were described in U.S. Pat. No. 6,939,532.
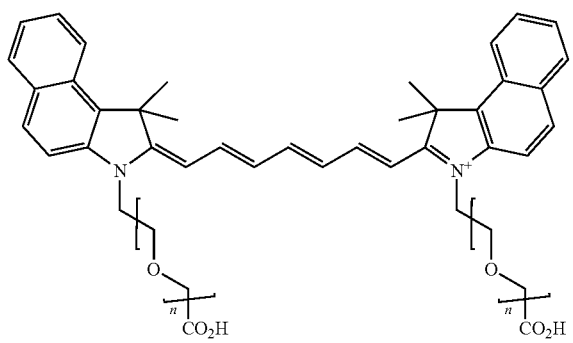
Functionalization of the N-carboxyalkyl with an amino-functionalized PEG-alkyl chain, and N- and C-substituted PEG-alkyl chains, were described in U.S. Publication No. 2009/0305410.
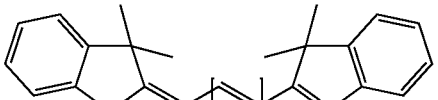
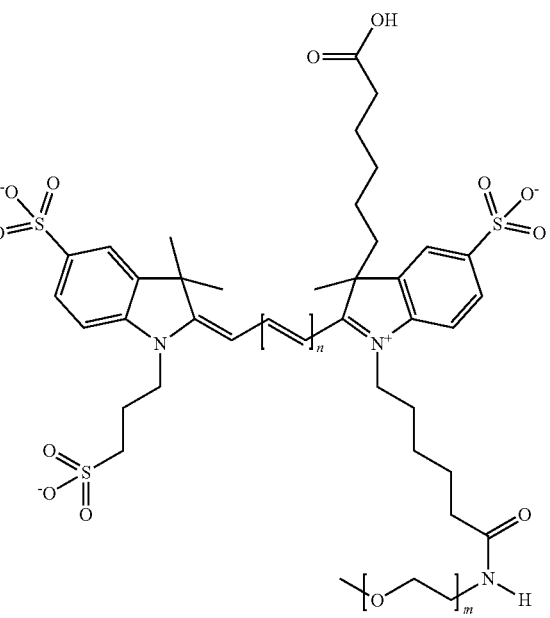
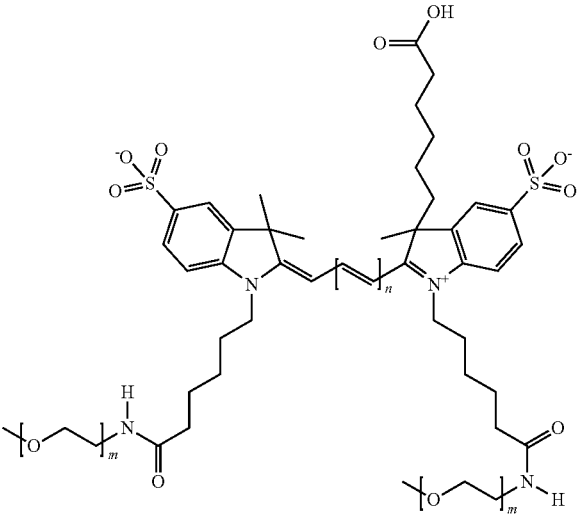

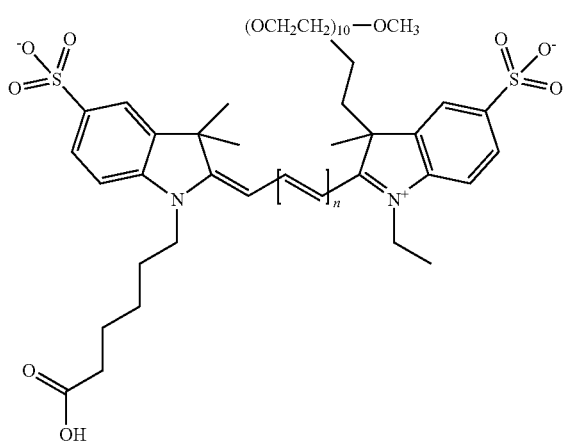

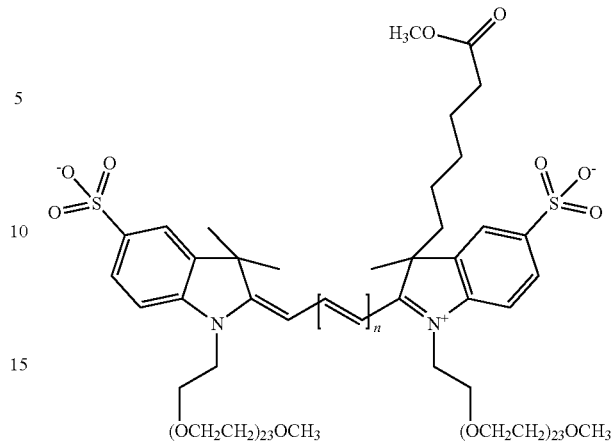

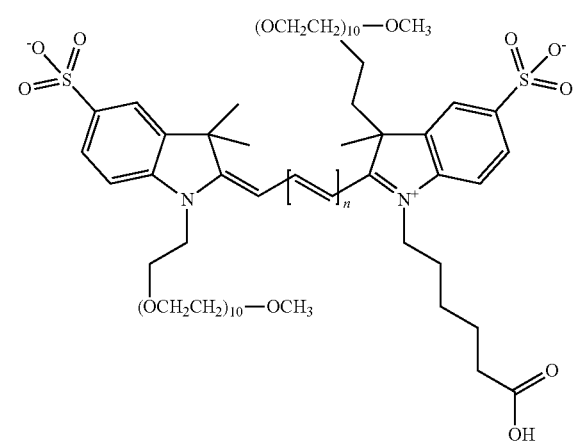

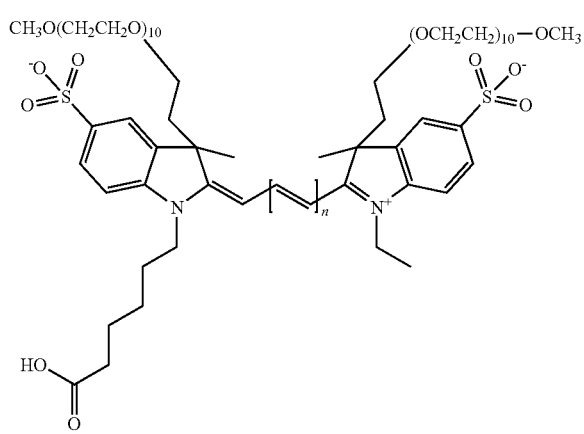

Synthesis of various polymethine bridge substitutions, and other indocyanine functionalizations, are disclosed in Example 1-18, in Strekowski, Heterocyclic Polymethine Dyes: Synthesis, Properties and Applications, (2008) Springer-Verlag, Berlin Heidelberg; Gragg, "Synthesis of Near-Infrared Heptamethine Cyanine Dyes" (2010) Chemistry Theses. Paper 28; Patonay et al. (2004) Noncovalent Labeling of Biomolecules with Red and Near-Infrared Dyes. Molecules 9 (2004) 40-49; and U.S. Pat. No. 7,172,907.

In one embodiment, the compound is synthesized by a condensation reaction, known to one skilled in the art, of the two differently substituted indole heterocycles separated by a (poly)methine linker or bridge, e.g., C1, C3, or C5. Other synthesis methods are possible. As only one example, one of the indole heterocycles is first reacted with the C1, C3, or C5 linker. The 1:1 condensation product is isolated, and then condensed with the second indole heterocycle to result in the cyanine compound. The sequence of reacting the indole heterocycles is irrelevant. Thus, a plurality of differently functionalized, strongly hydrophilic, diastereomeric compounds that differ in total charge and specificity/reactivity of the active groups used for their immobilization, were prepared.

Conjugates of the compounds are prepared by covalently coupling the compounds to a biomolecule using the functional substituent on the N-position of the indole ring. This functional substituent is activated by routine protein chemistry reaction methods known to one skilled in the art. The activated compound may be converted to, without limitation, an N-hydroxysuccinimide (NHS)-ester, an acid fluoride, a tetrafluorophenyl (TFP)- or sulfotetrafluorophenyl (STP)-ester, an iodoacetyl group, a maleimide, a hydrazide, a sulfonyl chloride, a phenylazide. Methods for preparing such compounds are known to one skilled in the art. In one embodiment, the activated substituent is then reacted with an amino group on the biomolecule under conditions to form the linkage. In one embodiment, a non-activated carboxyl group on the N-position of the indole in the compound is coupled to an amine using a carbodimide.

Coupling between the compound and the biomolecule may be performed as follows. The compound is reacted with the biomolecule in an organic or aqueous solution at a pH between pH 5 and pH 12, inclusive. The compound need not be dissolved in an organic solvent, such as dimethyl formamide (DMF) or dimethyl sulfoxide (DMSO) prior to adding the biomolecule. In one embodiment, coupling reaction may be performed in a 100% aqueous solution. In one embodiment, the coupling reaction occurs at room temperature (about 20° C. to about 22° C.).

To form a composition (dye), at least one biocompatible excipient is added to the compound(s), as known to one of ordinary skill in the art. Excipients include but are not limited to buffers, solubility enhancing agents, stabilizing agents, etc.

In one embodiment, a kit for performing an assay method comprises a disclosed compound, and instructions for performing the method using the compound.

The disclosed activated compounds (i.e., the compound modified with a reactive group) are useful to label macromolecules (e.g., antibodies, streptavidin, etc) using methods known to one skilled in the art, e.g., as disclosed in Hermanson, Bioconjugate Techniques, 2nd Ed., London, Elsevier Inc. 2008. The reaction is carried out for one hour to two hours at room temperature (about 20° C. to about 22° C.), and then desalted by dialyzing against several changes of phosphate buffered saline (pH 7.2) or purified by gel filtration to remove the unreacted fluorescent dye. The resulting compound-biomolecule conjugate is useful in applications such as detection of specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibit fluorescent properties. They may be used in optical, including fluorescence optical, qualitative and quantitative determination methods. Examples of such methods include, but are not limited to, microscopy, immunoassays, hybridization methods, chromatographic and electrophoretic methods, fluorescence resonance energy transfer (FRET) systems, high throughput screenings, analysis of receptor-ligand interactions on a microarray, etc.

Compounds of any of the embodiments can be used as dyes for optical labelling of organic or inorganic biomolecules, also referred to as recognition units. Recognition units are molecules having specificity and/or affinity for a specific group of molecules. Examples of recognition units include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein AIG and Protein L, sequences of amino acids or metals that have affinity for each other (e.g., histidine sequences bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormone), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. The ionic interactions between these recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates are useful in optical, including fluorescence optical, qualitative and/or quantitative determination methods to diagnose properties of cells (molecular imaging), in biosensors (point of care measurements), for investigation of the genome, and in miniaturizing technologies. Microscopy, cytometry, cell sorting, fluorescence correlation spectroscopy (FCS), ultra high throughput screening (uHTS), multicolour fluorescence in situ hybridisation (mc-FISH), FRET-systems and microarrays (DNA- and protein chips) are exemplary application fields. As known to one skilled in the art, a microarray, a grid-like arrangement where more than two different molecules are immobilized in a known predefined region on at least one surface, is useful to evaluate receptor ligand interactions. As known to one skilled in the art, a receptor is a naturally occurring or synthetic molecule that exhibits an affinity to a given ligand. Receptors can be used in a pure form or bound to another specie. Receptors can be coupled covalently or noncovalently to a binding partner either directly or indirectly (e.g., through a coupling mediator). Receptor examples include, but are not limited to, agonists and antagonists for cell membrane receptors, toxins and other poisons, viral epitopes, hormone like opiates and steroids, hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. As known to one skilled in the art, a ligand is a molecule that is recognized by a certain receptor. Ligand examples include, but are not limited to, agonists and antagonists for cell membrane receptors, toxins and other poisons, viral epitopes, hormones like opiates and steroids, hormone receptors, peptides, enzymes, enzyme substrates, drugs acting as cofactors, lectins, sugars, oligonucleotides, nucleic acids, oligosaccharides, proteins, antibodies, etc.

In one embodiment, the inventive phosphine compounds and/or conjugates are used as chemoselective, also termed bioorthogonal, chemistry reagents. Because azides are not naturally present in cells and phosphines do not naturally react with azides in cells, adding the inventive phosphines to cells specifically labels only azide-containing cell components with no non-specific labeling. Using metabolic labeling, azide groups, which are the reactive targets of the phosphine-activated fluors, were introduced into proteins or other cellular targets using azide reagents or through in vivo labeling with azide-derivatives of naturally occurring metabolic building blocks.

Metabolic labeling refers to methods in which chemical detection- or affinity-tags are added to biomolecules in vivo using the endogenous synthesis and modification machinery of live cells. Analogs of molecular building blocks (e.g., amino acids, sugars) designed to contain specifically targetable tags that do not interfere with the cellular metabolic machinery provide a mechanism for metabolic labeling, permitting a number of powerful experimental approaches for investigating cellular pathways. Metabolic labeling with bioorthogonal monosaccharides (sugars) that are used by cells to glycosylate proteins and other cell constituents provides a variety of experimental approaches. The effects of drugs or other treatment conditions on total or sugar-specific glycosylation can be measured. When bioorthogonal azidosugar derivatives are supplied to live cells, they are incorporated into glycoproteins by endogenous post-translational modification mechanisms. The azide-tagged molecules are then selectively labeled or conjugated to phosphine-activated molecules.

This specific cellular labeling with phosphines occurs in a two-step process: (1) conjugating a cell protein, carbohydrate, etc. or other biomolecule with an azide group; then (2)

adding the inventive phosphine compound to the azide-containing biomolecule. Staudinger ligation (azide-phosphine) chemistry is a crosslinking technique amenable to in vivo metabolic labeling. Because the azide component of the chemoselective reaction pair is small, it can be supplied to live cells in the form of bioorthogonal molecules that substitute for cellular building blocks used to synthesize proteins or other macromolecules.

Figure 2:
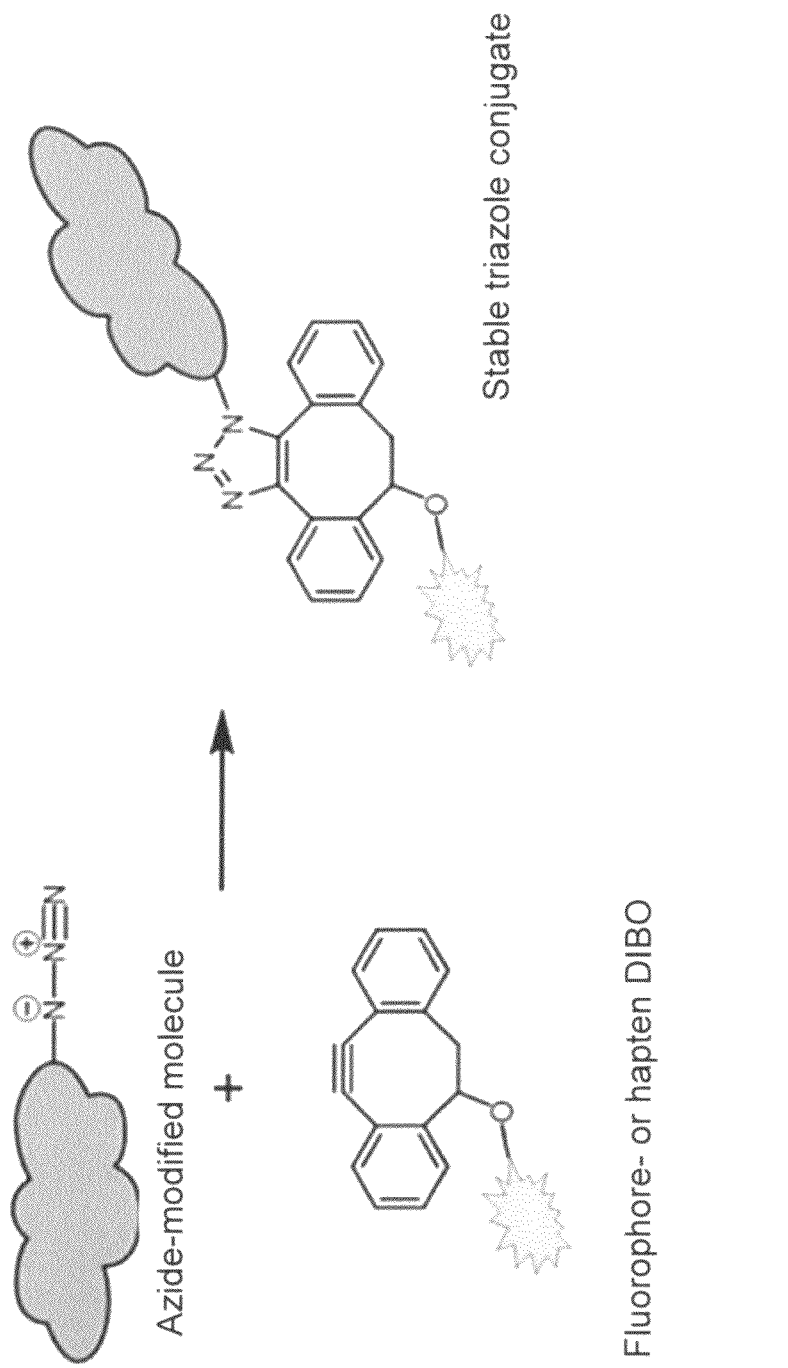
Figure 3:
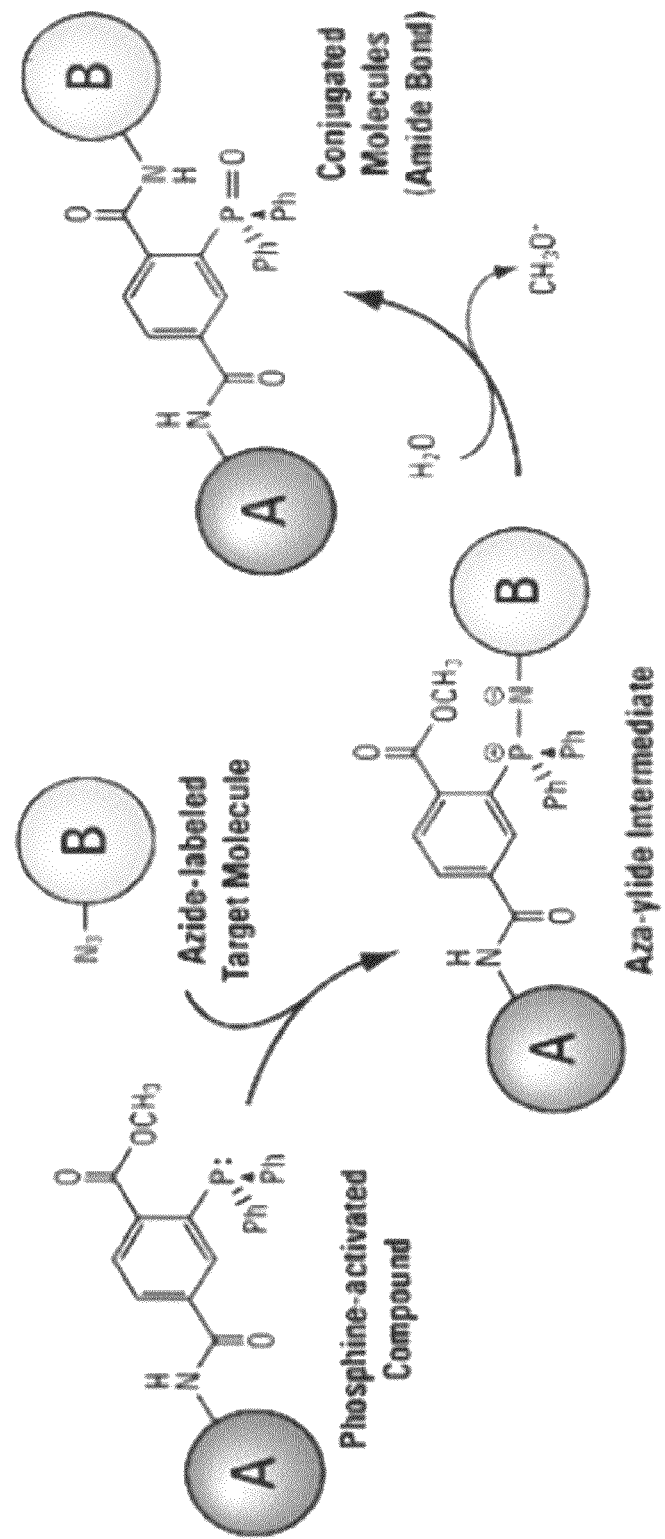

Bioorthogonal chemistry refers to any chemical reaction that can occur inside living systems without interfering with native biochemical processes. The concept of the bioorthogonal reactions have enabled real time study of biomolecules such as glycans, proteins, and lipids in living systems without cellular toxicity. Several chemical ligation strategies have been developed that fulfil bioorthogonality requirements, e.g., the isonitrile-based CLICK-iT® reaction (FIG. 1); the 1,3-dipolar cycloaddition between azides and cyclooctynes, also termed copper-less Click Reaction (FIG. 2) using dibenzocyclooctyne; the Staudinger ligation (FIG. 3); and reaction between nitrones and cyclooctynes, oxime/hydrazone formation from aldehydes and ketones, the tetrazine ligation, and the quadricyclane ligation.

As stated previously, bioorthogonal chemical reactions typically proceed in two steps. First, a cellular substrate or target molecule is modified with a bioorthogonal functional group, also termed a chemical reporter, and introduced to the cell; substrates include metabolites, enzyme inhibitors, antibodies, etc. The functional group is designed so it does not dramatically alter the structure of the substrate, thus not affecting substrate bioactivity. Secondly, a probe containing a complementary functional group is introduced to react with and label the substrate.

Whether a particular labeling chemistry can be used in metabolic labeling depends upon its chemoselectivity (reaction specificity) and metabolic compatibility (i.e., production of bioorthogonal derivatives through metabolism). In this chemoselective ligation strategy, one component of the reaction pair is supplied as a substitute (an analog) of a naturally occurring molecule required for catabolism of the target macromolecules. Bioorthogonal means that the biological function of the molecule is unaffected by the reactive group it contains, i.e., the reactive group is invisible to the biological system. The azide group in the Staudinger reaction pair has this bioorthogonal property. When supplied to cells, synthetic azide-containing analogs of amino acids or sugars are incorporated during protein synthesis or post-translational glycosylation using cellular metabolic or regulatory machinery. Thus, the relevant chemoselective reactive group is added in vivo by metabolic labeling. Alternatively, bioorthogonal derivatives can be incorporated into specific non-protein targets using in vitro enzymatic reactions. Once target molecules are labeled (tagged) with the bioorthogonal group (azide), they can be chemoselectively conjugated or tagged by reaction with the desired phosphine-activated reagent (biotin, fluor, etc.) using the Staudinger reaction. Chemoselective ligation using bioorthogonal derivatives combines the simplicity of metabolically encoded tags with specific labeling and the versatility of small-molecule probes.

The Staudinger ligation includes an ester group ortho to the phosphorus atom on one of the aryl rings to direct the aza-ylide to outcompete immediate hydrolysis by positioning the ester to increase local concentration. The initial nucleophilic attack on the azide is the rate-limiting step. The ylide reacts with the electrophilic ester trap through intramolecular cyclization to form a five-membered ring. This ring undergoes hydrolysis to form a stable amide bond. The azide group is particularly bioorthogonal because it is metabolically stable, extremely small rendering it favorable for cell permeability and avoiding perturbations, and not naturally existing in cells, thus having no competing biological side reactions. Staudinger ligation requires fewer harmful additives than other chemoselective ligation chemistries developed for use with biological samples. Although azide-alkyne ("click") chemistry uses the same azide component as the azide-phosphine (Staudinger) chemistry, it requires special copper-containing reaction buffers that have damaging effects on cellular components.

Figure 4:
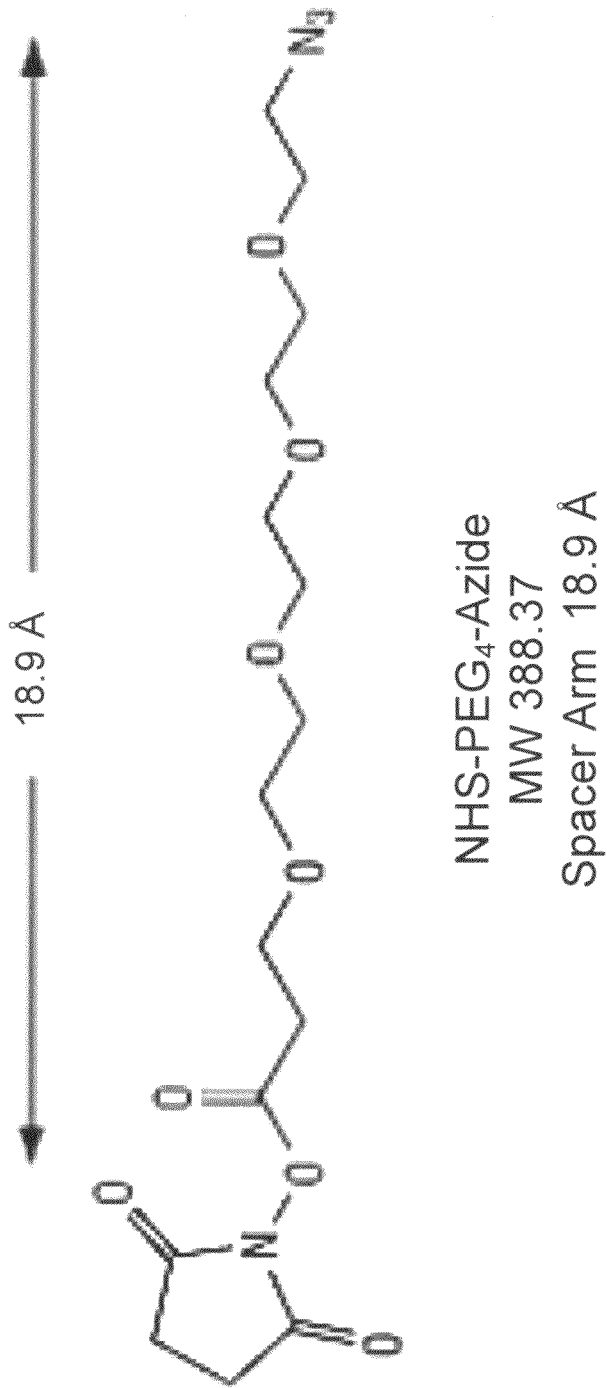
FIG. 4 shows one embodiment of a heterobifunctional linking moiety.

In one embodiment, the inventive phosphine-containing compounds are conjugated by bioorthogonal chemistry using the Staudinger ligation in which the inventive compound is conjugated with a biomolecule of interest, such as an antibody or a sugar moiety. In one embodiment, the conjugation reaction reacts a heterobifunctional linking moiety with a biomolecule of interest, resulting in a free azide group. The free azide group is then reacted with a phosphine on the compound to form a biomolecule-linker-phosphine compound conjugate. In one embodiment, the heterobifunctional linking moiety contains at one end a first group that is reactive with an amine, such as an NHS ester, and at the other end a second azide group, and a polyethylene glycol between the first and second groups. In one example, the polyethylene glycol is a $PEG_4$ group, shown in FIG. 4.

The inventive compounds are soluble; they readily dissolve in water-miscible solvents (e.g., DMSO) for subsequent dilution in aqueous reaction mixtures with cell lysates and other biological samples. The inventive compounds' reaction chemistry occurs effectively in simple buffer conditions, they do not require accessory reagents such as copper or reducing agents, and they do not interfere with fluorescence applications. The inventive compounds are chemoselective in that the phosphine reactive group is specific in biological samples for azide-tagged molecules, ensuring that fluorescent labeling is specific. The inventive compounds exhibit high-performance fluorescence, e.g., 550 Compound 1-phosphine and 650 Compound 1-phosphine are intense, highly stable fluorophores for fluorescent detection.

The following examples illustrate the utility of the invention but do not limit the claim scope.

EXAMPLE 1

Synthesis of 4-methyl-5-oxohexane sulfonic acid used to synthesize Example 2 compound 2,3-dimethyl-3-(3-sulfopropyl)-3H-indole-5-sulfonic acid di-potassium salt

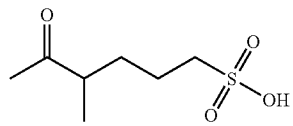

Sodium hydride (2.1 g, 80 wt %=69 mmol) was slurried in 10 ml dry THF. The suspension was cooled to 0° C. and a solution of ethyl-2-methylacetoacetate (10 g, 69 mmol) in 10 ml dry THF was added dropwise. The solution was stirred at room temperature for one h. A solution of 1,3-propanesultone (8.42 g, 69 mmol) in 10 ml dry THF was added dropwise. Once the addition was complete, the solution was stirred for two h at 40° C. The solution was evaporated to dryness. The residue was dissolved in 100 ml water. The aqueous solution was extracted twice with ethylacetate, then 100 ml concentrated HCl was added and the solution was refluxed for two hours. The solvent was evaporated in vacuum. The residue was purified by column chromatography (silica, methanol/dichloromethane) to give 4-methyl-5-oxohexane sulfonic acid. Yield 10 g; MS (ESI−): 193.2 [M]−

EXAMPLE 2

Synthesis of 2,3-dimethyl-3-(3-sulfopropyl)-3H-indole-5-sulfonic acid di-potassium salt used to synthesize Example 3 compound 1-(2-methoxy-ethyl)-2,3-dimethyl-5-sulfo-3-(3-sulfo-propyl)-3H-indolium and Example 4 compound 1-[2-(2-methoxy-ethoxy)-ethyl]-2,3-dimethyl-5-sulfo-3-(3-sulfo-propyl)-3H-indolium and Example 5 compound 1-{2-[2-(2-methoxy-ethoxy)-ethoxy]-ethyl}-2,3-dimethyl-5-sulfo-3-(3-sulfo-propyl)-3H-indolium and Example 6 compound 1-(5-carboxypentyl)-2,3-dimethyl-5-sulfo-3-(3-sulfopropyl)-3H-indolium

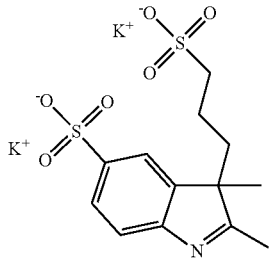

Ten g (51 mmol) 4-hydrazino-benzene sulfonic acid and 9.85 g (51 mmol) 4-methyl-5-oxohexane sulfonic acid were dissolved in 50 ml acetic acid. The solution was heated at 140° C. for four h. The solvent was evaporated in vacuum. The oily residue was dissolved in 20 ml methanol, then 50 ml of a saturated solution of KOH in 2-propanol was added to yield a yellow precipitate. The solid was filtered off and dried in vacuum. Yield 11 g, MS (ESI−): 172.5 [M]$^{2-}$

EXAMPLE 3

Synthesis of 1-(2-methoxy-ethyl)-2,3-dimethyl-5-sulfo-3-(3-sulfo-propyl)-3H-indolium used to synthesize 550, 650, 755 Compound 1

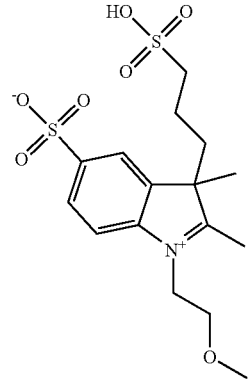

A mixture of 5 g (12.4 mmol) 2,3-dimethyl-3-(3-sulfopropyl)-3H-indole-5-sulfonic acid dipotassium salt and 5.89 g (25.6 mmol) 2-methoxyethyl-p-toluene sulfonate was heated under argon for 24 h. The residue was purified by column chromatography (reversed phase silica, methanol/water, TFA). Yield 2.3 g, MS (ESI−): 404.1 [M-H]−

EXAMPLE 4

Synthesis of 1-[2-(2-methoxy-ethoxy)-ethyl]-2,3-dimethyl-5-sulfo-3-(3-sulfo-propyl)-3H-indolium used to synthesize 550, 650, 755 Compound 2

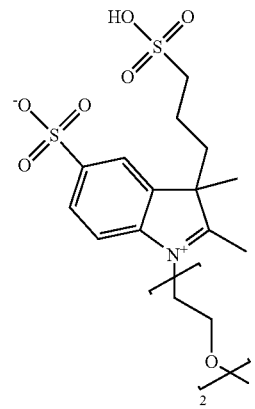

A mixture of 5 g (12.4 mmol) 2,3-dimethyl-3-(3-sulfopropyl)-3H-indole-5-sulfonic acid dipotassium salt and 7.1 g (25.6 mmol) [2-(2-methoxyethoxy)ethoxy]-p-toluene sulfonate was heated under argon for 24 h. The residue was purified by column chromatography (reversed phase silica, methanol/water, TFA). Yield 2.0 g. MS (ESI−): 448.2 [M-H]−

EXAMPLE 5

Synthesis of 1-{2-[2-(2-methoxy-ethoxy)-ethoxy]-ethyl}-2,3-dimethyl-5-sulfo-3-(3-sulfo-propyl)-3H-indolium used to synthesize 550, 650, 755 Compound 3

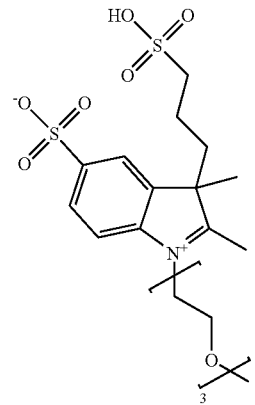

A mixture of 5 g (12.8 mmol) 2,3-dimethyl-3-(3-sulfopropyl)-3H-indole-5-sulfonic acid dipotassium salt and 8.14 g (25.6 mmol) [2-[2-(2-methoxyethoxy)ethoxy]ethoxy]p-toluene sulfonate was heated under argon for 24 h. The residue was purified by column chromatography (reversed phase silica, methanol/water, TFA). Yield 1.9 g, MS (ESI−): 492.1 [M-H]−

EXAMPLE 6

Synthesis of 1-(5-carboxypentyl)-2,3-dimethyl-5-sulfo-3-(3-sulfopropyl)-3H-indolium used to synthesize Example 7 compound 1-(5-carboxypentyl)-3-methyl-2-((E)-2-phenylamino-vinyl)-5-sulfo-3-(3-sulfo-propyl)-3H-indolium and Example 8 compound 1-(5-carboxypentyl)-3-methyl-2-((1E,3E)-4-phenylamino-buta-1,3-dienyl)-5-sulfo-3-(3-sulfopropyl)-3H-indolium and Example 9 compound 1-(5-carboxypentyl)-3-methyl-2-((1E,3E,5E)-6-phenylamino-hexa-1,3,5-trienyl)-5-sulfo-3-(3-sulfopropyl)-3H-indolium

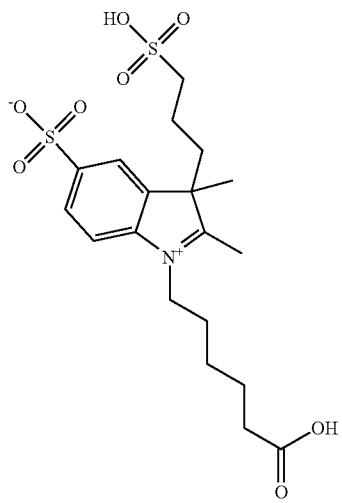

Both 5 g (15.7 mmol) 6-hydrazino-naphthalene-1,3-disulfonic acid and 4.93 g (25 mmol) 4-methyl-5-oxohexane sulfonic acid were dissolved in 50 ml acetic acid. The solution was heated at 140° C. for four hours. The solvent was evaporated in a vacuum. The oily residue was dissolved in 20 ml methanol, then 50 ml of a saturated solution of KOH in 2-propanol was added to yield a yellow precipitate. The solid was filtered off and dried in vacuum. Yield 4.1 g, MS (ESI-): 158.2 $[M]^{3-}$

EXAMPLE 7

Synthesis of 1-(5-carboxypentyl)-3-methyl-2-((E)-2-phenylamino-vinyl)-5-sulfo-3-(3-sulfo-propyl)-3H-indolium used to synthesize 550 Compounds

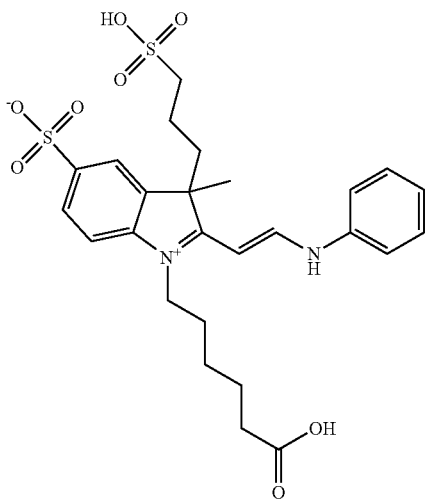

A combination of 0.92 g (2 mmol) 1-(5-carboxypentyl)-2,3-dimethyl-5-sulfo-3-(3-sulfopropyl)-3H-indolium and 0.43 g (2.2 mmol) N,N'-diphenylformamidine was dissolved in 20 ml methanol and stirred for 4 h under reflux. The solvent was removed under vacuum. The residue was washed carefully with ethyl acetate. A dark yellow solid was obtained which was processed without further purification.

MS (ESI-): 563.1 $[M-H]^-$

EXAMPLE 8

Synthesis of 1-(5-carboxypentyl)-3-methyl-2-((1E,3E)-4-phenylamino-buta-1,3-dienyl)-5-sulfo-3-(3-sulfopropyl)-3H-indolium used to synthesize 650 Compounds

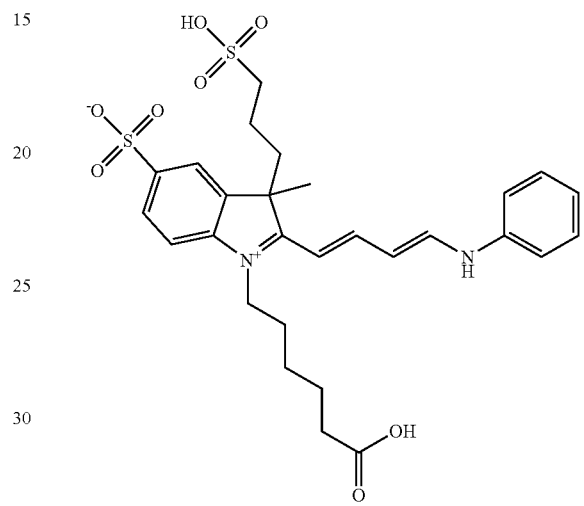

A combination of 0.92 g (2 mmol) 1-(5-carboxypentyl)-2,3-dimethyl-5-sulfo-3-(3-sulfopropyl)-3H-indolium and 0.57 g (2.2 mmol) malonaldehyde-bisphenylimine-hydrochloride was dissolved in 10 ml acetic acid and 10 ml acetic anhydride and stirred for four h at 120° C. The solvent was removed under vacuum. The residue was washed carefully with ethyl acetate. A dark brown solid was obtained which was processed without further purification. MS (ESI-): 589.2 $[M-H]^-$

EXAMPLE 9

Synthesis of 1-(5-carboxypentyl)-3-methyl-2-((1E,3E,5E)-6-phenylamino-hexa-1,3,5-trienyl)-5-sulfo-3-(3-sulfopropyl)-3H-indolium used to synthesize 755 Compounds

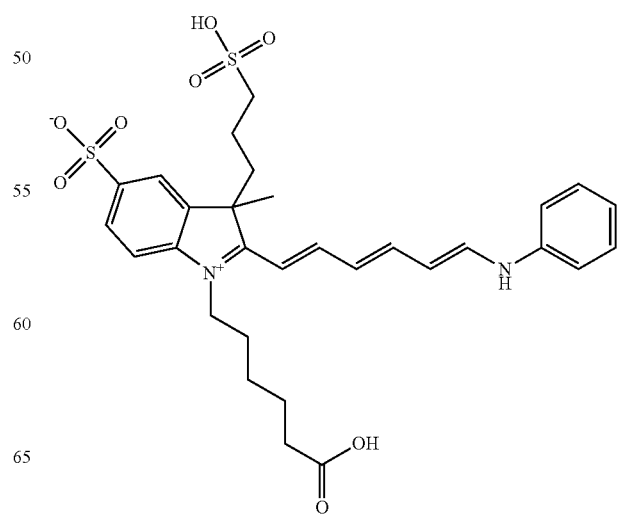

A combination of 0.92 g (2 mmol) 1-(5-carboxypentyl)-2,3-dimethyl-5-sulfo-3-(3-sulfopropyl)-3H-indolium and 0.63 g (2.2 mmol) glutacondianil-hydrochloride was dissolved in 10 ml acetic acid and 10 ml acetic anhydride and stirred for four h at 120° C. The solvent was removed under vacuum. The residue was washed carefully with ethyl acetate. A dark solid was obtained which was processed without further purification. MS (ESI–): 615.2 [M-H]$^-$

EXAMPLE 10

Synthesis of 550 Compound 1 2-{(E)-3-[1-(5-carboxypentyl)-3-methyl-5-sulfo-3-(3-sulfopropyl)-1,3-dihydro-indol-(2E)-ylidene]-propenyl}-1-(2-methoxy-ethyl)-3-methyl-5-sulfo-3-(3-sulfo-propyl)-3H-indolium tri sodium salt

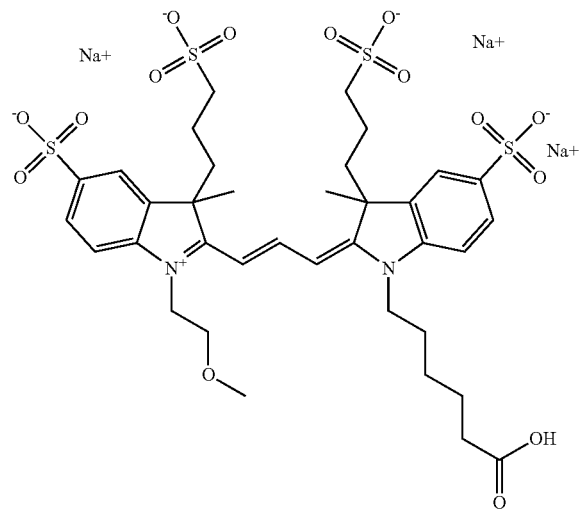

Five hundred sixty-four mg (1 mmol) 1-(5-carboxypentyl)-3-methyl-2-((E)-2-phenylamino-vinyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1), followed by 200 mg sodium acetate. The solution was stirred under reflux for 15 min. After cooling to room temperature, 20 ml diethylether was added. The resulting precipitate (mixture of the diastereomers 550 Compound 1 (isomer 1) and 550 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (550 Compound 1 (isomer 1)). The diastereomer that eluted second from the column was termed diastereomer 2 (550 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 550 Compound 1 (isomer 1) and 550 Compound 1 (isomer 2)) were dried in high vacuum.

550 Compound 1 (Isomer 1):
  yield: 12%
  UV-vis (PBS): λmax=557 nm, λem=572 nm
  MS (ESI–) [M/z]: 291.2 [M]$^{3-}$; 448.3 [M+Na]$^{2-}$
550 Compound 1 (Isomer 2):
  yield: 23%
  UV-vis (PBS): λmax=557 nm, λem=572 nm
  MS (ESI–) [M/z]: 291.1 [M]$^{3-}$; 448.2 [M+Na]$^{2-}$

EXAMPLE 11

Synthesis of 550 Compound 2 2-{(E)-3-[1-(5-carboxypentyl)-3-methyl-5-sulfo-3-(3-sulfopropyl)-1,3-dihydro-indol-(2E)-ylidene]-propenyl}-1-[2-(2-methoxy-ethoxy)-ethyl]-3-methyl-5-sulfo-3-(3-sulfo-propyl)-3H-indolium tri sodium salt

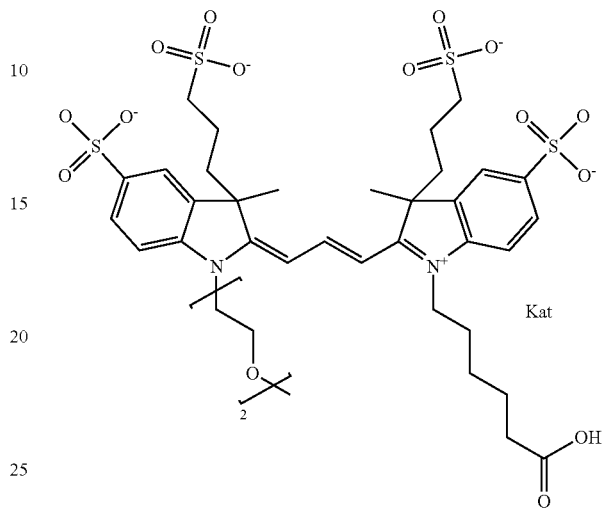

Both 1 mmol 1-(5-carboxypentyl)-3-methyl-2-((E)-2-phenylamino-vinyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 compound 2 and 550-2 compound 2) was extracted by suction, washed with ether and dried.

The residue was purified by column chromatography (RP-18, acetonitrile/water and concentrated HCl), thereby separating the diastereomers from each other, as described in Example 10.

EXAMPLE 12

Synthesis of 550 Compound 3 2-{(E)-3-[1-(5-carboxypentyl)-3-methyl-5-sulfo-3-(3-sulfopropyl)-1,3-dihydro-indol-(2E)-ylidene]-propenyl}-1-{2-[2-(2-methoxy-ethoxy)-ethoxy]-ethyl}-3-methyl-5-sulfo-3-(3-sulfo-propyl)-3H-indolium tri sodium salt

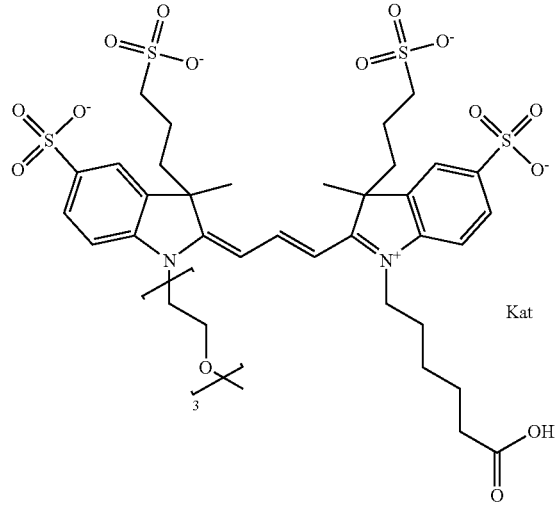

One mmol 1-(5-carboxypentyl)-3-methyl-2-((E)-2-phenylamino-vinyl)-5-sulfo-3-(3-sulfopropyl)-3H-indolium and 1 mmol 1-{2-[2-(2-methoxy-ethoxy)-ethoxy]-ethyl}-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 compound 2 and 550-2 compound 2) was extracted by suction, washed with ether and dried.

The residue was purified by column chromatography (RP-18, acetonitrile/water and concentrated HCl), thereby separating the diastereomers from each other, as described in Example 10.

column, acetonitrile/water. The corresponding fractions were pooled and the solvent was removed by distillation. The two products (diastereomers 650 Compound 1 (isomer 1) and 650 Compound 1 (isomer 2)) were dried in high vacuum.

650 Compound 1 (Isomer 1):

yield: 11%

UV-vis (PBS): λmax=654 nm, λem=672 nm

MS (ESI−) [M/z]: 299.7 [M]$^{3-}$; 461.0[M+Na]$^{2-}$

650 Compound 1 (Isomer 2):

yield: 24%

UV-vis (PBS): λmax=654 nm, λem=672 nm

MS (ESI−) [M/z]: 299.6 [M]$^{3-}$; 461.1 [M+Na]$^{2-}$

EXAMPLE 13

650 Compound 1 Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-(2-methoxy-ethyl)-3-methyl-5-sulfo-3-(3-sulfopropyl)-3H-indolium tri sodium salt

EXAMPLE 14

650 Compound 2 Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-[2-(2-methoxy-ethoxy)-ethyl]-3-methyl-5-sulfo-3-(3-sulfopropyl)-3H-indolium tri sodium salt

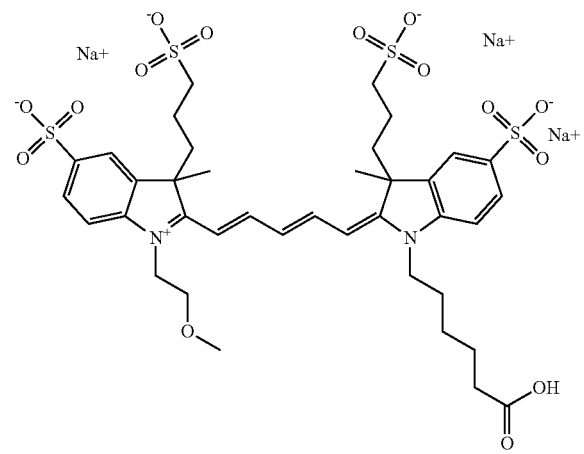

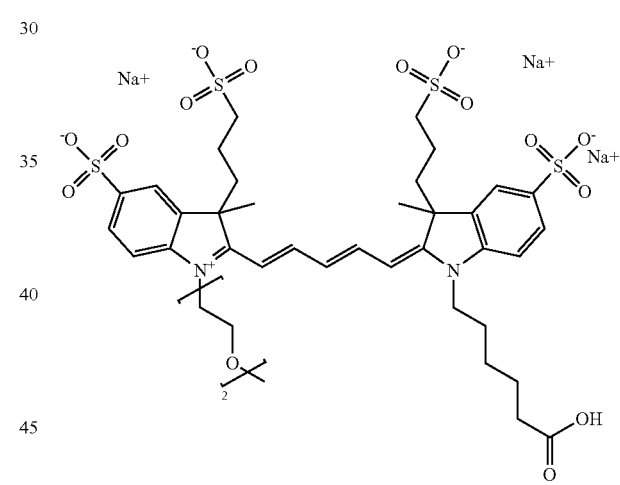

Both 90 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 650 Compound 1 (isomer 1) and 650 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (650 Compound 1 (isomer 1)). The diastereomer that eluted second from the column was termed diastereomer 2 (650 Compound 1 (isomer 2)). The diastereomers were separated, followed by neutralization and evaporation. Purification of the single diastereomeric compound was completed on a RP-18

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 449 mg (1 mmol) 1-[2-(2-methoxy-ethoxy)-ethyl]-2,3-dimethyl-5-sulfo-3-(3-sulfopropyl)-3H-indolium were dissolved in 20 ml of acetic acid/acetic anhydride (1/1) followed by the addition of 200 mg of sodium acetate. The synthesis and work-up were carried out according to Example 13.

650-1 Compound 2:

yield: 11%

UV-vis (PBS): λmax=654 nm, λem=672 nm

MS (ESI−) [M/z]: 314.4 [M]$^{3-}$; 483.0[M+Na]$^{2-}$ 650-2 Compound 2:

yield: 16%

UV-vis (PBS): λmax=654 nm, λem=672 nm

MS (ESI−) [M/z]: 314.5 [M]$^{3-}$; 483.1[M+Na]$^{2-}$

EXAMPLE 15

650 Compound 3 Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-{2-[2-(2-methoxy-ethoxy)-ethoxy]-ethyl}-3-methyl-5-sulfo-3-(3-sulfopropyl)-3H-indolium tri sodium salt—650 compound 3

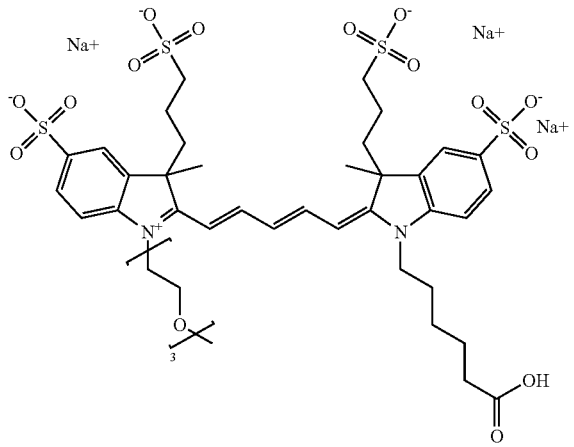

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 493 mg (1 mmol) 1-{2-[2-(2-methoxy-ethoxy)-ethoxy]-ethyl}-2,3-dimethyl-5-sulfo-3-(3-sulfopropyl)-3H-indolium were dissolved in 20 ml acetic acid/acetic anhydride (1/1) followed by the addition of 200 mg sodium acetate. The synthesis and work-up were carried out according to Example 13.

650-1 Compound 3:
  yield: 10%
  UV-vis (PBS): λmax=654 nm, λem=672 nm
  MS (ESI−) [M/z]: 329.2 $[M]^{3-}$; 505.0 $[M+Na]^{2-}$ 650-2 Compound 3:
  yield: 23%
  UV-vis (PBS): λmax=654 nm, λem=672 nm
  MS (ESI−) [M/z]: 329.1 $[M]^{3-}$; 505.1 $[M+Na]^{2-}$

EXAMPLE 16

Synthesis of 755 Compound 1 2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethyl)-3-methyl-5-sulfo-3-(3-sulfopropyl)-3H-indolium tri sodium salt

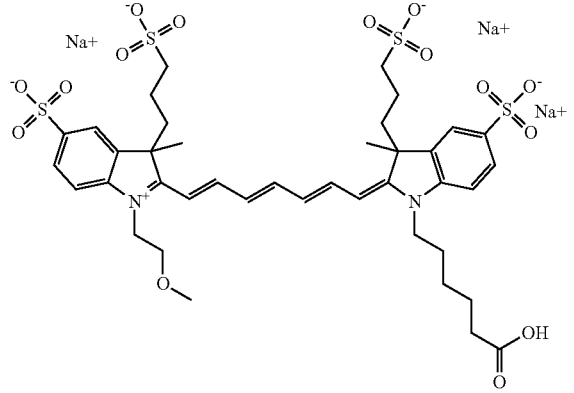

Six hundred and sixteen mg (1 mmol) 1-(5-Carboxypentyl)-3-methyl-2-((1E,3E,5E)-6-phenylamino-hexa-1,3,5-trienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 755 Compound 1 (isomer 1) and 755 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (755 Compound 1 (isomer 1)). The diastereomer that eluted second from the column was termed diastereomer 2 (755 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 755 Compound 1 (isomer 1) and 755 Compound 1 (isomer 2)) were dried in high vacuum.

755 Compound 1 (Isomer 1):
  yield: 8%
  UV-vis (PBS): $\lambda_{max}$=752 nm; $\lambda_{em}$=778 nm
  MS (ESI−) [M/z]: 308.4 $[M]^{3-}$; 474.2$[M+Na]^{2-}$ 755 Compound 1 (Isomer 2):
  yield: 16%
  UV-vis (PBS): $\lambda_{max}$=752 nm; $\lambda_{em}$=778 nm
  MS (ESI−) [M/z]: 308.4$[M]^{3-}$; 474.2 $[M+Na]^{2-}$.

EXAMPLE 17

Synthesis of 755 Compound 2 2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethoxy)-3-methyl-5-sulfo-3-(3-sulfopropyl)-3H-indolium

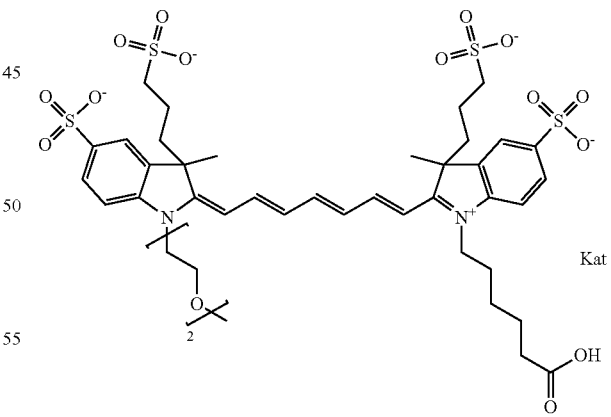

Both 1 mmol 1-(5-carboxypentyl)-3-methyl-2-((1E,3E,5E)-6-phenylamino-hexa-1,3,5-trienyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 2 (isomer 1) and 755 compound 2 (isomer 2)) was extracted by suction, washed with ether, and dried. The residue is purified by column chromatography (RP-18, acetonitrile/water and concentrated HCl), thereby separating the diastereomers from each other, as described in Example 16.

EXAMPLE 18

Synthesis of 755 Compound 3 2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-{2-[2-(2-methoxy-ethoxy)-ethoxy]-ethyl}-3-methyl-5-sulfo-3-(3-sulfopropyl)-3H-indolium

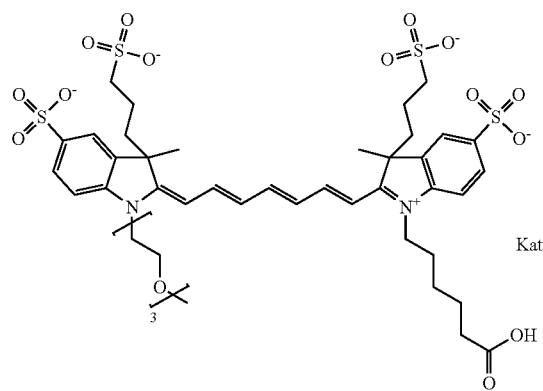

Both 1 mmol 1-(5-carboxypentyl)-3-methyl-2-((1E,3E,5E)-6-phenylamino-hexa-1,3,5-trienyl)-5-sulfo-3-(3-sulfopropyl)-3H-indolium and 1 mmol 1-{2-[2-(2-methoxy-ethoxy)-ethoxy]-ethyl}-2,3-dimethyl-5-sulfo-3-(3-sulfopropyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 3 (isomer 1) and 755 compound 3 (isomer 2)) was extracted by suction, washed with ether and dried. The residue is purified by column chromatography (RP-18, acetonitrile/water and concentrated HCl), thereby separating the diastereomers from each other, as described in Example 16.

EXAMPLE 19

Synthesis of 650 Compound 1-phosphine

Sixty (60) mg (62 µmol) of Compound 1 were dissolved in a mixture of 3 ml DMF and 300 µl water. After cooling to 0° C., 19 mg (62 µmol) TSTU and 11 µl (62 µmol) diisopropylethylamine were added. The reaction mixture was stirred for one hour at 0° C. After warming to room temperature, 82 mg (620 µmol) of ethylenediamine dihydrochloride and 53 µl diisopropylethylamine (310 µmol) were added. The reaction mixture was stirred for two hours. The solvent was then evaporated in vacuum. The residue was purified by HPLC chromatography. Yield: 50 mg of Compound 1—aminomodified.

Fifty (50) mg (50.5 µmol) of Compound 1—aminomodified were dissolved in 3 ml DMF, 23 mg (50.5 µmol) of phosphine-reagent-NHS-ester (Pierce) and 26 µl (150 µmol) diisopropylethylamine were added. The reaction mixture was stirred for two hours at room temperature. The solvent was removed under vacuum and the residue was purified by HPLC chromatography. Yield: 40 mg

EXAMPLE 20

Figure 5:
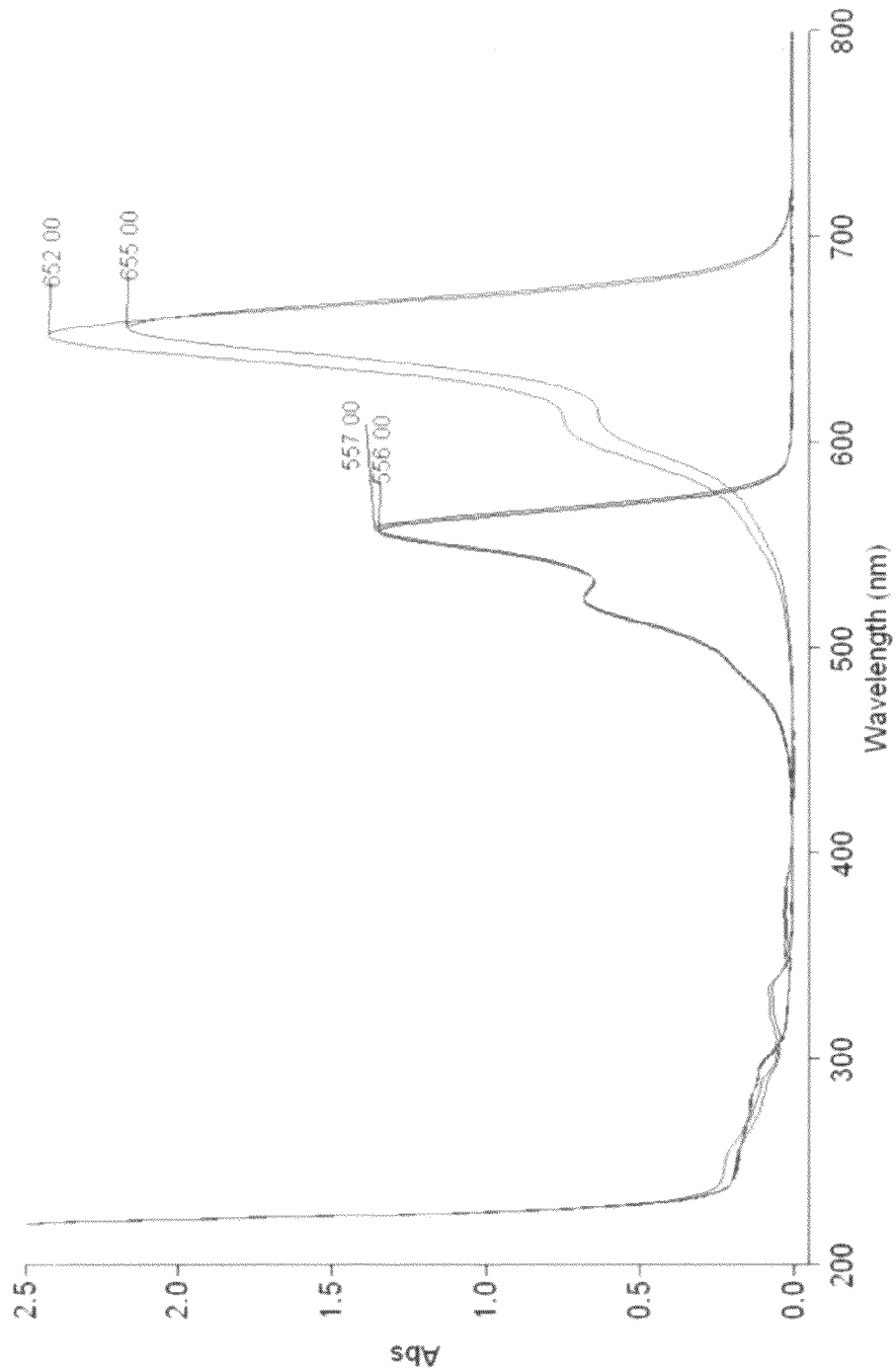
FIG. 5 shows absorbance of various phosphine-containing compounds.

Absorption profiles for inventive and commercial compounds were determined (FIG. 5) where DyLight 549-phosphine (blue), 550 Compound 1-phosphine (purple), DyLight 649-phosphine (red), and 650 Compound 1-phosphine (green) showed similar profiles in their respective pairs (baseline (100% transmission)). Maximum absorbance of 650 Compound 1-phosphine was shifted 3 nm compared to DyLight 649-phosphine.

Figure 6:
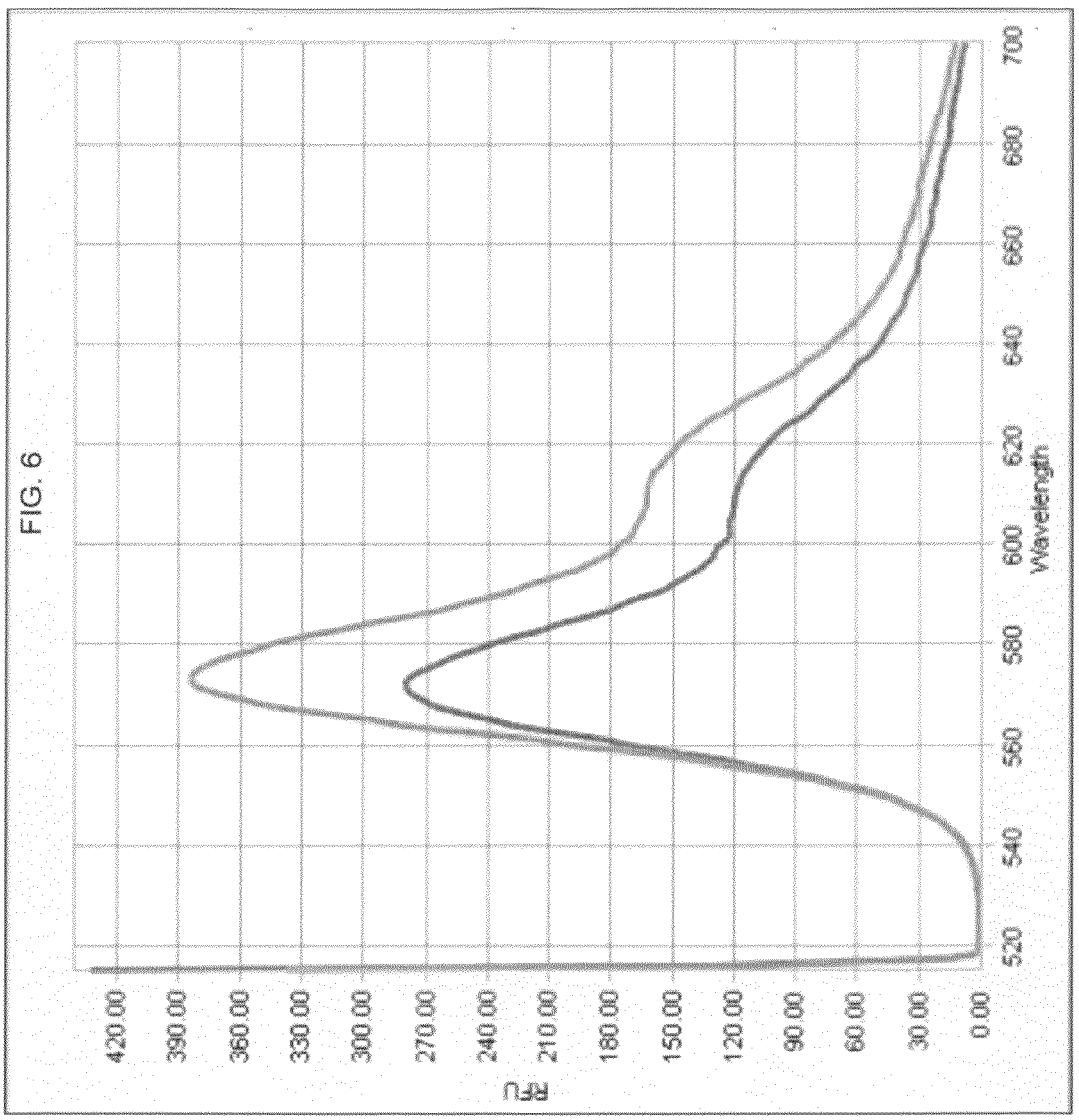
FIG. 6 shows relative fluorescence units (RFU) for various phosphine-containing compounds.
Figure 7:
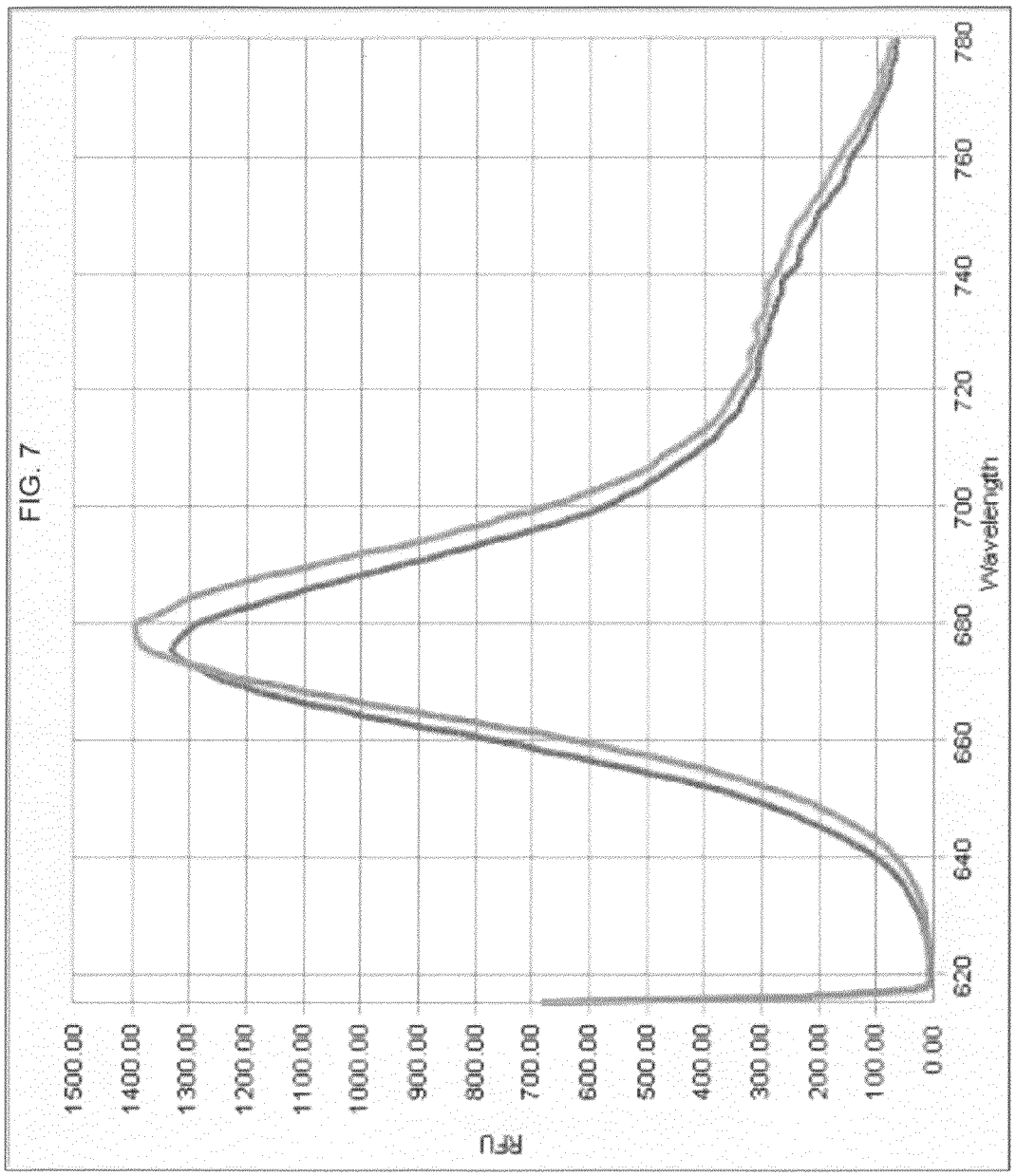
FIG. 7 shows RFU for various phosphine-containing compounds.

Fluorescence intensity was measured for DyLight 549-phosphine (blue) and 550 Compound 1-phosphine (green) (FIG. 6) at an excitation/emission of 560 nm/575 nm and 562 nm/576 nm, respectively; and for DyLight 649-phosphine (blue) and 650 Compound 1-phosphine (green) (FIG. 7) at an excitation/emission of 645 nm/672 nm and 646 nm/674 nm, respectively. The fluorescence intensities for the inventive compounds were similar to their respective counterpart, and maximum fluorescence for 650 Compound 1-phosphine was shifted 3 nm compared to DyLight 649-phosphine. In addition, the inventive phosphine-containing compounds exhibited solubility in dimethylsulfoxide (DMSO) at 10 mM.

EXAMPLE 21

Labeling efficiency of various inventive compounds was examined. Goat anti-Rabbit (GAR) antibodies were conjugated with NHS-PEG$_4$-azide at a 10× molar ratio. Inventive and commercial compounds, each as the phosphine, were conjugated to azide-PEG$_4$-GAR goat anti-rabbit (GAR) for three hours at 37° C. at a 10× molar ratio. Fluorescence Intensity and functional performance of the resulting compound-PEG$_4$-GAR conjugates were determined.

Figure 8:
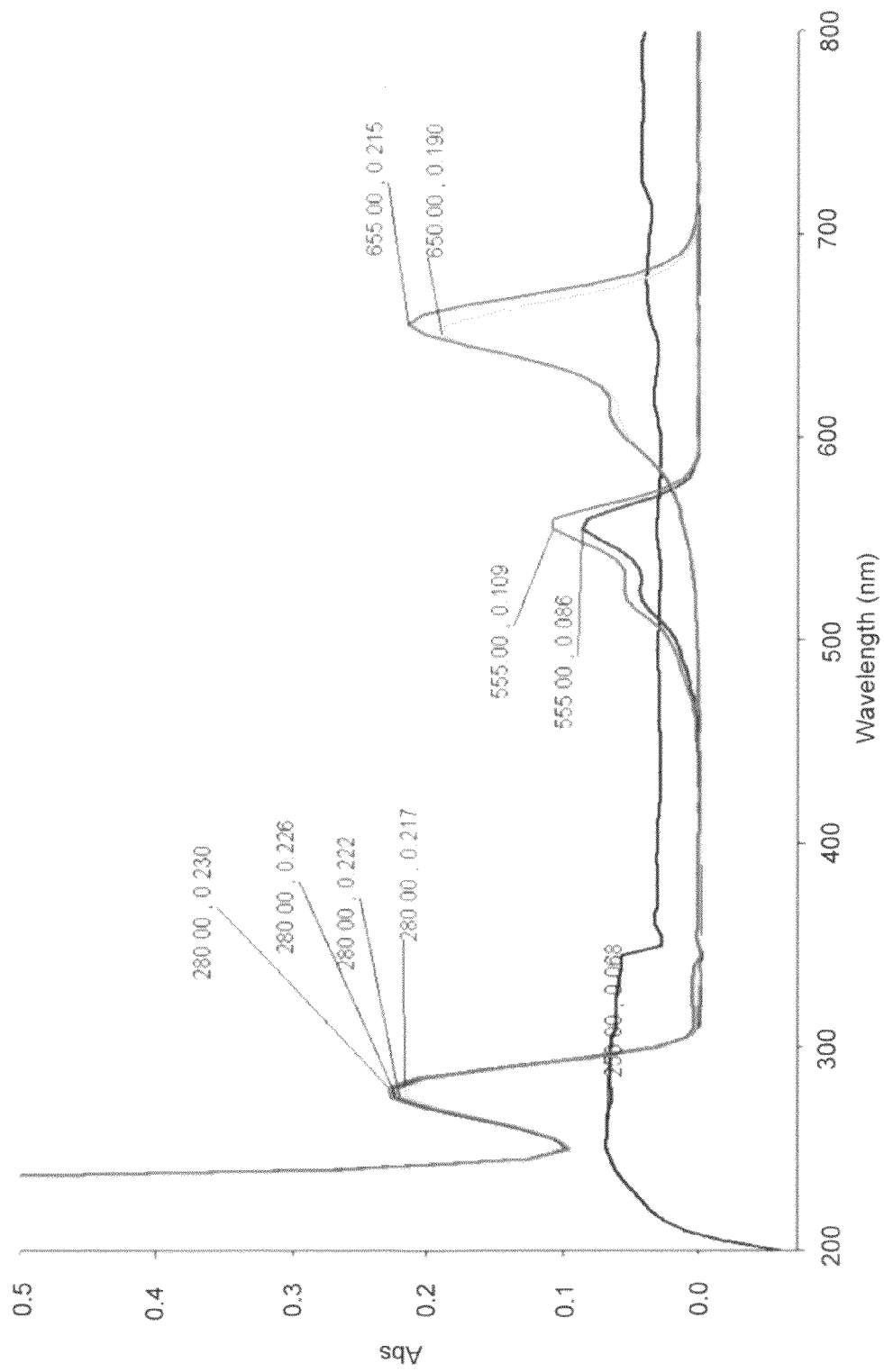
FIG. 8 shows absorbance of conjugates comprising various phosphine-containing compounds.

Fluorescence intensity was measured for compound-PEG$_4$-GAR conjugates where the compound was DyLight 549-phosphine (blue), 550 Compound 1-phosphine (green), DyLight 649-phosphine (yellow) and 650 Compound 1-phosphine (red) (baseline (100% transmission)). FIG. 8 showing absorbance scan of the conjugates after removal of the unconjugated dyes.

Figure 9:
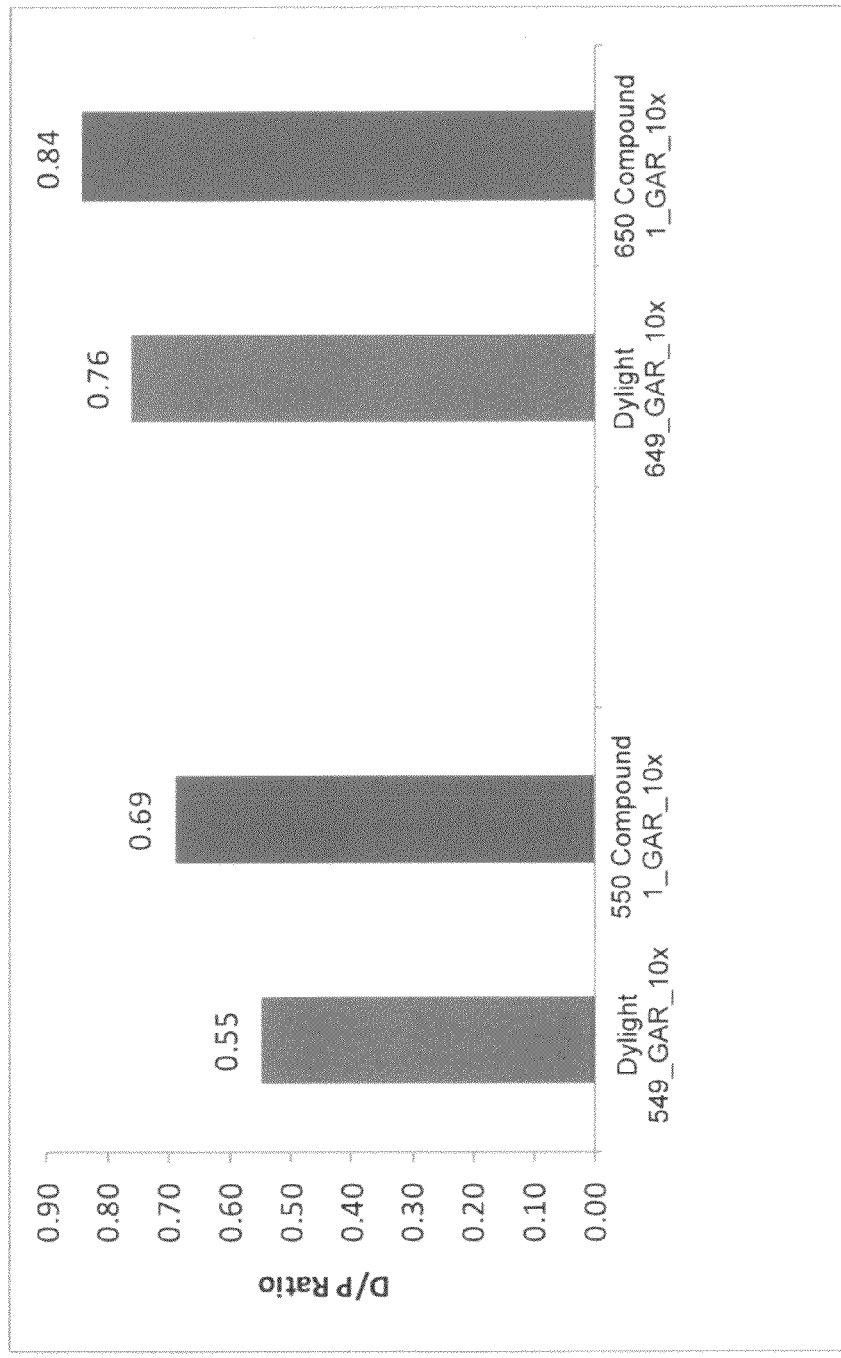
FIG. 9 shows dye to protein ratio (D/P) for conjugates comprising various phosphine-containing compounds.
Figure 10:
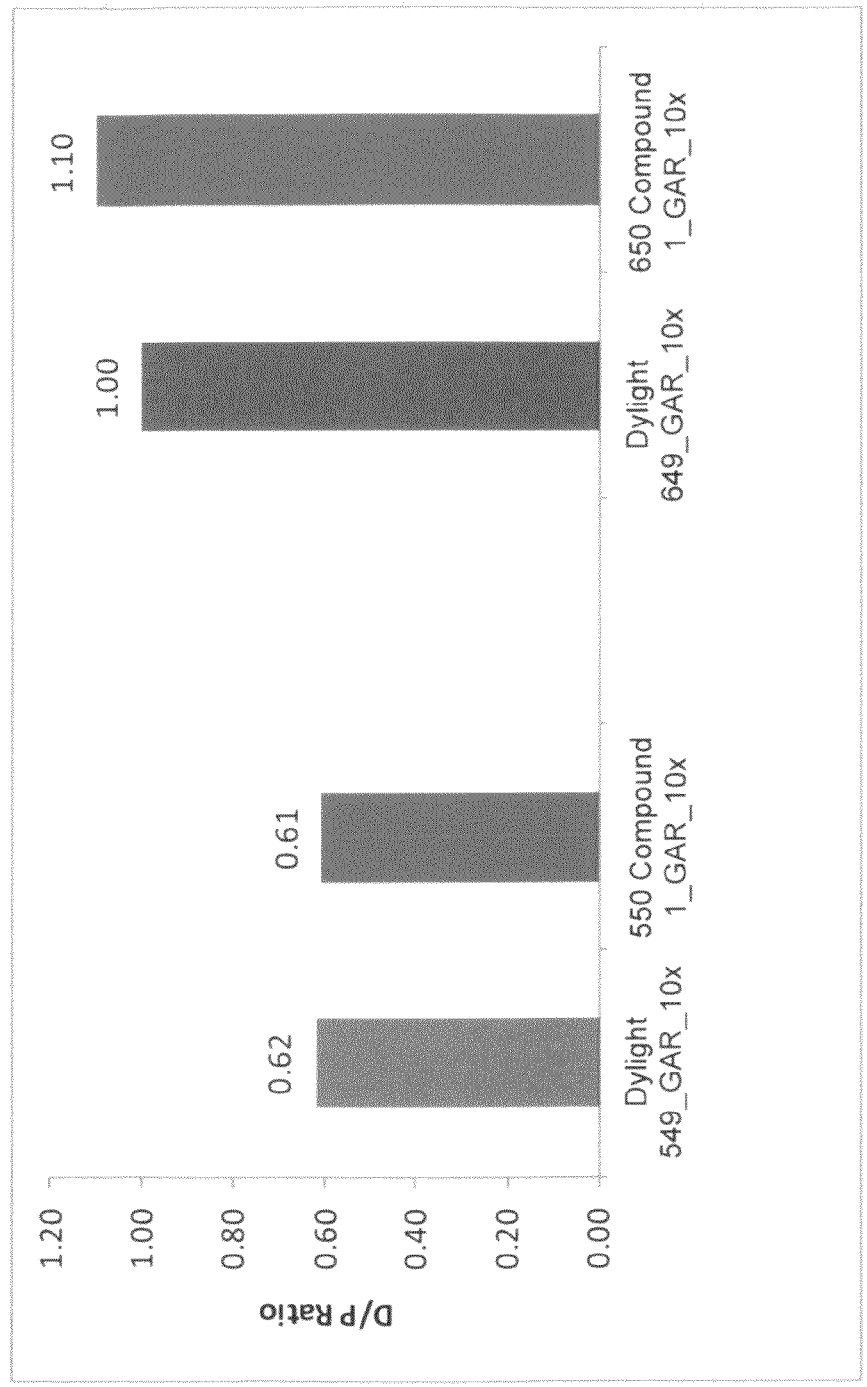
FIG. 10 shows D/P for conjugates comprising various phosphine-containing compounds.

The conjugates were scanned and moles of dye per mole of protein (D/P) was calculated. Labeling efficiency was compared for compound-PEG$_4$-GAR conjugates where the compound was DyLight 549-phosphine (left group; blue), 550 Compound 1-phosphine (left group; red), DyLight 649-phosphine (right group; blue) and 650 Compound 1-phosphine (right group; red) (FIG. 9) and for compound-PEG$_4$-GAM conjugates where the compound was DyLight 549-phosphine (left group; blue), 550 Compound 1-phosphine (left group; red), DyLight 649-phosphine (right group; blue) and 650 Compound 1-phosphine (right group; red) (FIG. 10). The antibody was derivatized with NHS-PEG$_4$-azide. After removal of the unreacted NHS-azide, the 550 Compound 1- or 650 Compound 1-phosphine was allowed to react with the azide labeled antibody. The reaction was carried out for 2-3 hours and then the free dye was removed using the pierce Dye Removal Resin. Absorbance scans were performed and the mole dye to mole protein ration was determined. 550 Compound 1-phosphine showed 25% increase and 650 Compound 1-phosphine showed 10% increase over DyLight 549 or DyLight 649, respectively, in the GAR-containing conjugates. 550 Compound 1-phosphine showed a 2% decrease and 650 Compound 1-phosphine showed 10% increase over DyLight 549 or DyLight 649, respectively, in the GAMcontaining conjugates. The results showed slightly higher dye incorporation with both 550 Compound 1 and 650 Compound 1 compared to DyLight 549 and DyLight 649, respectively.

EXAMPLE 22

Performance of compound-GAM conjugates and compound-GAR conjugates was evaluated in a functional assay. Wells of a 96 white opaque plate were coated with target proteins mouse IgG immunoglobulin or rabbit IgG immunoglobulin. One hundred μl mouse or rabbit IgG at a concentration of 10 μg/ml was applied to the corresponding wells in columns 1 and 2. The target proteins were serially diluted 1:1 from the wells in columns 2 to 11 using 100 μl PBS. One hundred μl of samples from the wells in column 11 were discarded. One hundred μl PBS was added to the wells in column 12. The plates were incubated overnight at 4° C. and then blocked 2×200 μl with Thermo Scientific SuperBlock® Blocking Buffer. The coated plates were washed 2×200 μl with PBS-Tween and 1×200 μl with PBS. Conjugates diluted in PBS to 4 μg/ml were added to the corresponding plates (100 μl/well) and then incubated for one h in the dark. The plates were washed with 2×200 μl with PBS-Tween and 1×200 μl with PBS and filled with PBS buffer (100 μl/well) prior to scanning on Tecan Safire using 562 $nm_{excitation}/576$ $nm_{emission}$ to detect fluorescence intensity and DyLight 649 and DyLight 650 plated were measured using 654 $nm_{excitation}/673$ $nm_{emission}$.

Figure 11:
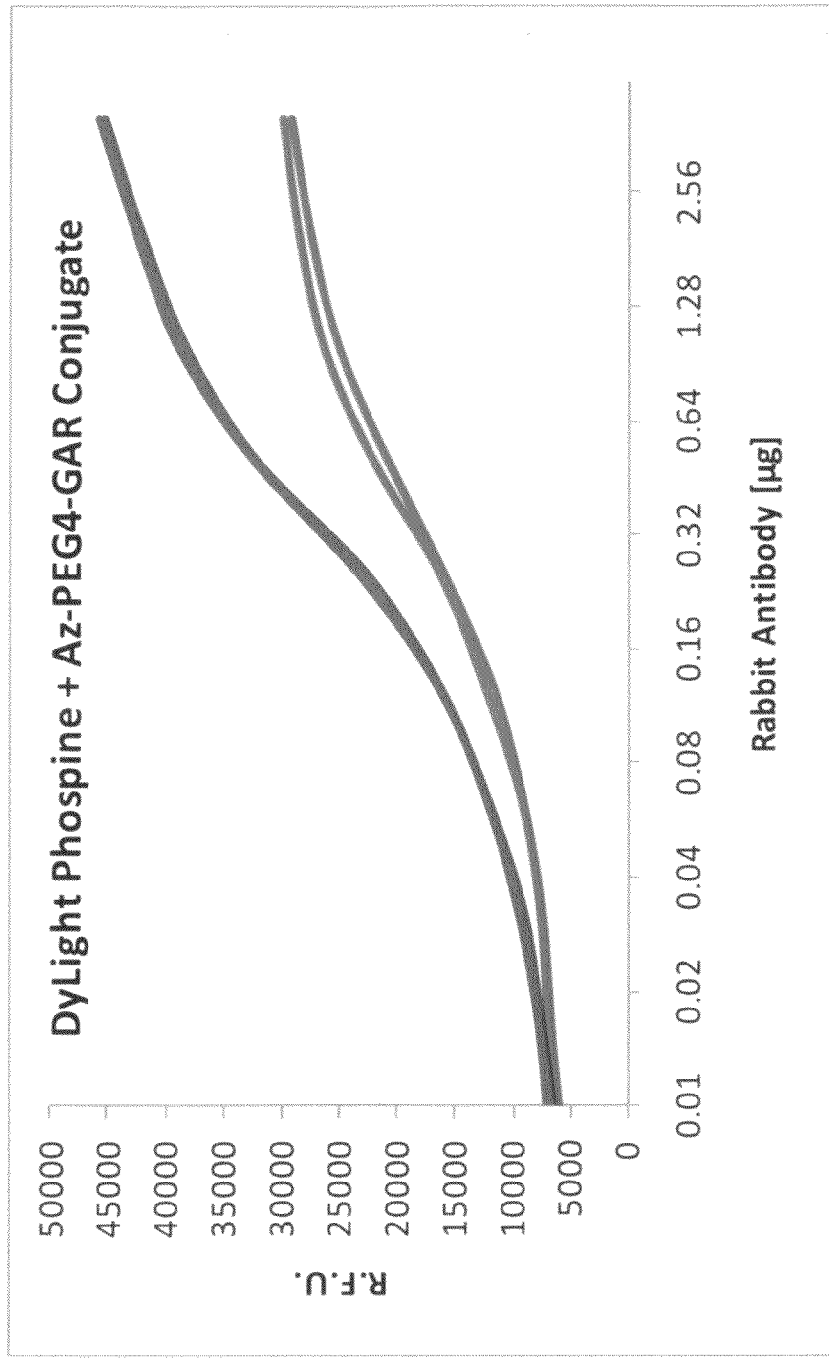
FIG. 11 shows relative RFU for conjugates comprising various phosphine-containing compounds.
Figure 12:
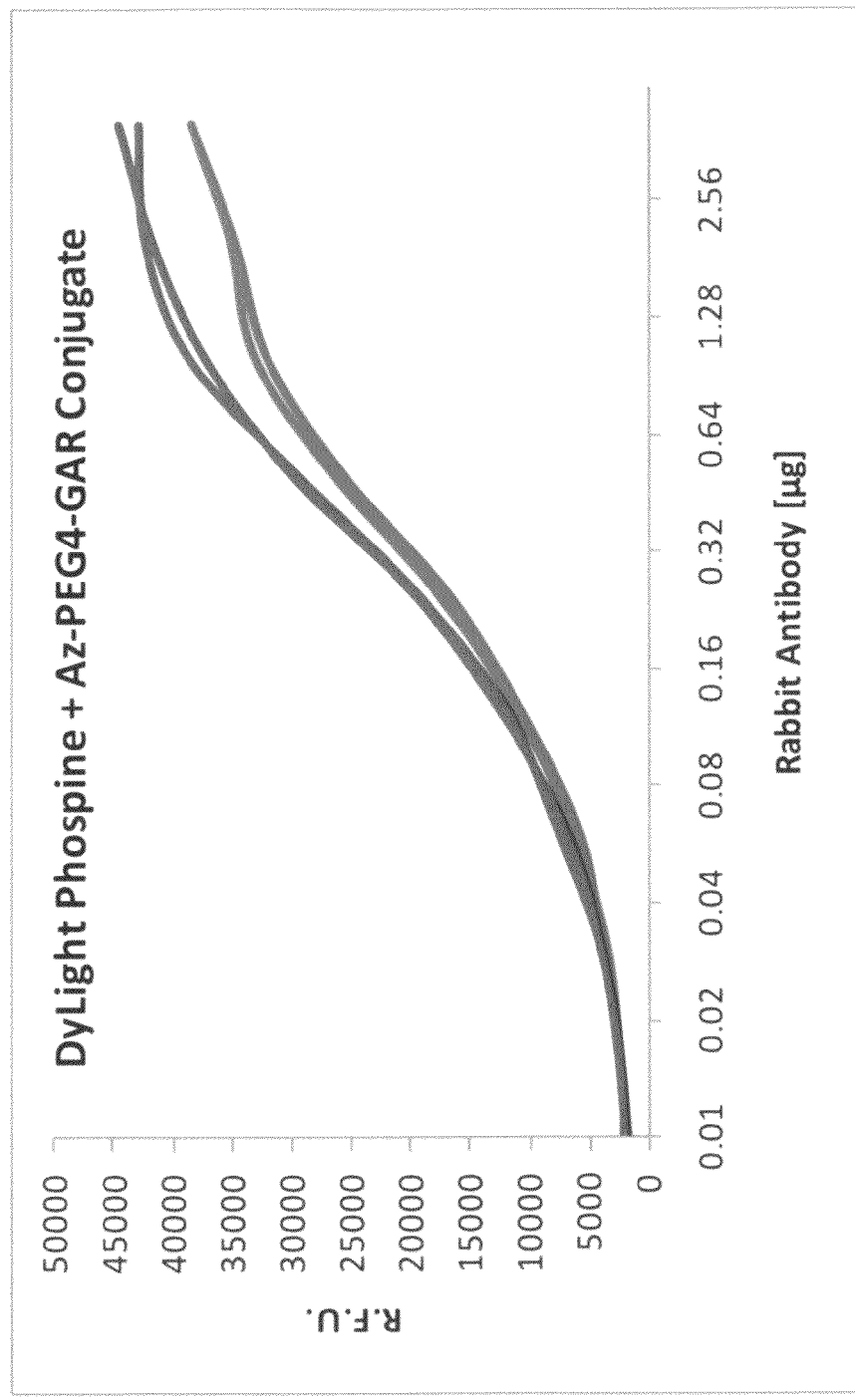
FIG. 12 shows RFU for conjugates comprising various phosphine-containing compounds.

As shown in FIGS. 11-12, relative fluorescence units (RFU) were compared for compound-PEG$_4$-GAR conjugates where the compound was DyLight 549-phosphine (red; FIG. 11), 550 Compound 1-phosphine (blue; FIG. 11), DyLight 649-phosphine (red; FIG. 12) and 650 Compound 1-phosphine (blue; FIG. 12) at various concentrations; the experiment was performed in duplicate.

Figure 13:
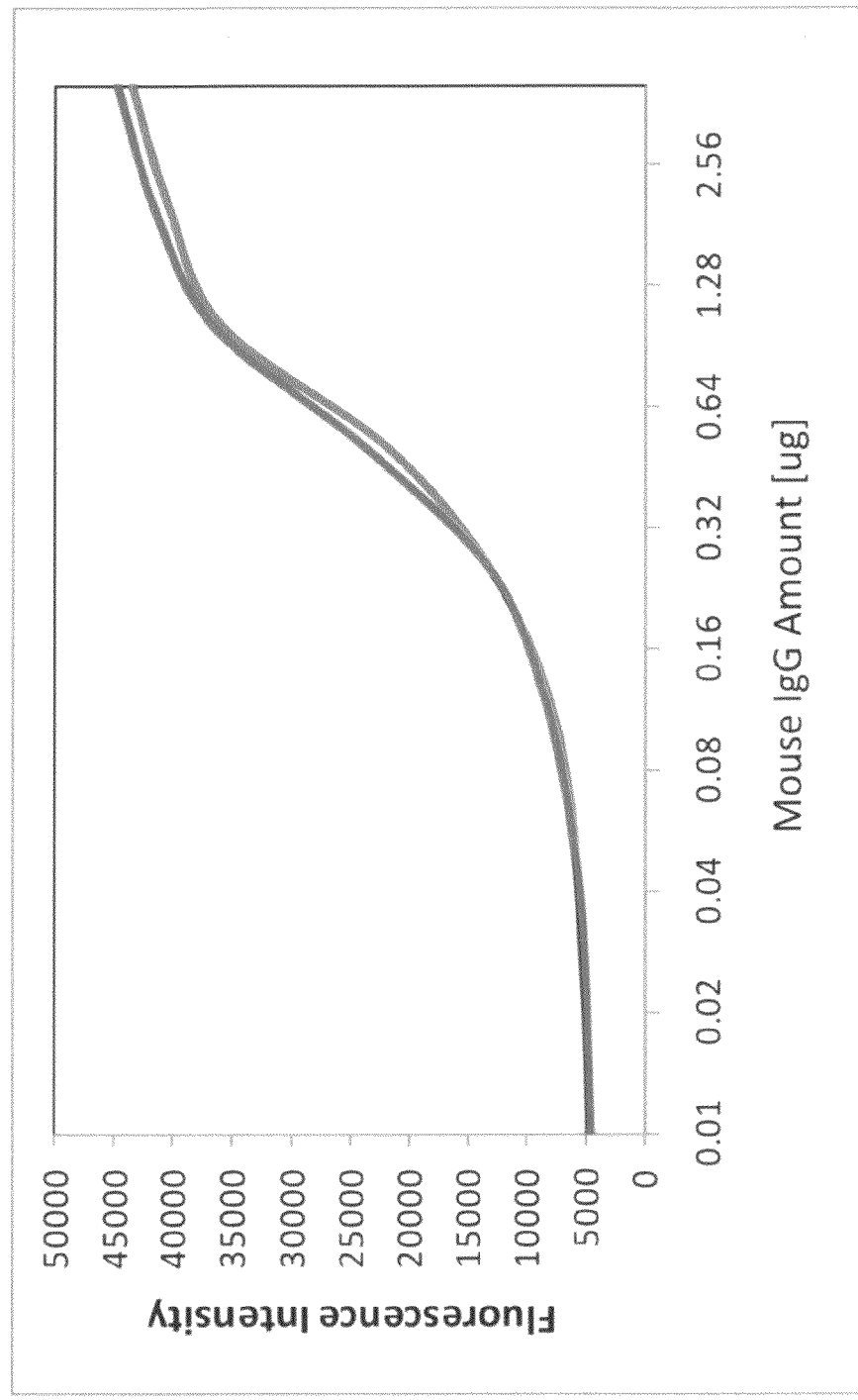
FIG. 13 shows fluorescence intensity for conjugates comprising various phosphine-containing compounds.
Figure 14:
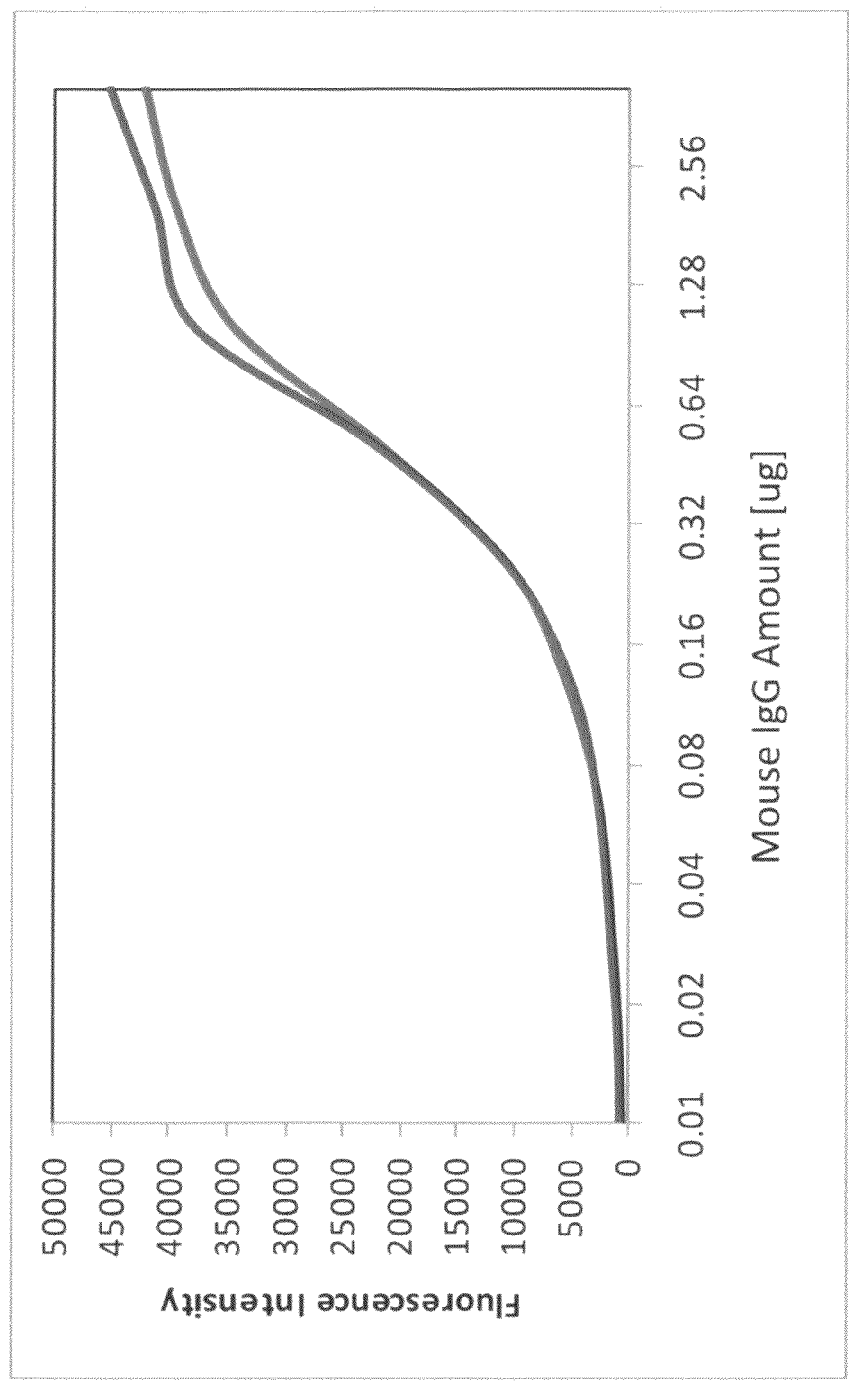
FIG. 14 shows fluorescence intensity for conjugates comprising various phosphine-containing compounds.

As shown in FIGS. 13-14, the fluorescence intensity, also termed the RFU, was compared for compound-PEG$_4$-GAM conjugates where the compound was DyLight 549-phosphine (blue; FIG. 13), 550 Compound 1-phosphine (red; FIG. 13), DyLight 649-phosphine (red; FIG. 14) and 650 Compound 1-phosphine (blue; FIG. 14) at various concentrations. The results for DyLight 549 and 550 Compound 1 were similar. The results for DyLight 649 and 650 Compound 1 were similar.

Figure 15:
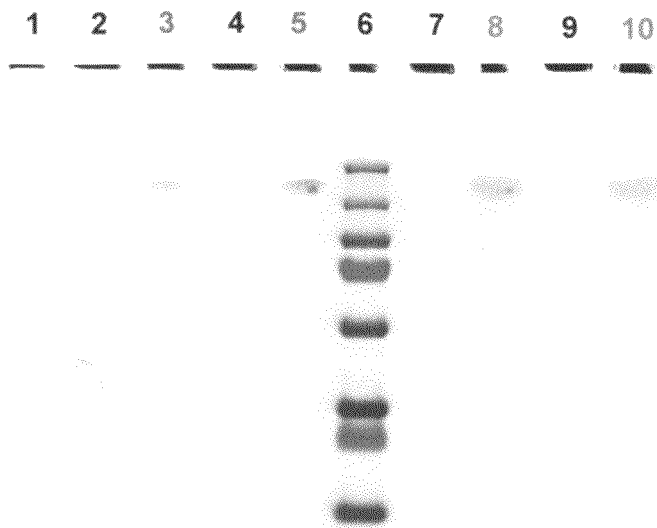
FIG. 15 shows sodium dodecyl sulfate-polyacrylamide gel electrophoresis (SDS-PAGE) for conjugates comprising various phosphine-containing compounds.
Figure 16:
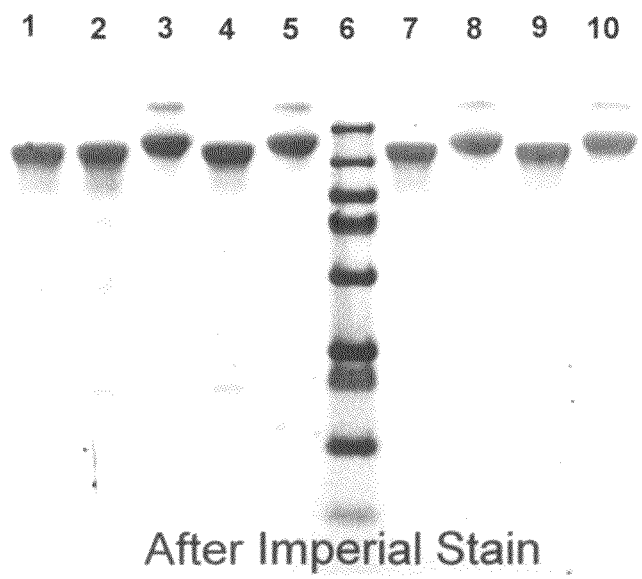
FIG. 16 shows SDS-PAGE for conjugates comprising various phosphine-containing compounds.

SDS-PAGE was performed (with minimal protein reduction) as shown in FIGS. 15 and 16 with 10 μg of non-reduced antibody loaded in each lane. The dye labeled samples were prepared in non-reducing LDS sample buffer, heated to 95° C. for 5 min. The samples were applied to a 4-12% Bis-Tris gel and subjected to electrophoresis. The gels were then scanned using the Epson Scanner (FIG. 15), then stained with Imperial Protein Stain for one hour, destained, and then scanned (FIG. 16). The results showed that azido-PEG4 conjugated with GAR reacted with dye-phosphines.

Figure 17:
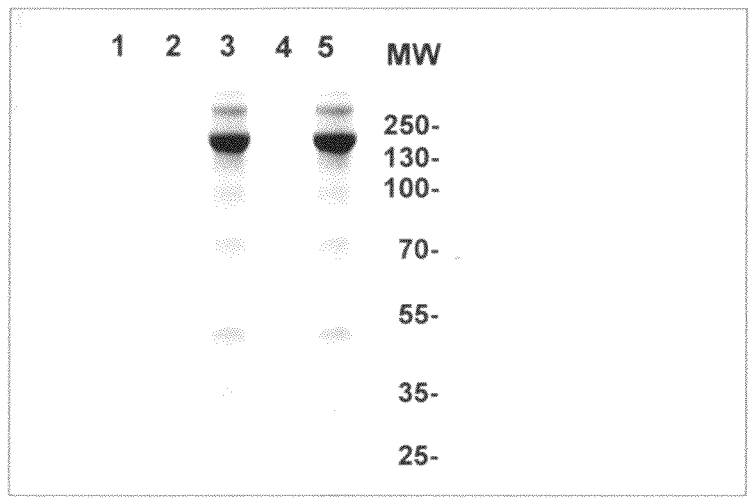
FIG. 17 shows SDS-PAGE for conjugates comprising various phosphine-containing compounds.
Figure 18:
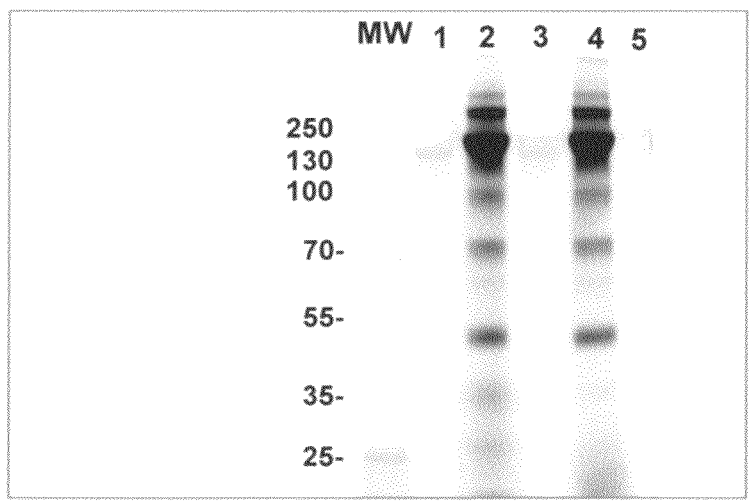
FIG. 18 shows SDS-PAGE for conjugates comprising various phosphine-containing compounds.
Figure 19:
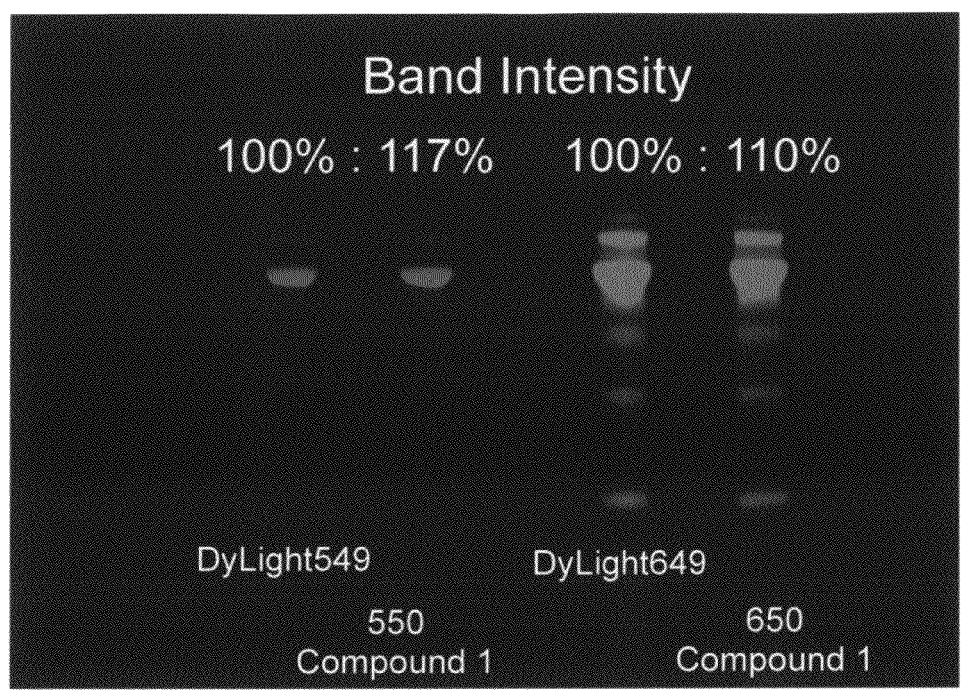
FIG. 19 shows fluorescence of conjugates comprising various phosphine-containing compounds in a gel.

GAR conjugates in gel is shown in FIGS. 17 and 18, and fluorescence shown in FIG. 19. Sample preparation and gel electrophoresis was the same as described for FIGS. 15-16. The results show coupling of the dye only when the antibody is derivatized with an azido group. Gels were scanned using Typhoon 9410 imager with the Cy3 laser and Cy5 laser settings.

EXAMPLE 23

The inventive compounds were evaluated for stability compared to commercial dyes. All compounds were packed under argon as 1 mg portions in plastic vials. The vials were sealed under argon with a drying pad in an aluminium coated pouch, and then stored at 50° C. for 14 days. The results of the stability study for selected compounds are shown below where the determination of purity was by HPLC before and after storage.

550 Compound 1-Phosphine

| | Purity | |
|---|---|---|
| Unit size | Before thermal stress | After thermal stress |
| 1 mg | 96% | 96% |

650 Compound 1-Phosphine

| | Purity | |
|---|---|---|
| Unit size | Before thermal stress | After thermal stress |
| 1 mg | 97% | 96% |

The inventive compounds exhibited >90% stability by HPLC from various lots.

Figure 20:
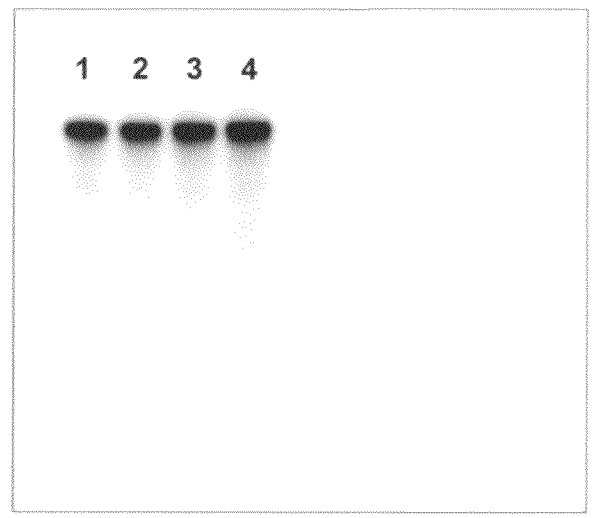
FIG. 20 shows fluorescence images of SDS-PAGE gels of conjugates comprising various phosphine-containing compounds.
Figure 21:
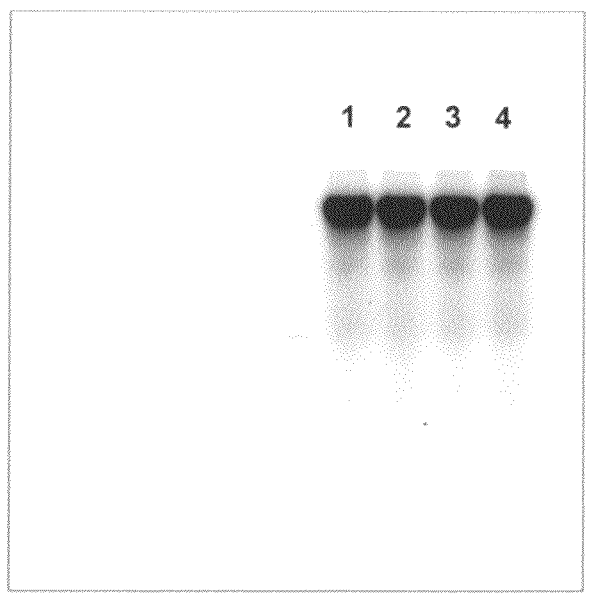
FIG. 21 shows fluorescence images of SDS-PAGE gels of conjugates comprising various phosphine-containing compounds.
Figure 22:
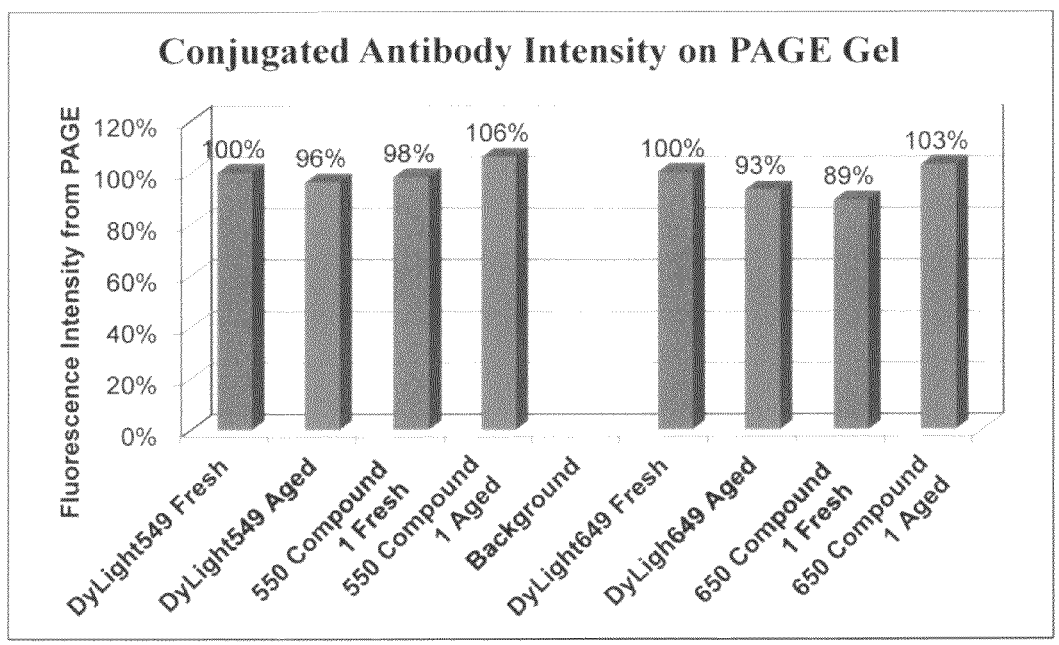
FIG. 22 shows fluorescence intensity for conjugates comprising various phosphine-containing compounds in a gel.

Conjugate stability was also assessed. 550 Compound 1- and 650 Compound 1-phosphines were conjugated to azido-PEG$_4$-GAM, subjected to 50° C. for five days, and examined by Western blot. As shown in FIGS. 20 and 21, and a plot of the conjugate fluorescent intensity shown in FIG. 22, where each lane was loaded with 3 μg of antibody. The inventive compound-phosphine derivatives are stable for >20 months at −20° C.

Figure 23:
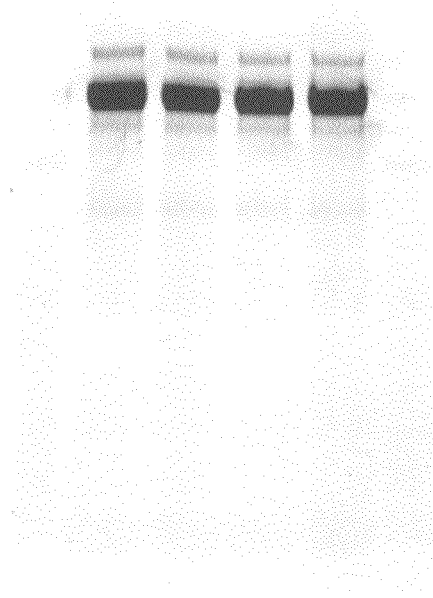
FIG. 23 shows conjugates comprising various phosphine-containing compounds in a gel.
Figure 24:
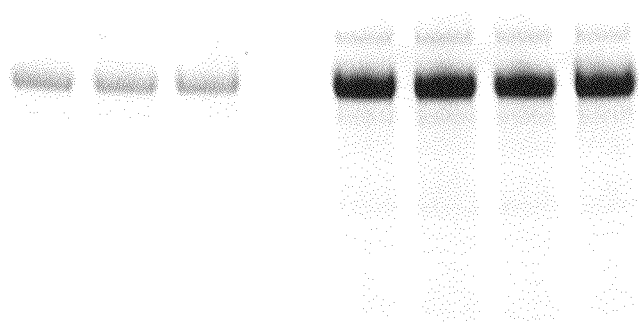
FIG. 24 shows conjugates comprising various phosphine-containing compounds in a gel.
Figure 25:
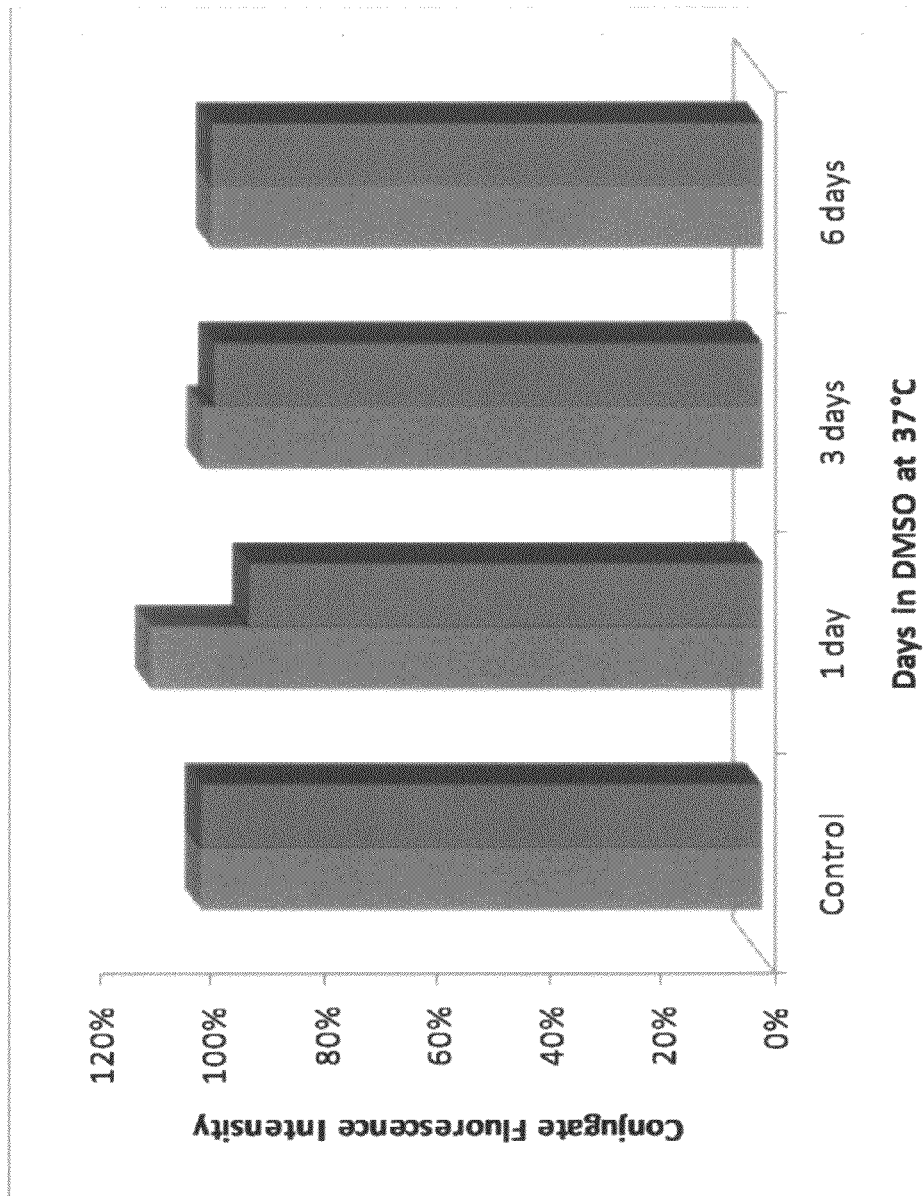
FIG. 25 shows fluorescence intensity for conjugates comprising various phosphine-containing compounds in a gel.
Figure 26:
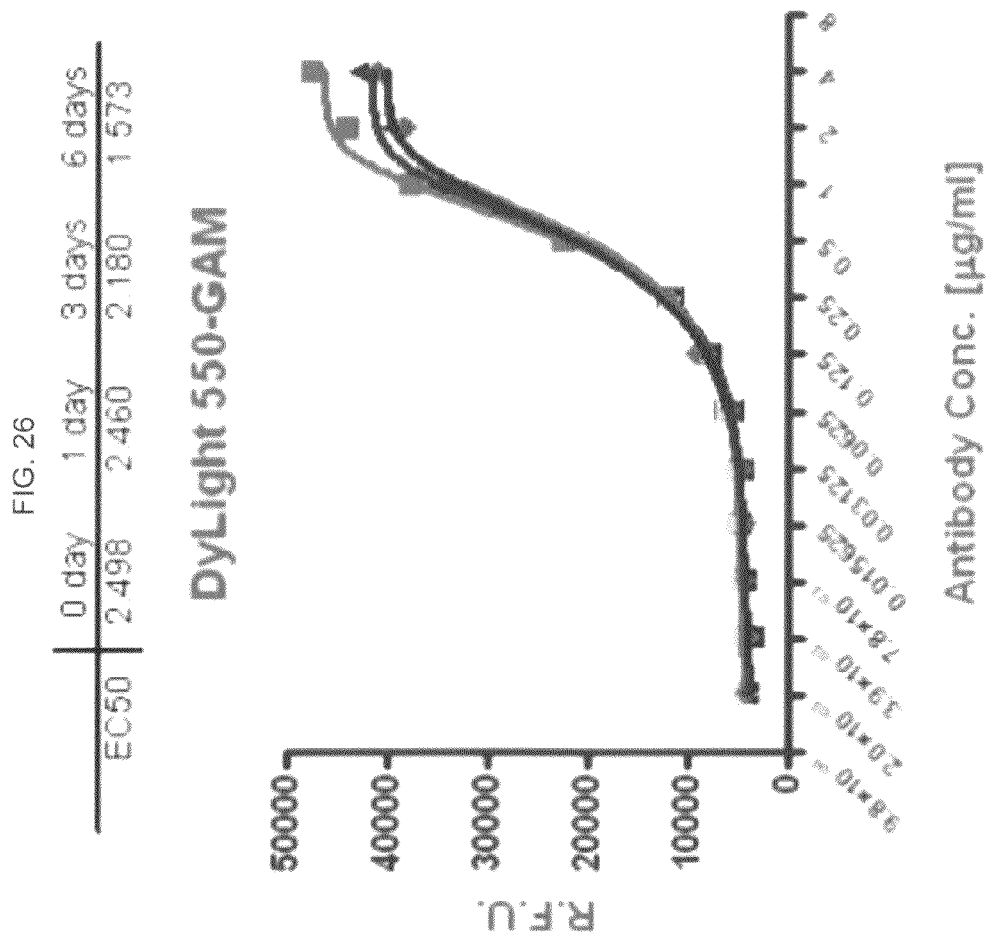
FIG. 26 shows RFU for conjugates comprising various phosphine-containing compounds.
Figure 27:
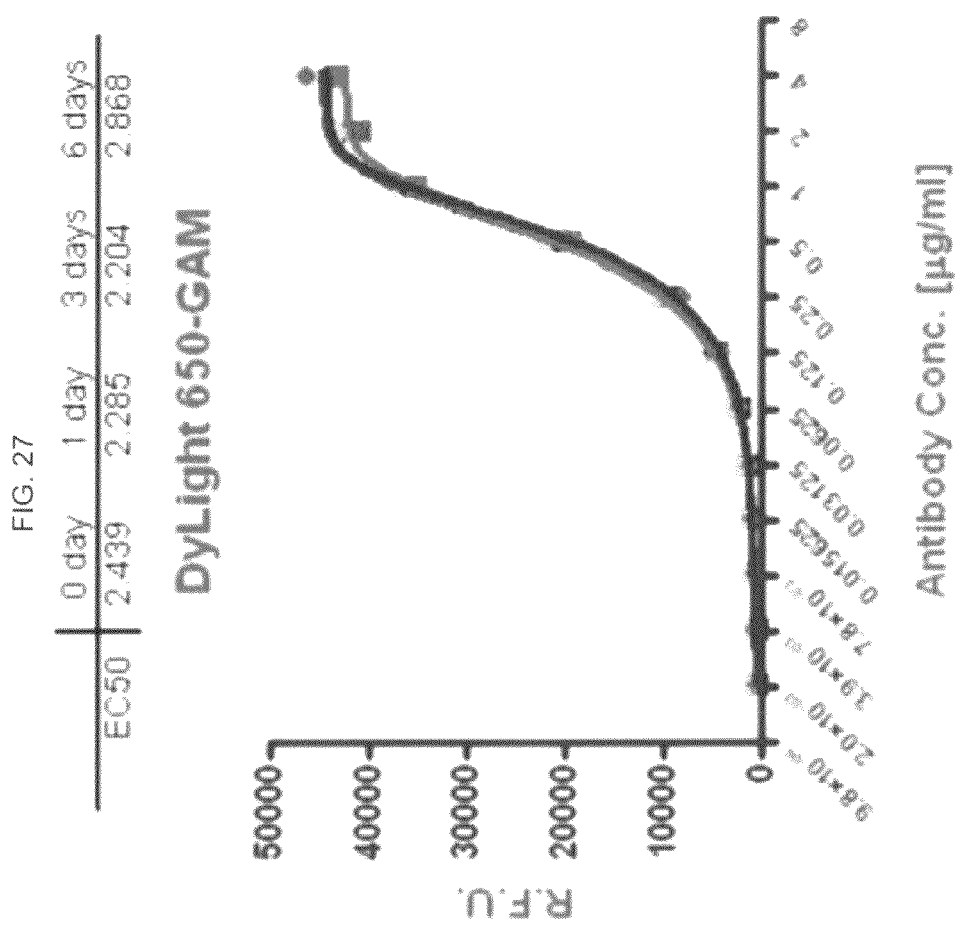
FIG. 27 shows RFU for conjugates comprising various phosphine-containing compounds.

The phosphine-containing compounds stability, in the presence of dimethylsulfoxide (DMSO) were also examined. Phosphine-containing compounds were kept in DMSO solution at 37° C. for varying numbers of days, and then conjugated with azido-PEG4-GAM. The 550 Compound 1-phosphine-PEG$_4$-GAM conjugates (FIG. 23) and 650 Compound 1-phosphine-PEG$_4$-GAM conjugates (FIG. 24) were subjected to Western blot after 0 day (lane 1), 1 day (lane 2), 2 days (lane 3), and 3 days (lane 4). The resultant fluorescence intensity of the various conjugates from FIGS. 23 and 24 are shown in FIG. 25. The relative fluorescence units (RFU) of conjugates formed from the phosphine-containing compounds in DMSO for 0 day (red square), 1 day (blue triangle), 3 days (yellow triangle), and 6 days (green diamond), as a function of the amount of antibody, are shown for 550 Compound 1-phosphine-PEG$_4$-GAM conjugates (FIG. 26) and for 650 Compound 1-phosphine-PEG$_4$-GAM conjugates (FIG. 27). The EC$_{50}$ for each conjugate is also presented. The results indicate that the phosphine-containing compounds are stable in DMSO for at least a week.

EXAMPLE 24

The inventive and commercial compounds were examined in cell labeling experiments using azido-sugars and adenocarcinomic human alveolar basal epithelial (A549) cells, human osteosarcoma (U2OS) cells, and immortalized proximal tubule epithelial (HK2) cells. As is known in the art, introduction of labeled sugar moieties results in incorporation of the labeled sugar moieties in various cellular molecules and locations.

Metabolically incorporated azido-labeled sugars, N-azidoacetyl galactosamine, N-azidoacetyl glucosamine, and N-azidoacetyl mannosamine was detected in vivo. Cells were incubated with 40 μM azido-sugar in cell culture media for 72 hours and the live cells were incubated with 100 µM of dye-labeled phosphine. The cells were then washed, fixed with 4% paraformaldehyde and counterstained with Hoechst 33342 which labels nuclei. For fixed cells, the cells were incubated with the azido-sugar, fixed with 4% paraformaldehyde, permeabilized with 0.1% Triton X-100, and incubated with 100 µM of dye-labeled phosphine. In live cell labeling using the phosphine labeling reaction used 100 µM of the dye-labeled phosphine for three hours at 37° C., and the CLICK-iT® labeling reaction, using DIBO-Alexa dye, used 30 µM of the DIBO Alexa dye for one hour at room temperature (RT). In fixed cell labeling, the phosphine labeling reaction used 100 µM of the dye-labeled phosphine for three hours at 37° C., and the CLICK-iT® labeling reaction, using DIBO-Alexa dye, used 50 µM of the DIBO Alexa dye for one hour at RT in the presence of 5 µM copper for one hour at RT in the absence of copper.

Figure 28:
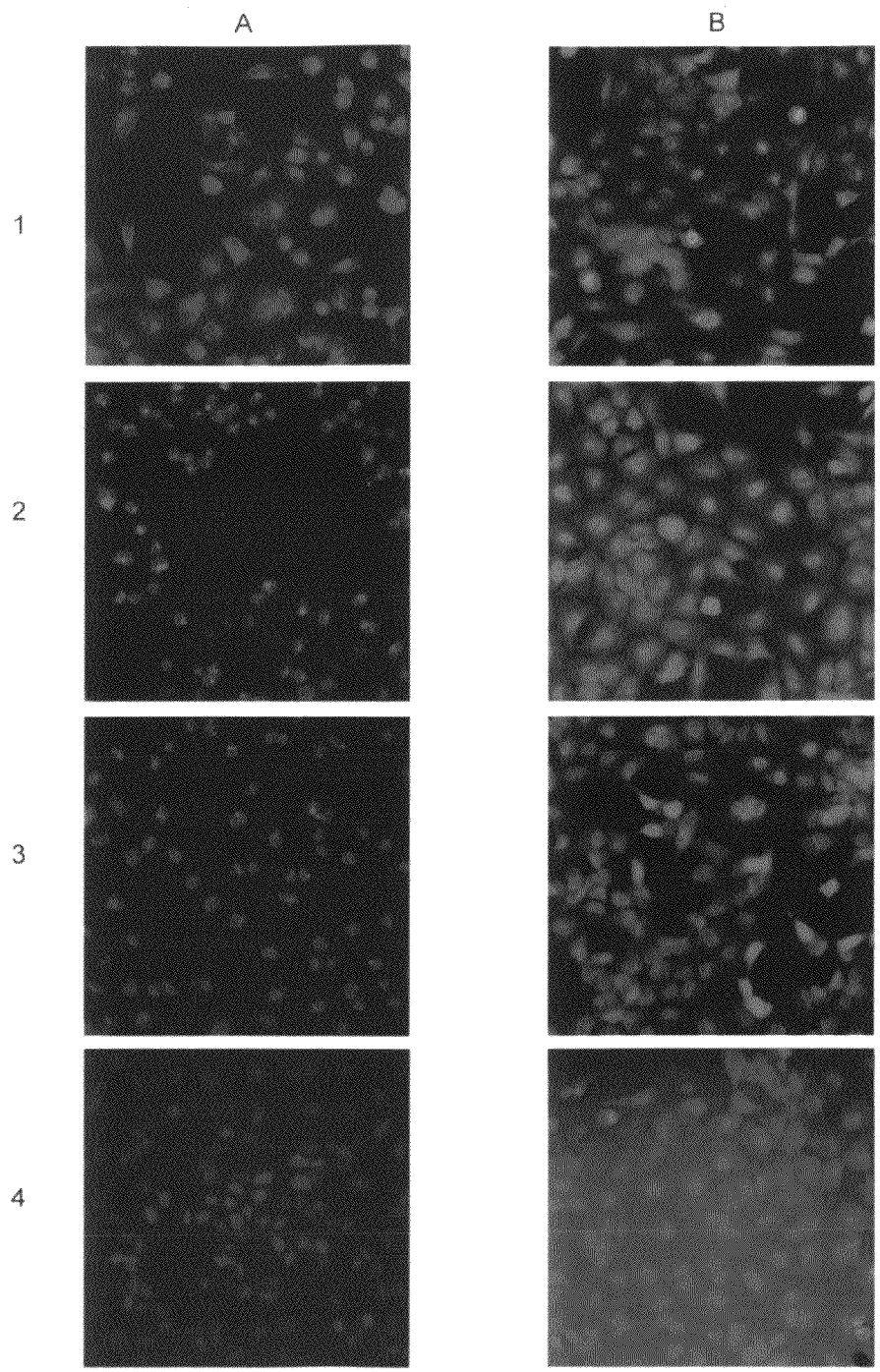
FIG. 28 shows fluorescence images of cells labeled with various phosphine-containing compounds.

Either live (column A) or fixed (column B) A549 cells were labeled with N-azidoacetyl galactosamine, followed by labeling with 550 Compound 1-phosphine (row 1), 650 Compound 1-phosphine (row 2), or Copperless CLICK-IT® using DIBO-Alexa647 (row 3). Fixed A549 cells were labeled with N-azidoacetyl galactosamine followed by labeling using CLICK-iT® reaction using copper with Alexa555-alkyne at either 5 µM for one hour at RT (row 4, column A) or 50 µM for one hour at RT (row 4, column B), as shown in FIG. 28.

Figure 29B:
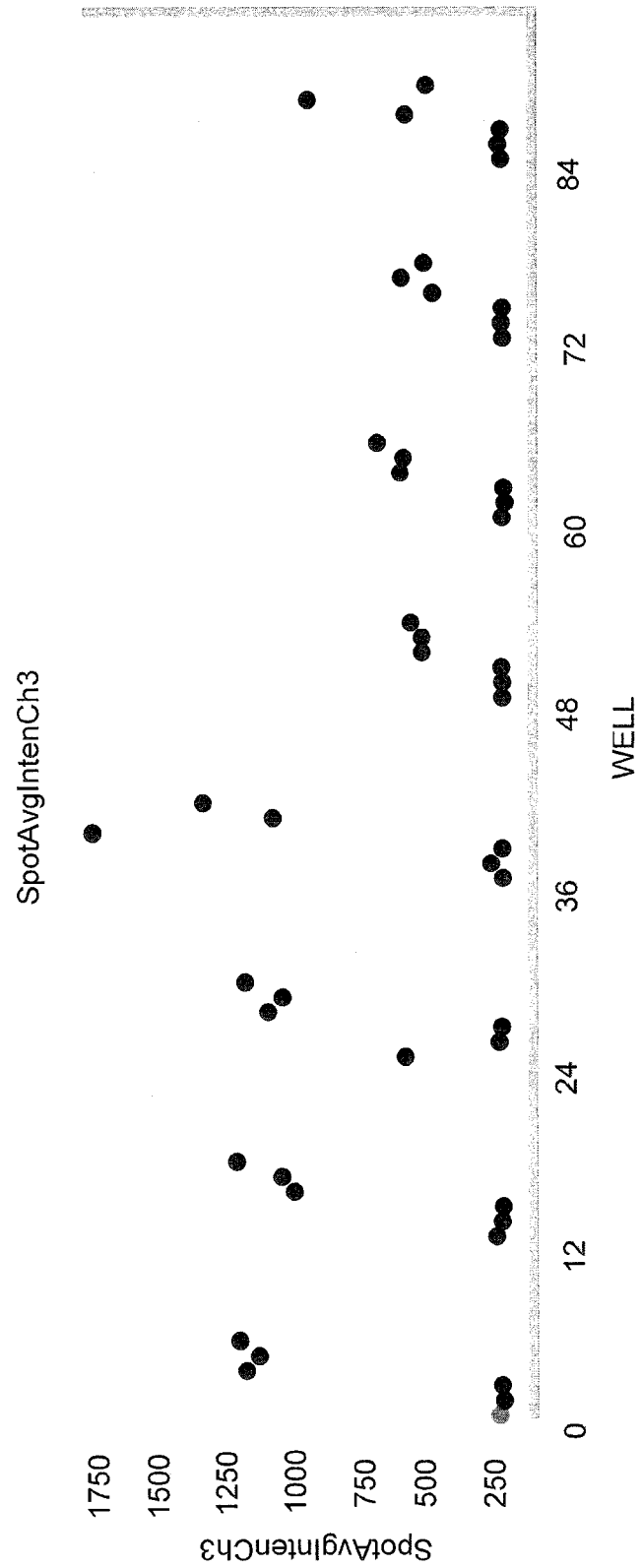
FIG. 29B shows Spot Average Intensity of images of FIG. 28.
Figure 30:
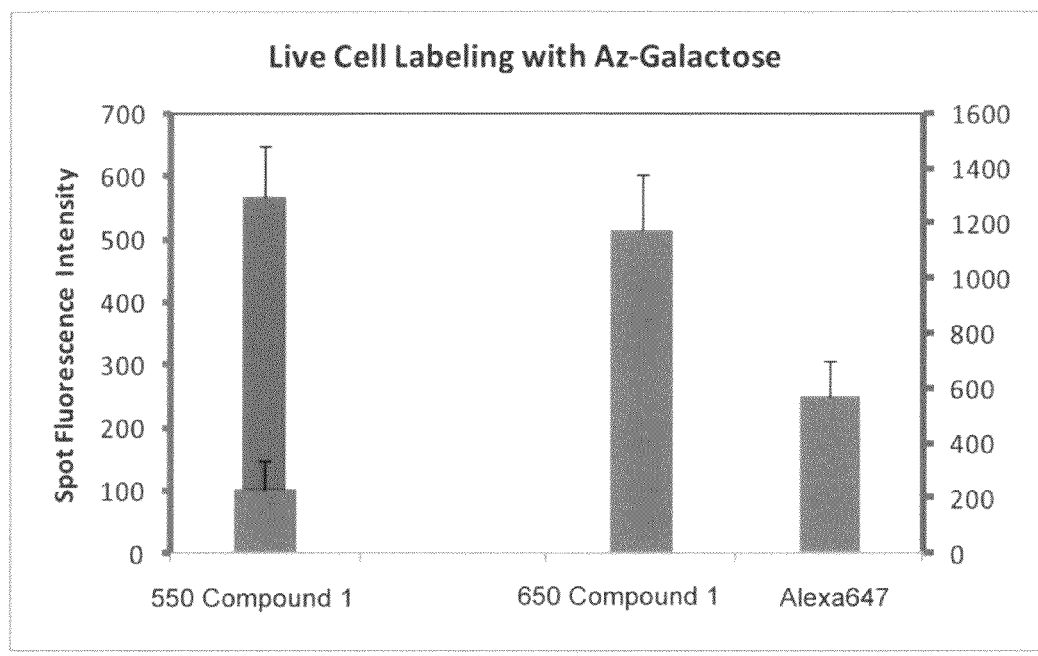
FIG. 30 shows Spot Fluorescence Intensity of the live cell images of FIG. 28.
Figure 31:
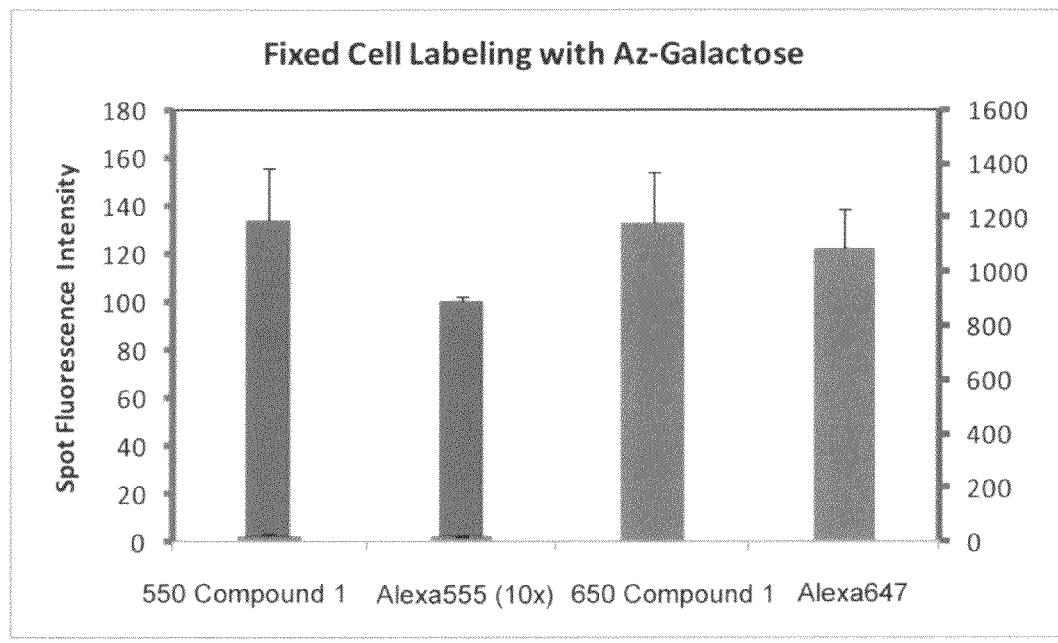
FIG. 31 shows Spot Fluorescence Intensity of the fixed cell images of FIG. 28.

Fluorescence intensity was measured in each spot identified using a specific Bio-Application with the ArrayScanVTI image analysis software. A graph depicting spot average intensity for the live cell images of FIG. 28, is shown for the 550 Compound 1-phosphine labeled cells (FIG. 29A, wells 1-48), the 650 Compound 1-phosphine labeled cells (FIG. 29B, wells 1-48), and the DIBO-Alexa647 labeled cells (FIG. 29B, wells 49-96). A graphical representation of spot average intensity for the images of FIG. 28 is shown for live (FIG. 30, with two Y axes 550 Compound 1 (red) spans up to 700; 650 Compound 1 spans up to 1600) and fixed (FIG. 31) cell labeling. The results showed that, in live cells, 650 Compound 1-phosphine was better than Alexa647-DIBO CLICK-iT® labeling.

Figure 32:
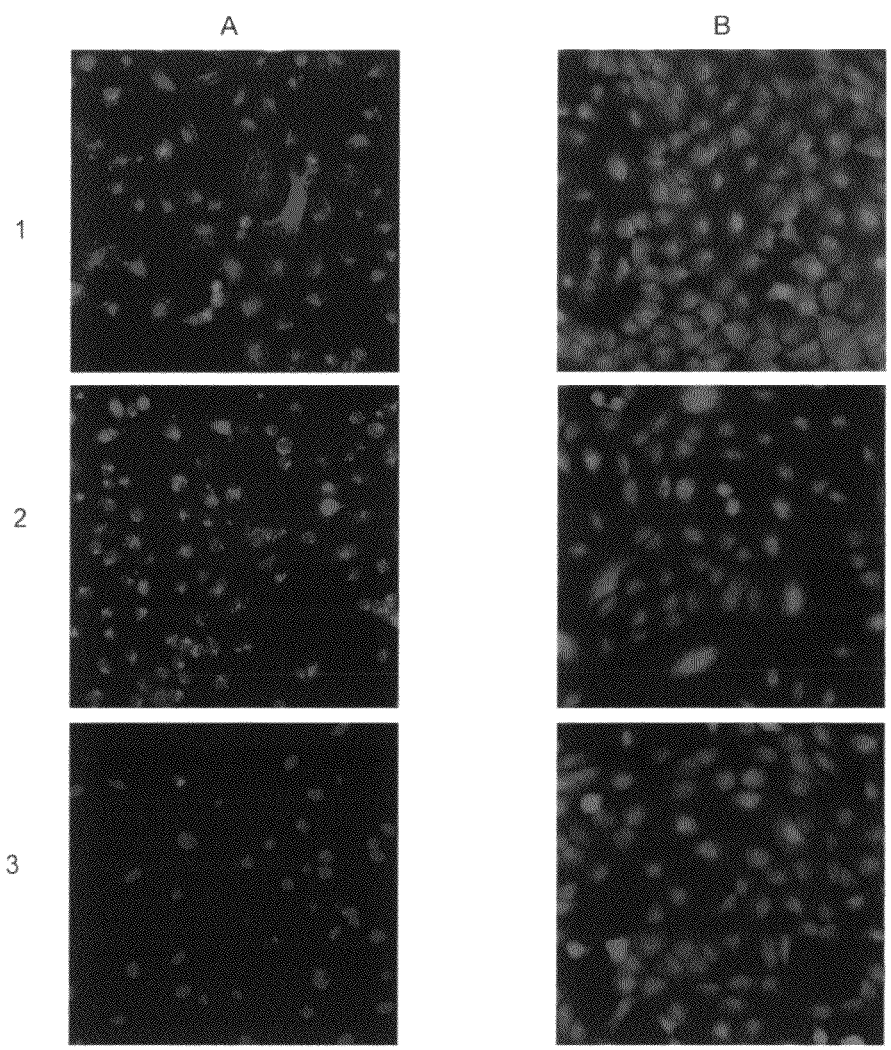
FIG. 32 shows fluorescence images of cells labeled with various phosphine-containing compounds.
Figure 33A:
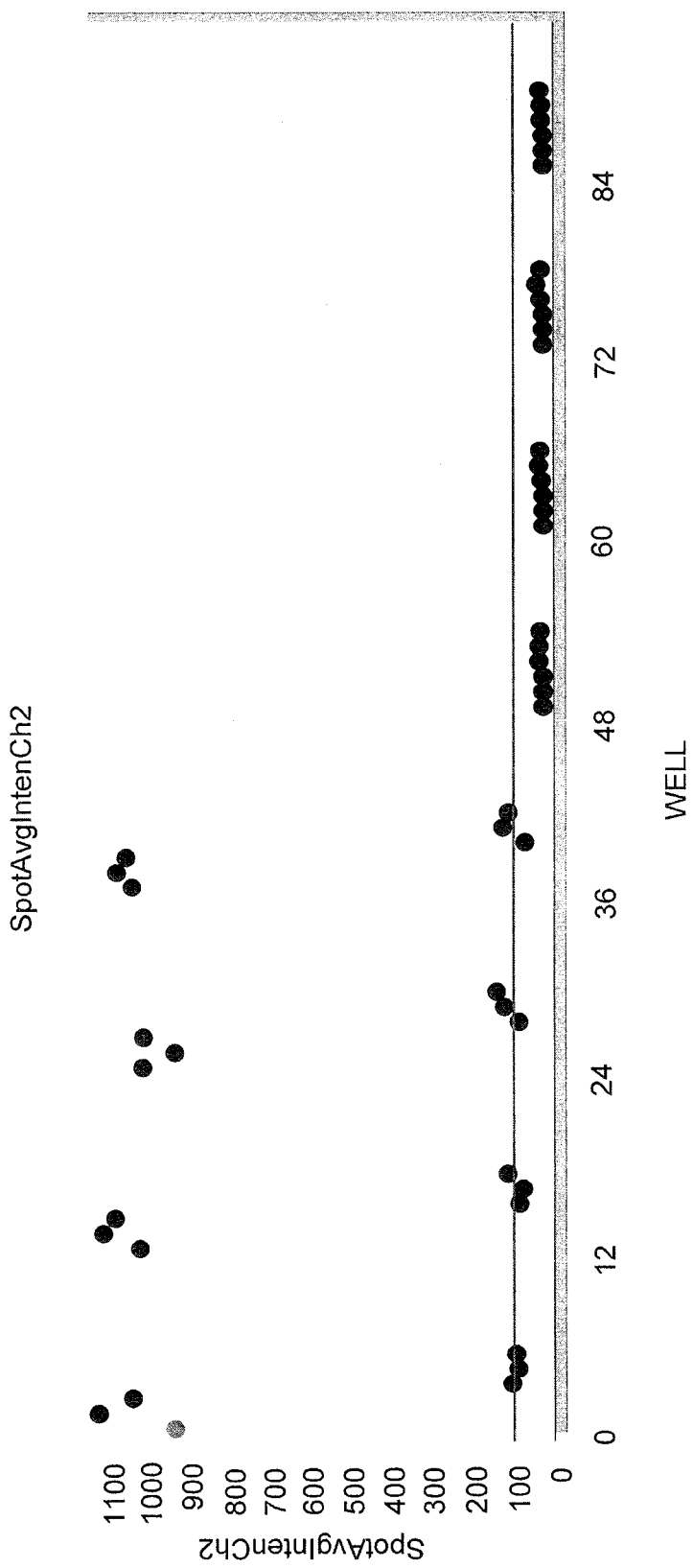
FIG. 33A shows Spot Average Intensity of images of FIG. 32.
Figure 33B:
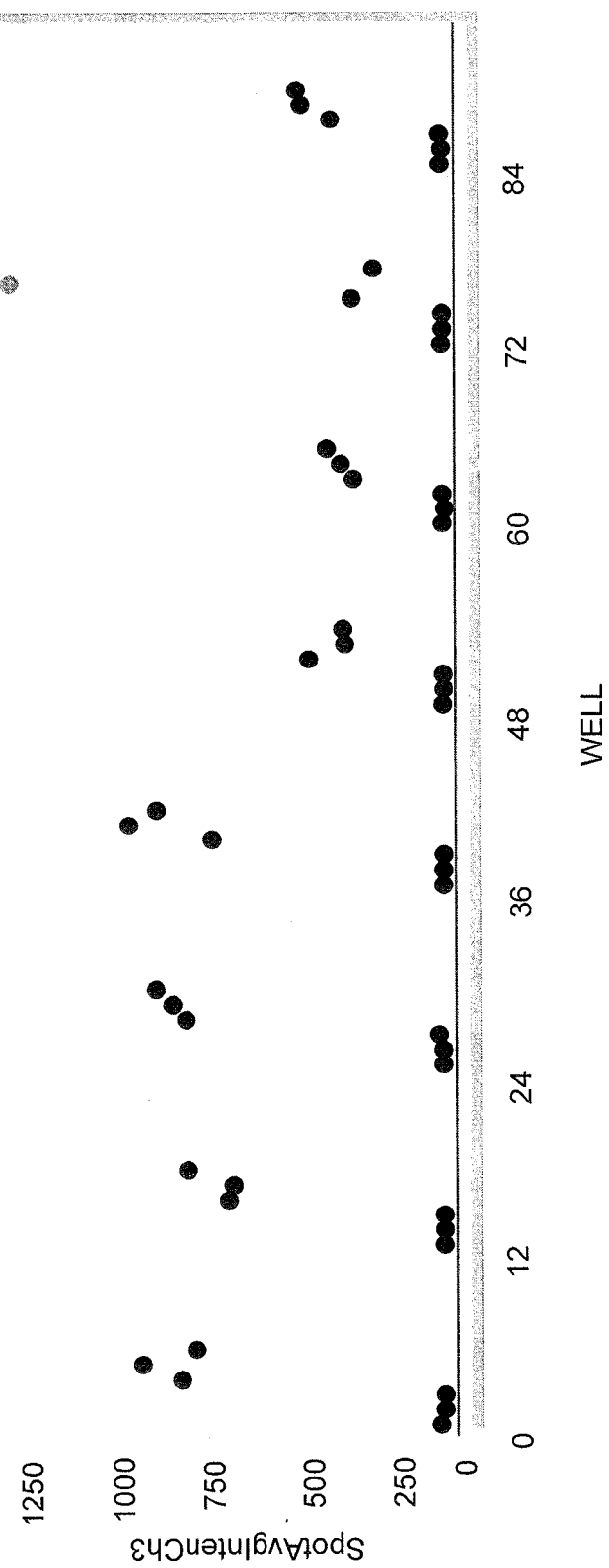
FIG. 33B shows Spot Average Intensity of images of FIG. 32.
Figure 34:
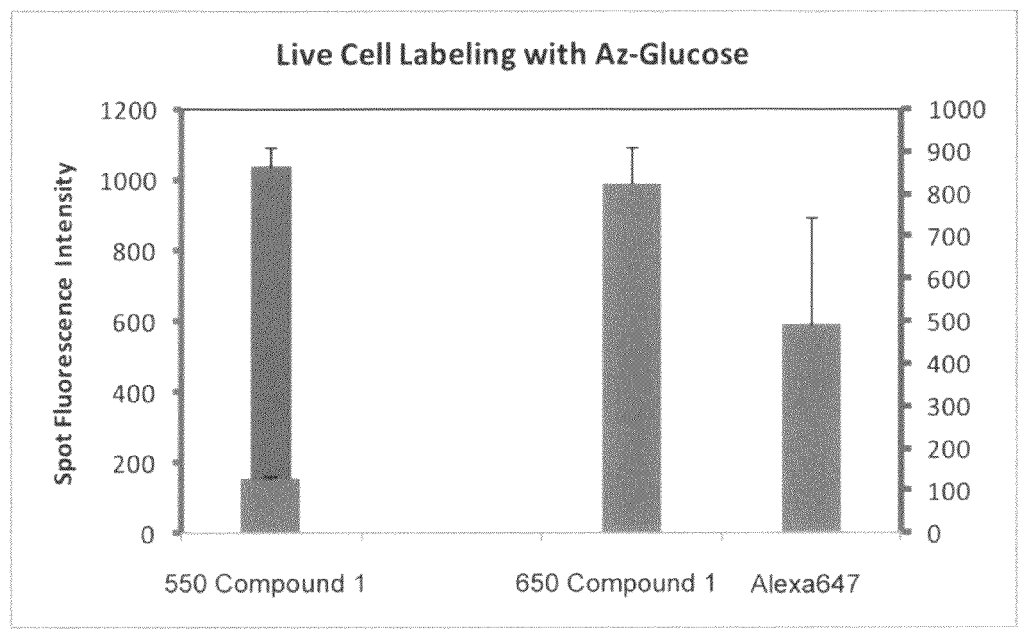
FIG. 34 shows Spot Fluorescence Intensity of the live cell images of FIG. 32.
Figure 35:
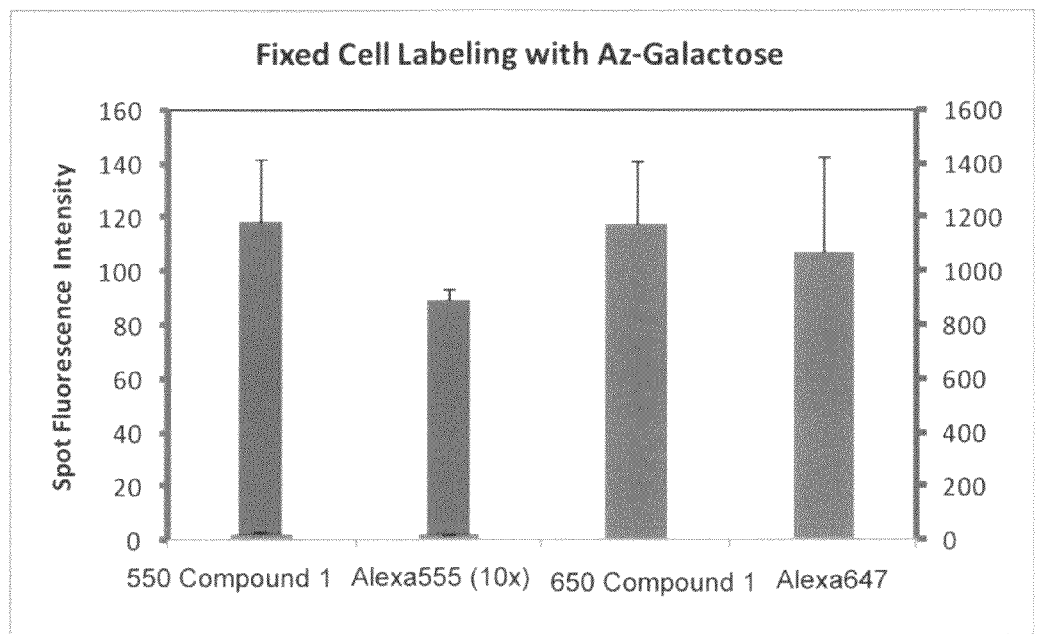
FIG. 35 shows Spot Fluorescence Intensity of the fixed cell images of FIG. 32.

A549 cells, either live (column A) or fixed (column B), were labeled with N-azidoacetyl glucosamine followed by labeling with 550 Compound 1-phosphine (row 1), 650 Compound 1-phosphine (row 2), or Copperless CLICK-iT® using DIBO-Alexa647 (row 3), as shown in FIG. 32. A graph depicting spot average intensity for the live cell images of FIG. 32 is shown for the 550 Compound 1-phosphine labeled cells (FIG. 33A, wells 1-48), the 650 Compound 1-phosphine labeled cells (FIG. 33B, wells 1-48), and the DIBO-Alexa647 labeled cells (FIG. 33B, wells 49-96). A graphical representation of the spot average intensity for the images of FIG. 32 is shown for labeling live (FIG. 34) and fixed (FIG. 35) cells.

Figure 36:
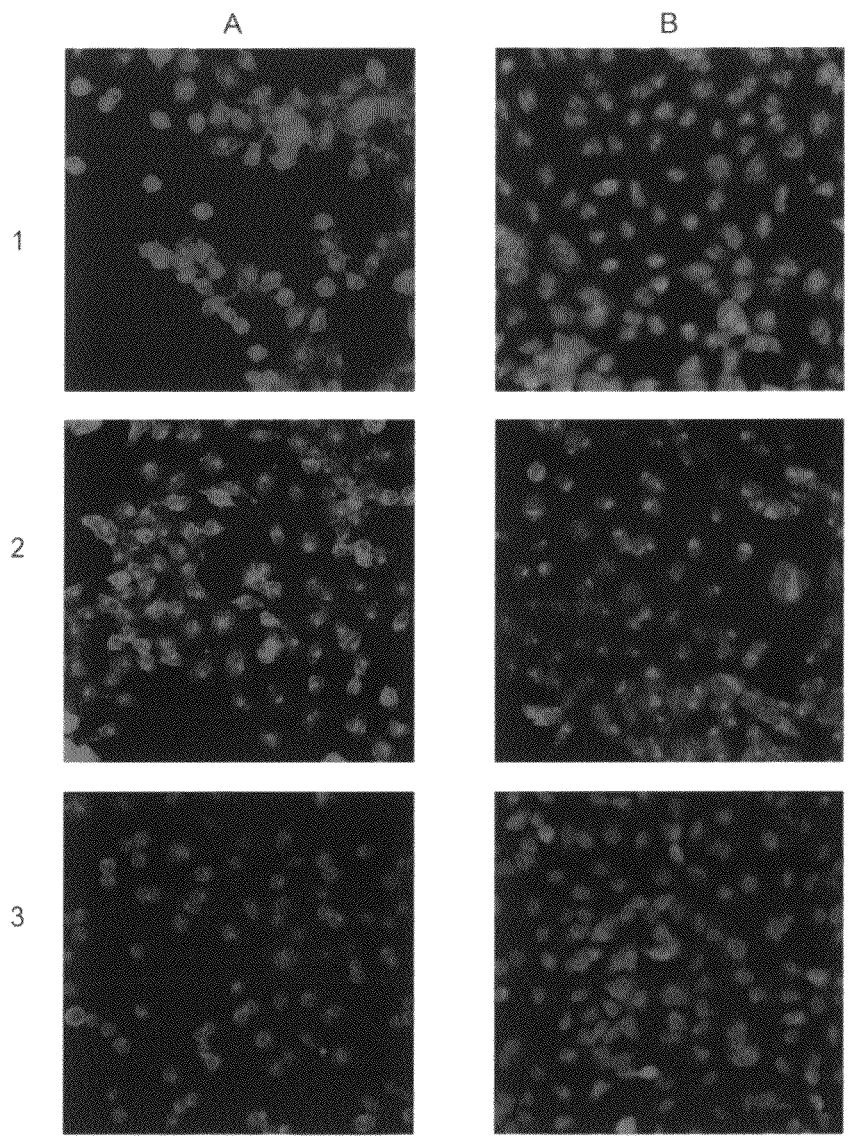
FIG. 36 shows fluorescence images of cells labeled with various phosphine-containing compounds.
Figure 37A:
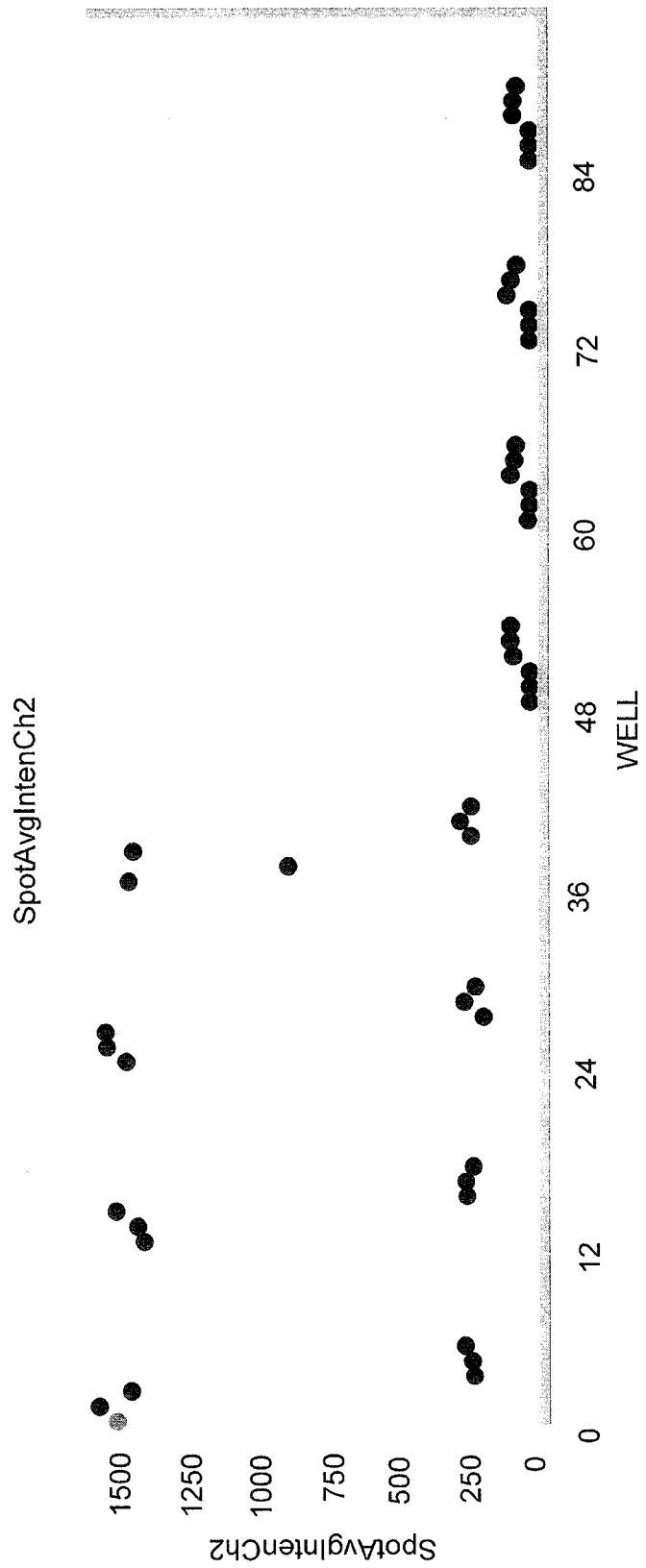
FIG. 37A shows Spot Average Intensity of images of FIG. 36.
Figure 37B:
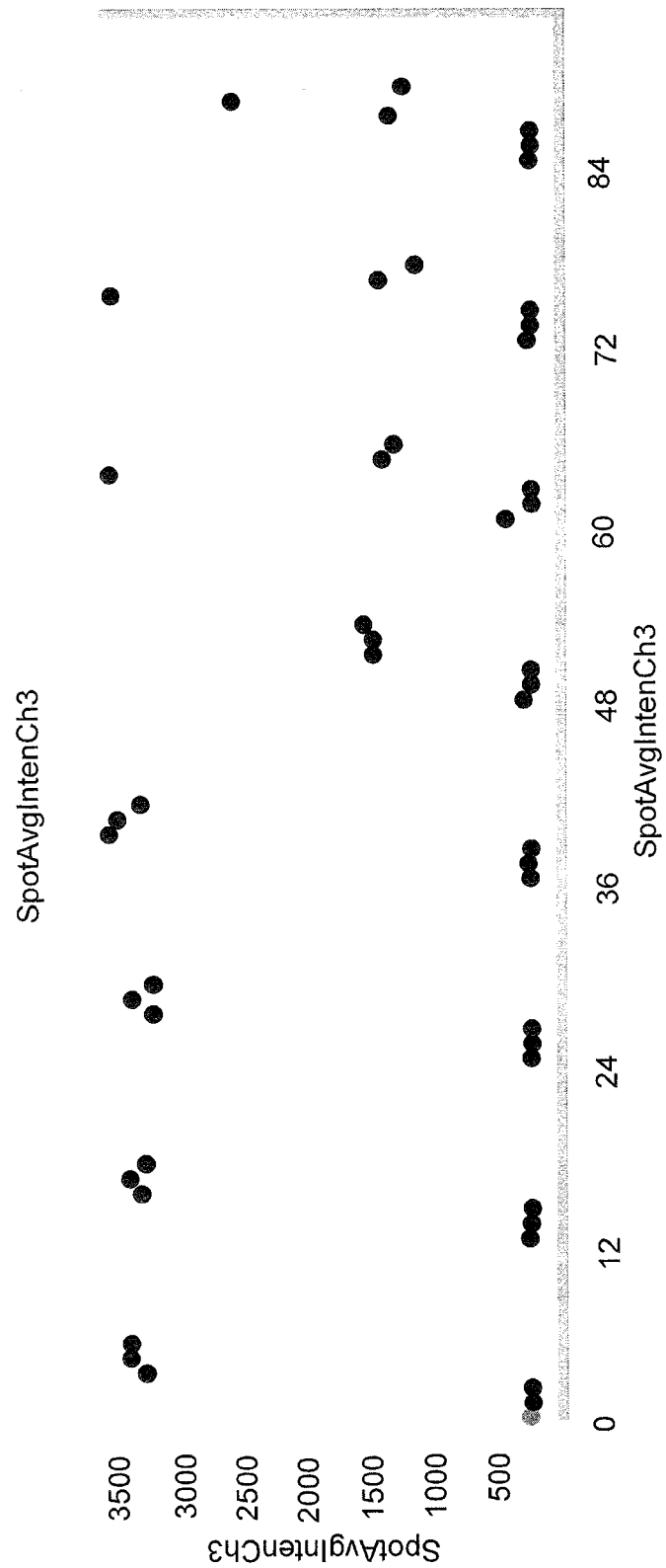
FIG. 37B shows Spot Average Intensity of images of FIG. 36.
Figure 38:
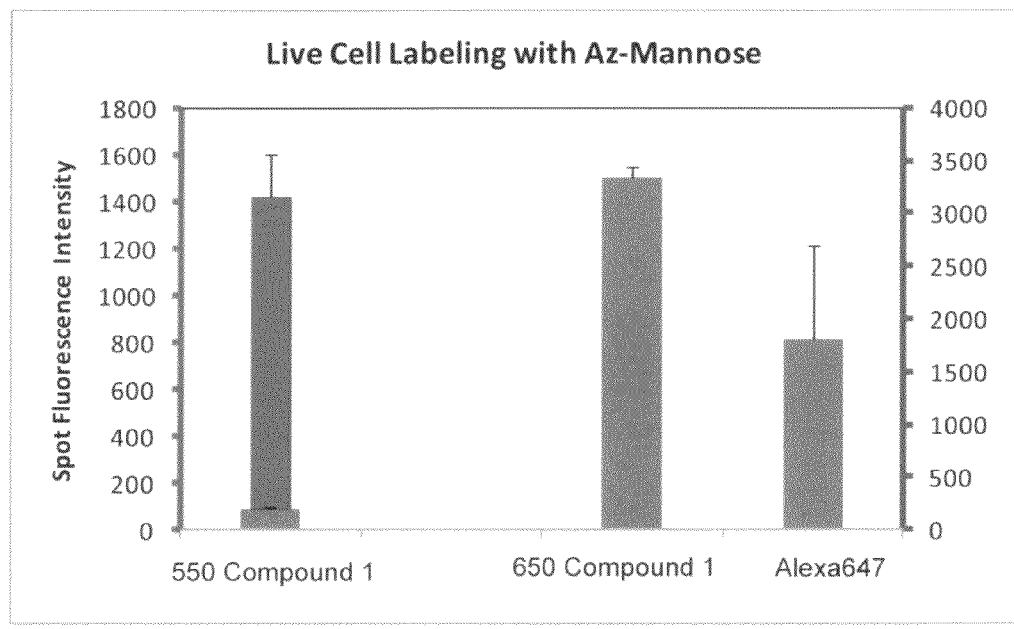
FIG. 38 shows Spot Fluorescence Intensity of the live cell images of FIG. 36.
Figure 39:
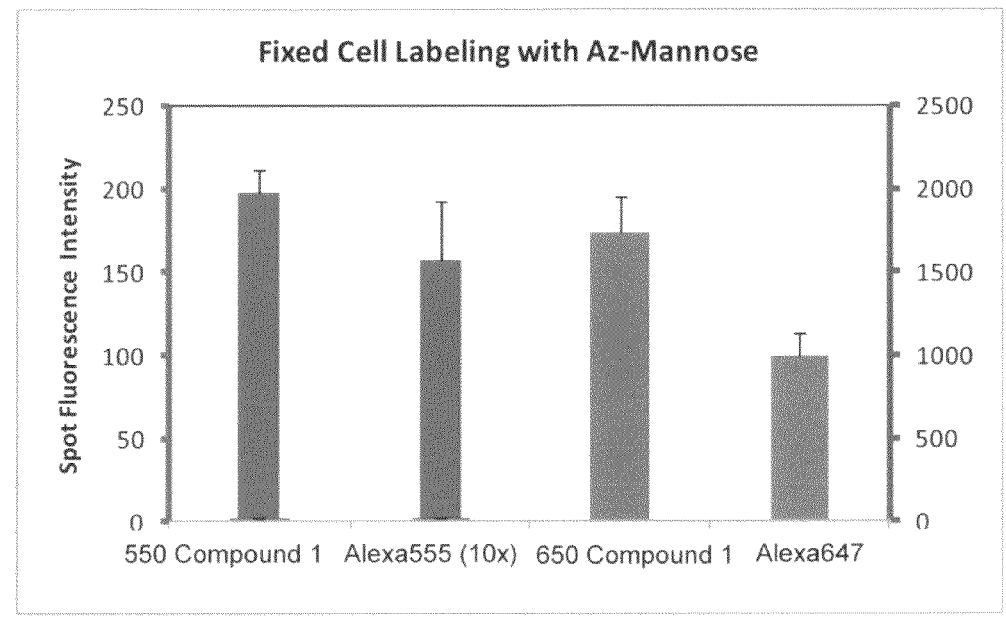
FIG. 39 shows Spot Fluorescence Intensity of the fixed cell images of FIG. 36.

A549 cells, either live (column A) or fixed (column B), were labeled with N-azidoacetyl mannosamine followed by labeling with 550 Compound 1-phosphine (row 1), 650 Compound 1-phosphine (row 2), or Copperless CLICK-iT® using DIBO-Alexa647 (row 3), as shown in FIG. 36. The pattern of specific staining should typically be in the membrane, as seen in live cells with dye-phosphine, unlike the deemed "non-specific" nuclear/whole cells in fixed cells when using the Click iT DIBO Alexa 647. A graph depicting spot average intensity for the live cell images of FIG. 36, is shown for the 550 Compound 1-phosphine labeled cells (FIG. 37A, wells 1-48), the 650 Compound 1-phosphine labeled cells (FIG. 37B, wells 1-48), and the DIBO-Alexa647 labeled cells (FIG. 37B, wells 49-96). A graphical representation of the spot average intensity for the images of FIG. 36 is shown for live (FIG. 38) and fixed (FIG. 39) cells.

Figure 41A:
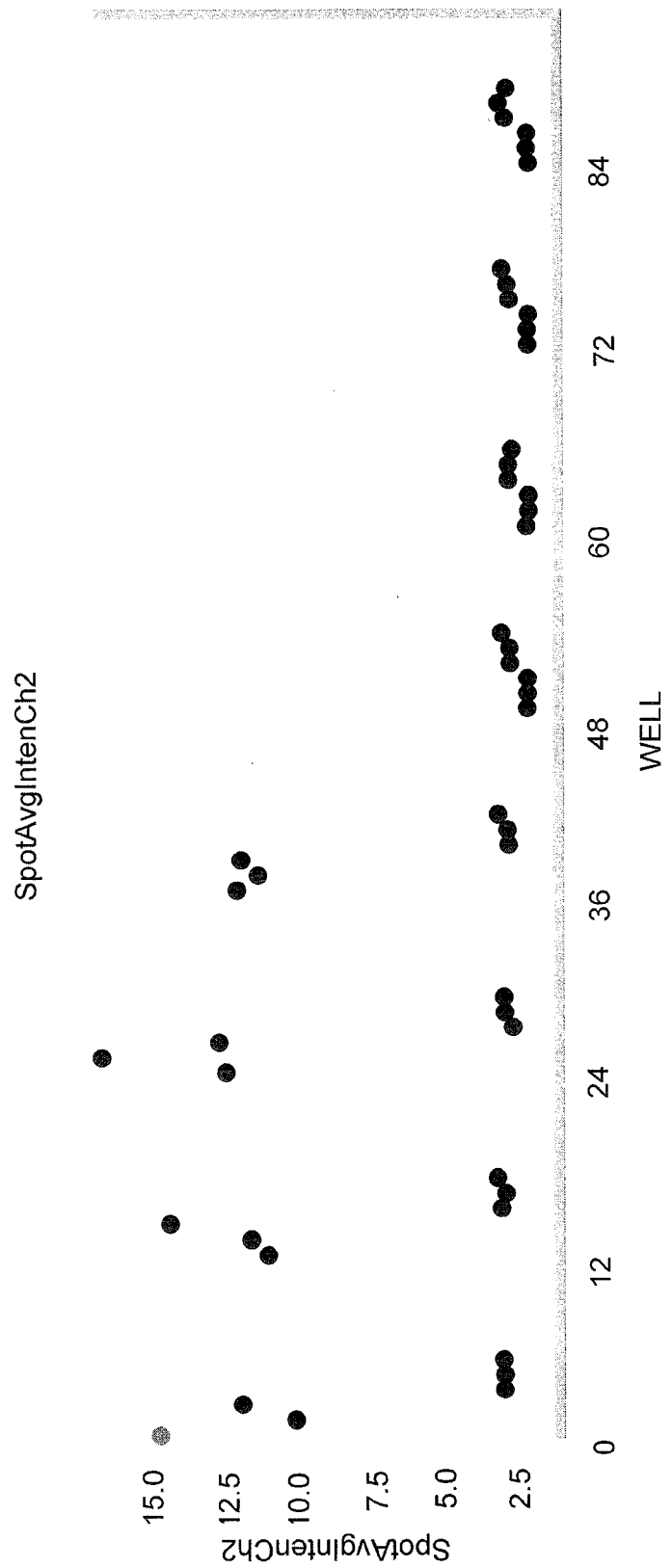
FIG. 41A shows Spot Average Intensity of images of FIG. 40.
Figure 41B:
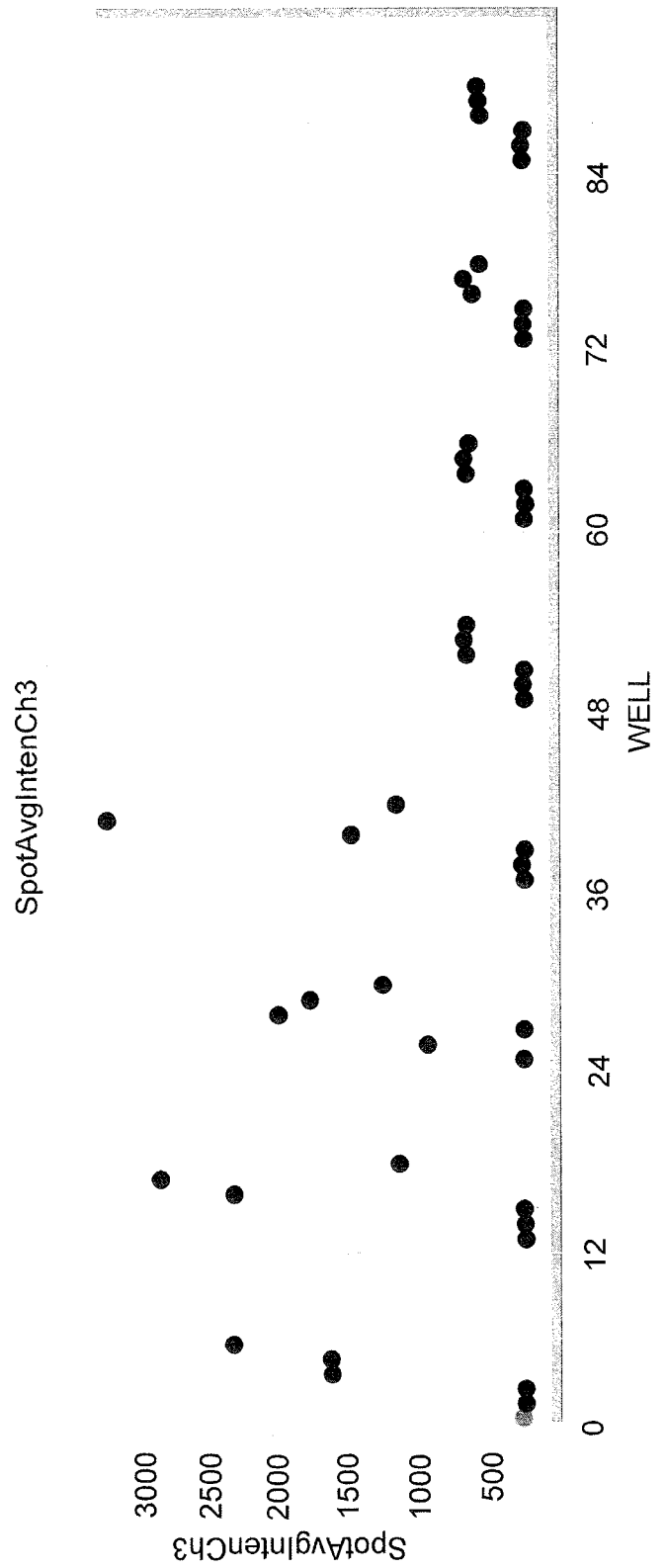
FIG. 41B shows Spot Average Intensity of images of FIG. 40.
Figure 42:
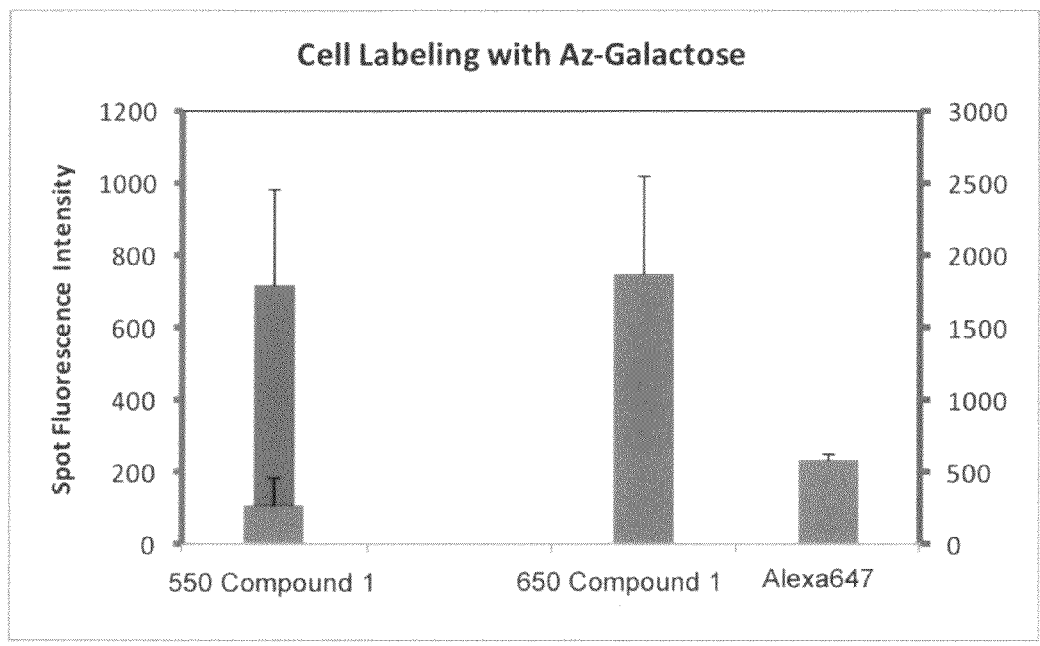
FIG. 42 shows Spot Fluorescence Intensity of the live cell images of FIG. 40.
Figure 43:
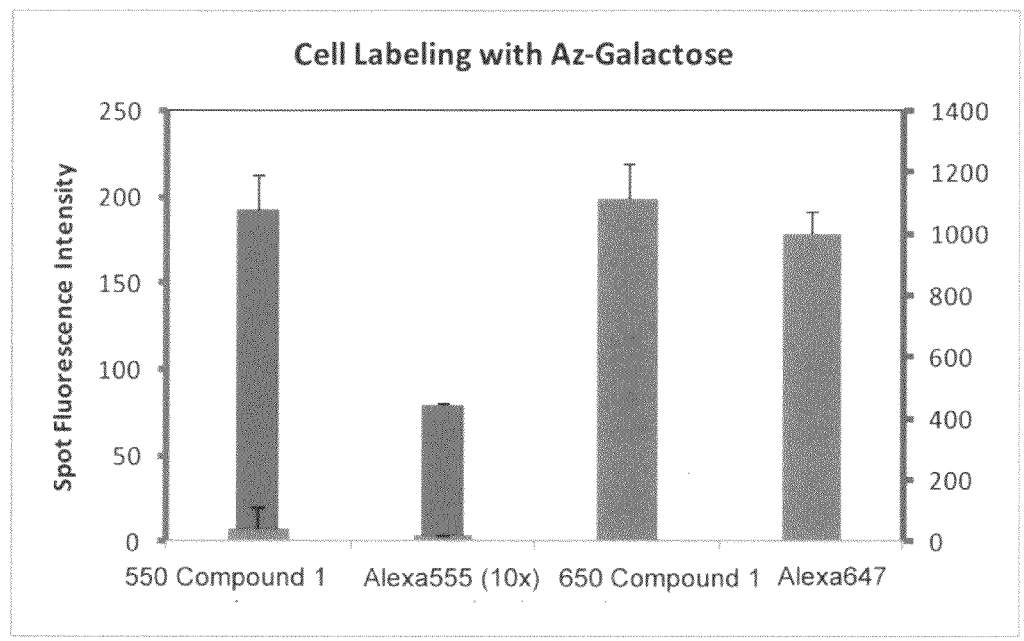
FIG. 43 shows Spot Fluorescence Intensity of the fixed cell images of FIG. 40.

U2OS cells, either live (column A) or fixed (column B), were labeled with N-azidoacetyl galactosamine followed by labeling with 550 Compound 1-phosphine (row 1), 650 Compound 1-phosphine (row 2), or Copperless CLICK-IT® using DIBO-Alexa647 (row 3), as shown in FIG. 40. A graph depicting spot average intensity for the live cell images of FIG. 40, is shown for the 550 Compound 1-phosphine labeled cells (FIG. 41A, wells 1-48), the 650 Compound 1-phosphine labeled cells (FIG. 41B, wells 1-48), and the DIBO-Alexa647 labeled cells (FIG. 41B, wells 49-96). A graphical representation of the spot average intensity for the images of FIG. 40 is shown for labeling live (FIG. 42) and fixed (FIG. 43) cells. As above, the results show that staining in live cells is specific in the membrane, while fixed cells show non-specific staining in the nucleus.

Figure 45A:
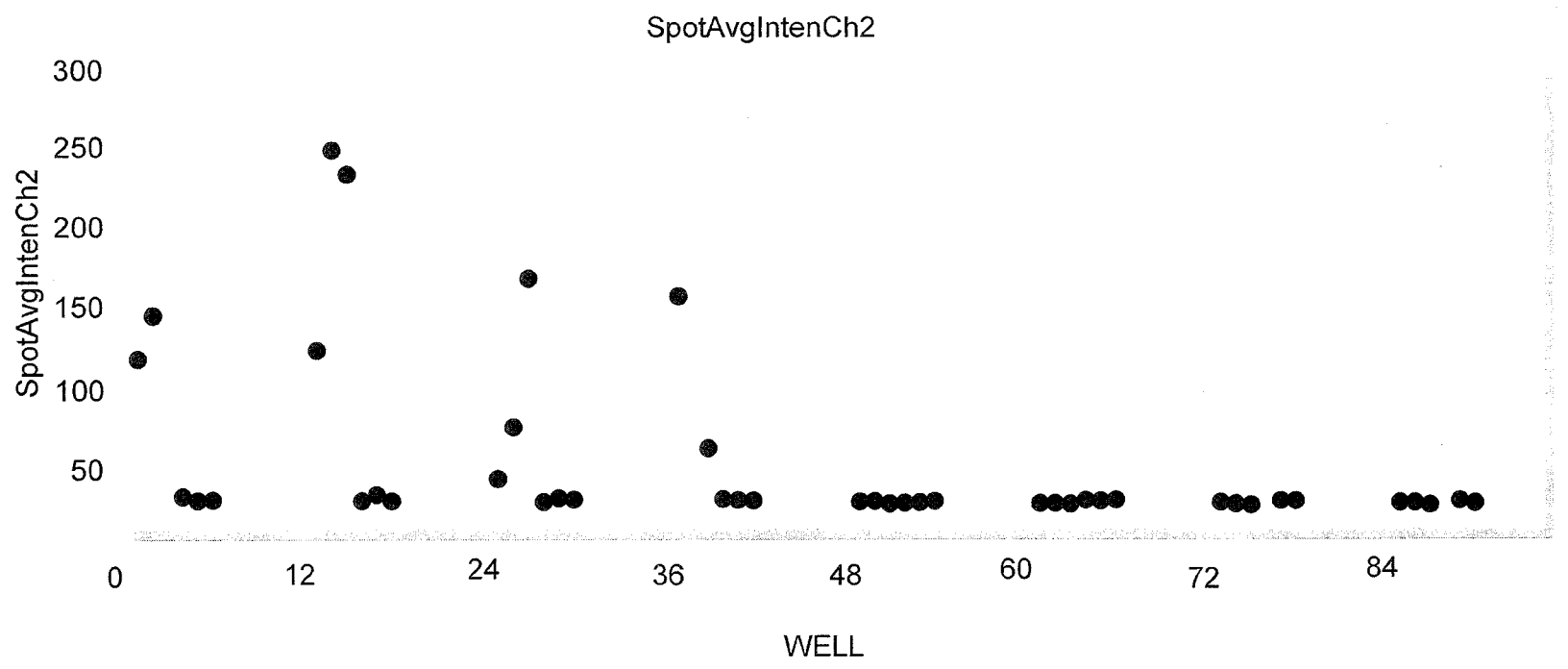
Figure 45B:
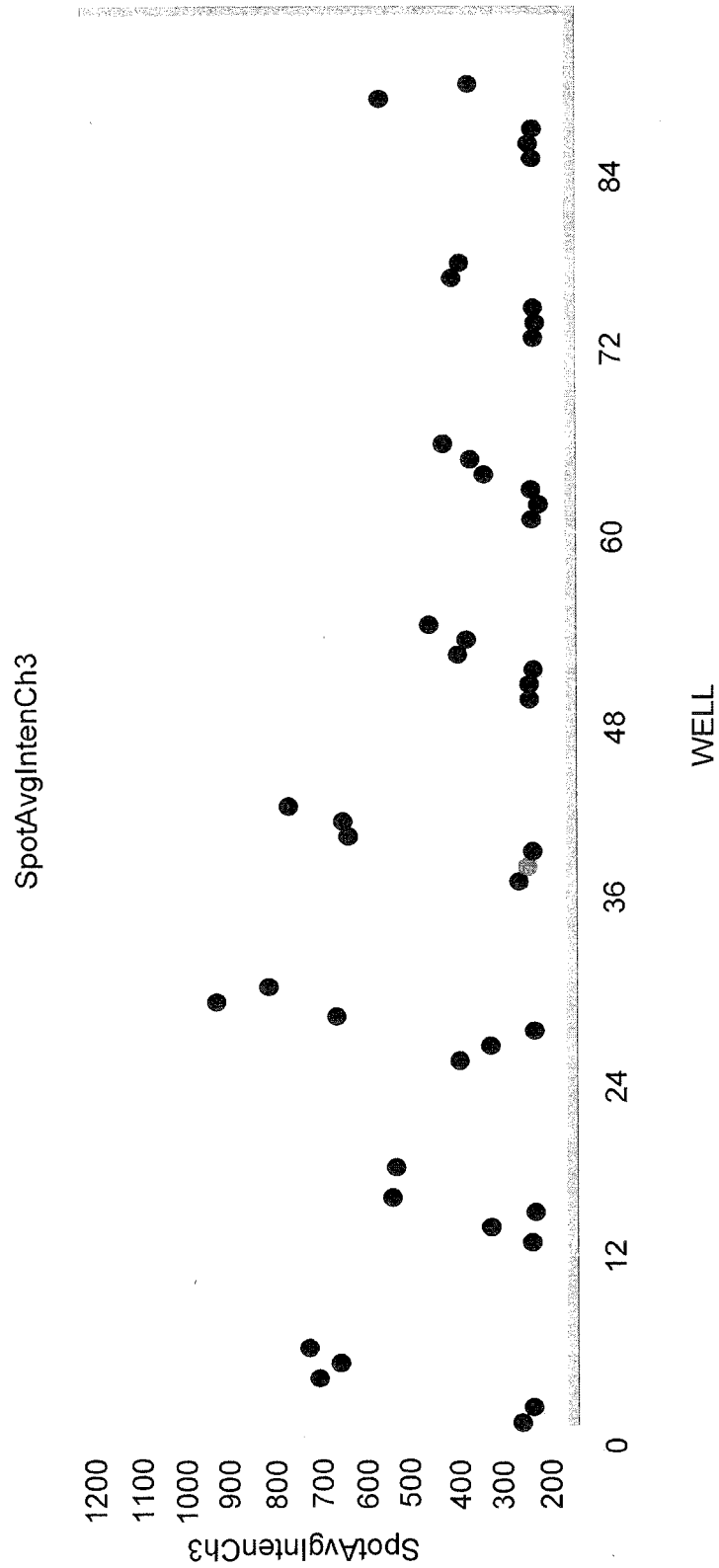
FIG. 45B shows Spot Average Intensity of images of FIG. 44.
Figure 46:
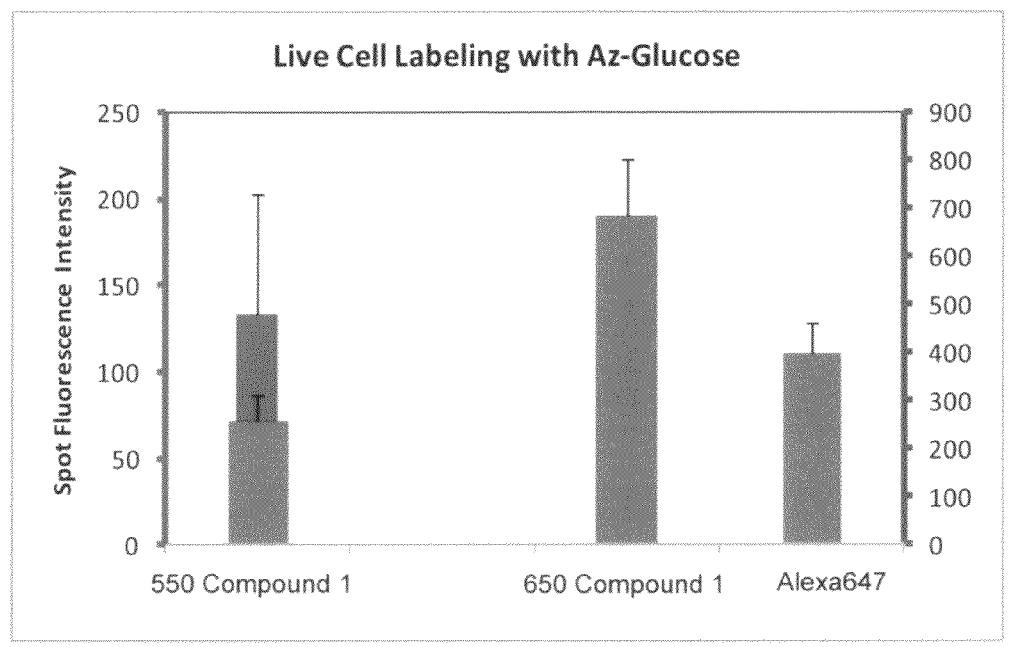
FIG. 46 shows Spot Fluorescence Intensity of the live cell images of FIG. 44.
Figure 47:
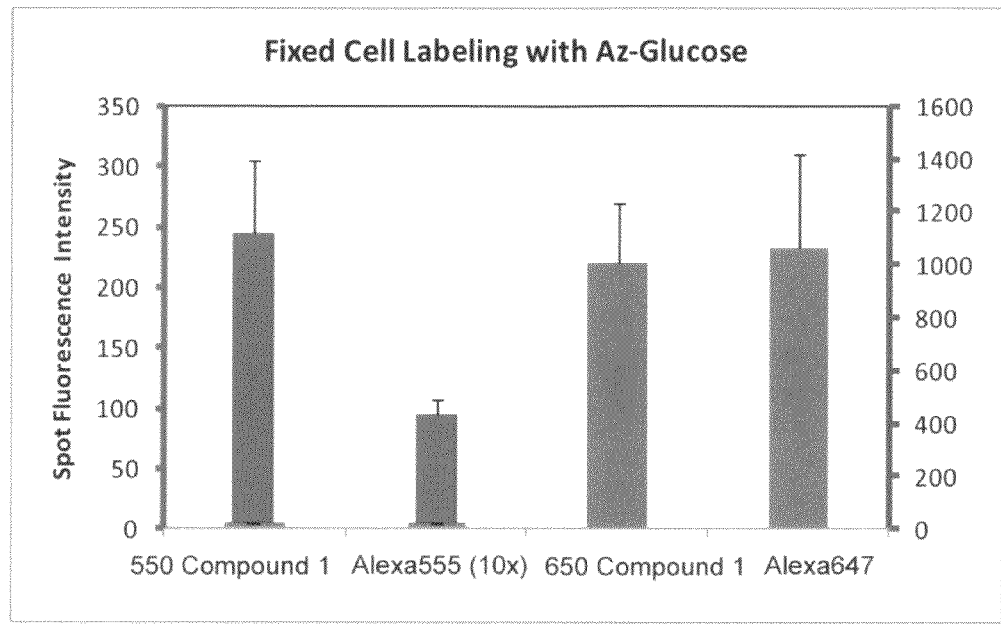
FIG. 47 shows Spot Fluorescence Intensity of the fixed cell images of FIG. 44.

U2OS cells, either live (column A) or fixed (column B), were labeled with N-azidoacetyl glucosamine followed by labeling with 550 Compound 1-phosphine (row 1), 650 Compound 1-phosphine (row 2), or Copperless CLICK-iT® using DIBO-Alexa647 (row 3), as shown in FIG. 44. A graph depicting spot average intensity for the live cell images of FIG. 44, is shown for the 550 Compound 1-phosphine labeled cells (FIG. 45A, wells 1-48), the 650 Compound 1-phosphine labeled cells (FIG. 45B, wells 1-48), and the DIBO-Alexa647 labeled cells (FIG. 45B, wells 49-96). A graphical representation of the spot average intensity for the images of FIG. 44 is shown for labeling live (FIG. 46) and fixed (FIG. 47) cells. As above, the results show that in live cells, 650 Compound 1-phosphine was better than Alexa647-DIBO CLICK-IT® labeling.

Figure 48:
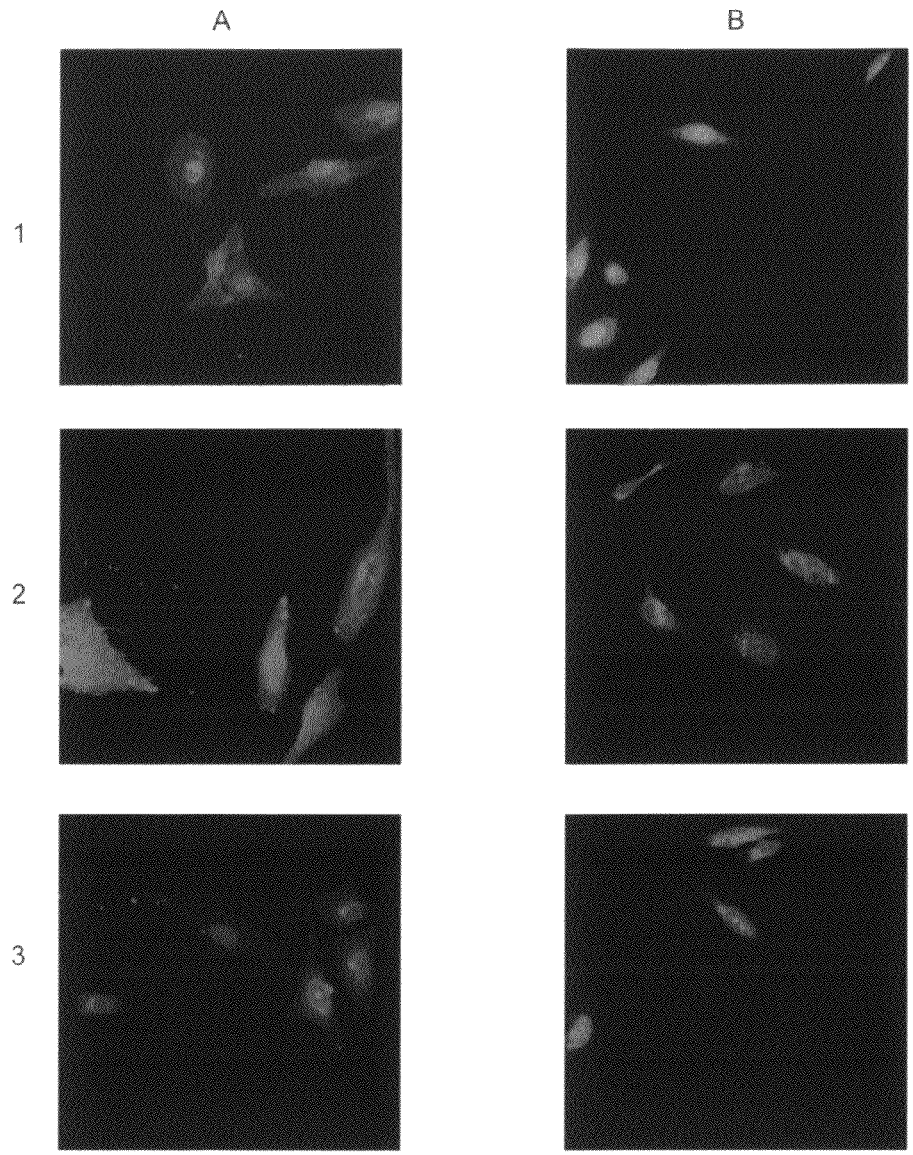
FIG. 48 shows fluorescence images of cells labeled with various phosphine-containing compounds.
Figure 49A:
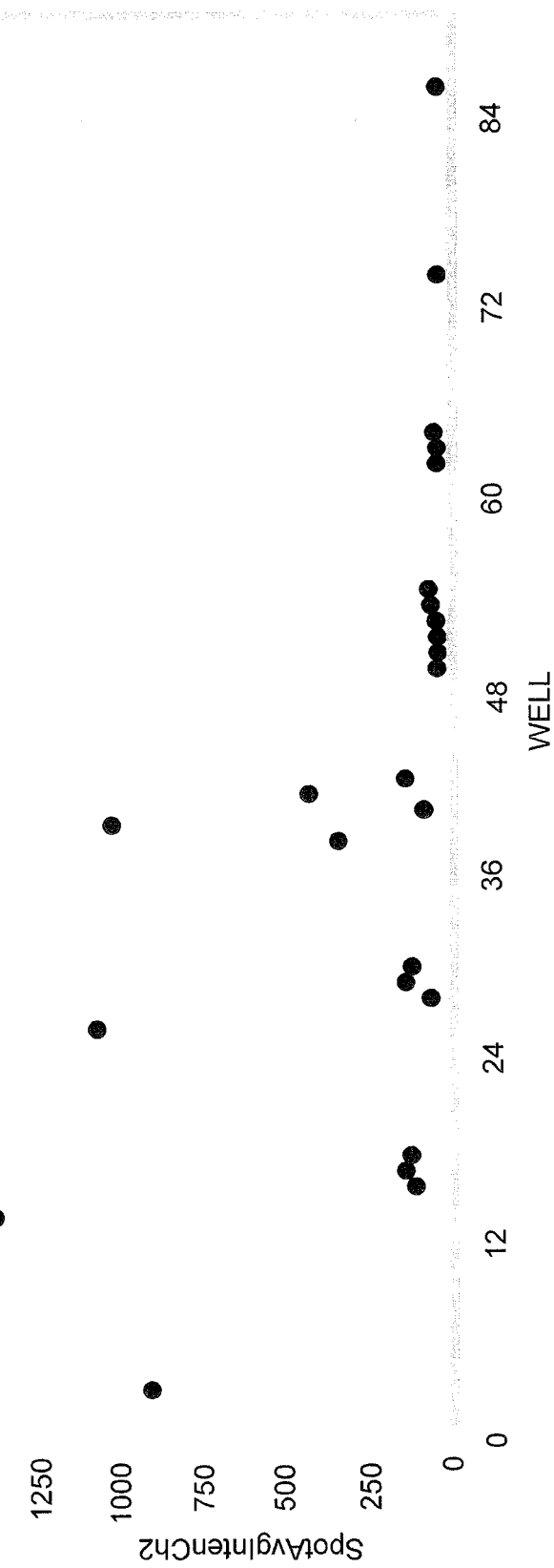
FIG. 49A shows Spot Average Intensity of images of FIG. 48.
Figure 50:
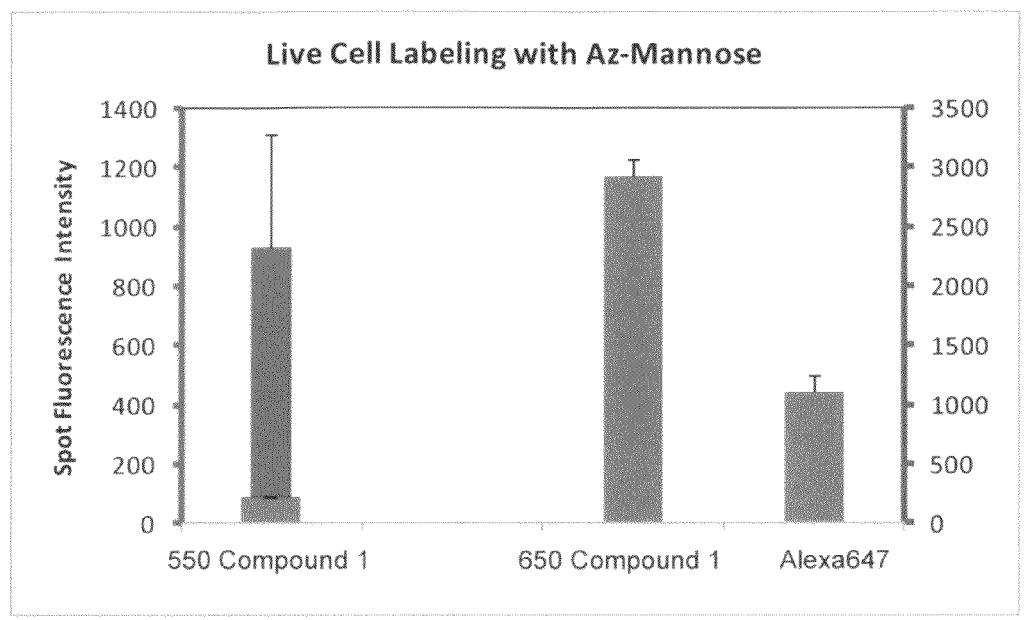
FIG. 50 shows Spot Fluorescence Intensity of the live cell images of FIG. 48.
Figure 51:
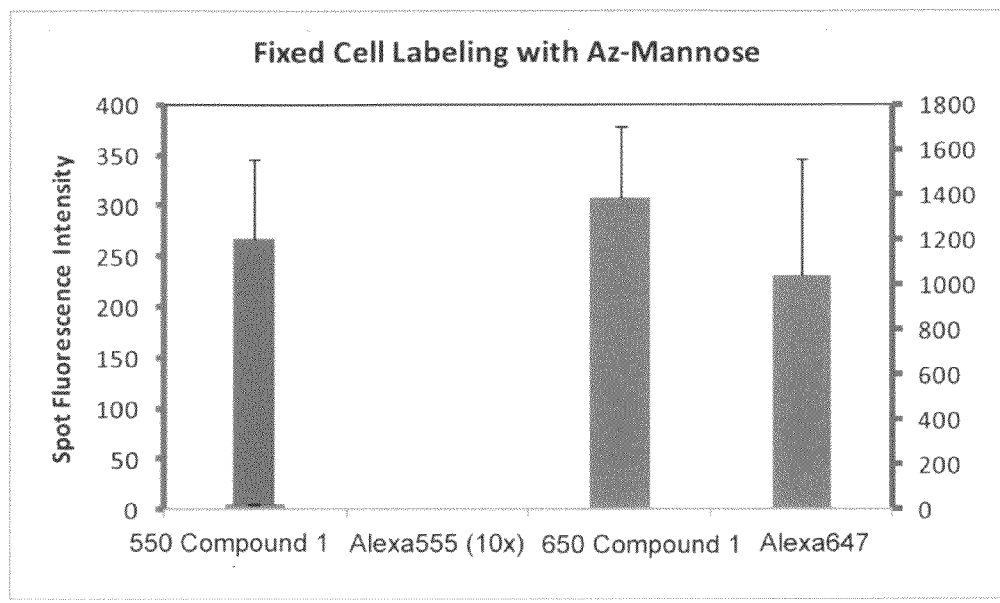
FIG. 51 shows Spot Fluorescence Intensity of the fixed cell images of FIG. 48.

U2OS cells, either live (column A) or fixed (column B), were labeled with N-azidoacetyl mannosamine followed by labeling with 550 Compound 1-phosphine (row 1), 650 Compound 1-phosphine (row 2), or Copperless CLICK-iT® using DIBO-Alexa647 (row 3), as shown in FIG. 48. A graph depicting spot average intensity for the live cell images of FIG. 48, is shown for the 550 Compound 1-phosphine labeled cells (FIG. 49A, wells 1-48), the 650 Compound 1-phosphine labeled cells (FIG. 49B, wells 1-48), and the DIBO-Alexa647 labeled cells (FIG. 49B, wells 49-96). A graphical representation of the spot average intensity for the images of FIG. 48 is shown for labeling live (FIG. 50) and fixed (FIG. 51) cells. As above, the results show that in live cells, 650 Compound 1-phosphine was better than Alexa647-DIBO CLICK-IT® labeling. Cell loss can be indicative of cell death due to toxicity, potentially related to copper oxidation in Alexa 555.

Figure 52:
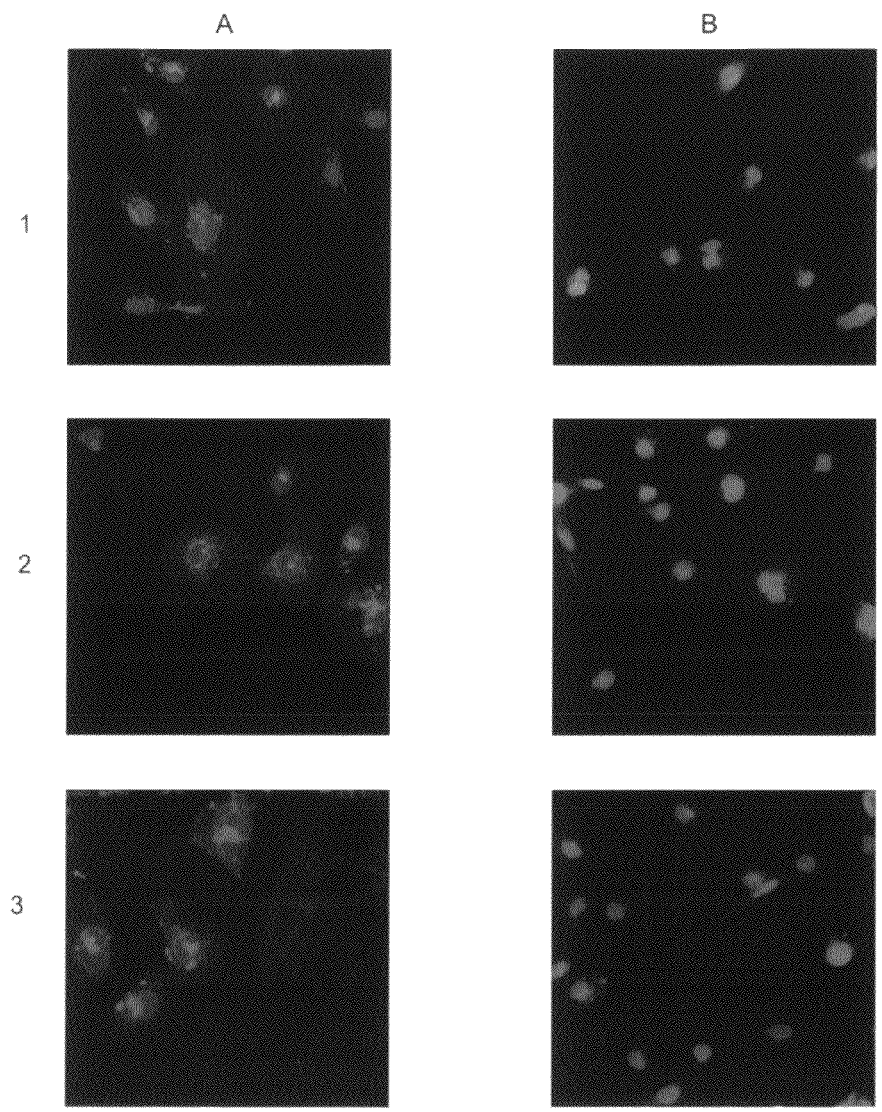
FIG. 52 shows fluorescence images of cells labeled with various phosphine-containing compounds.
Figure 53:
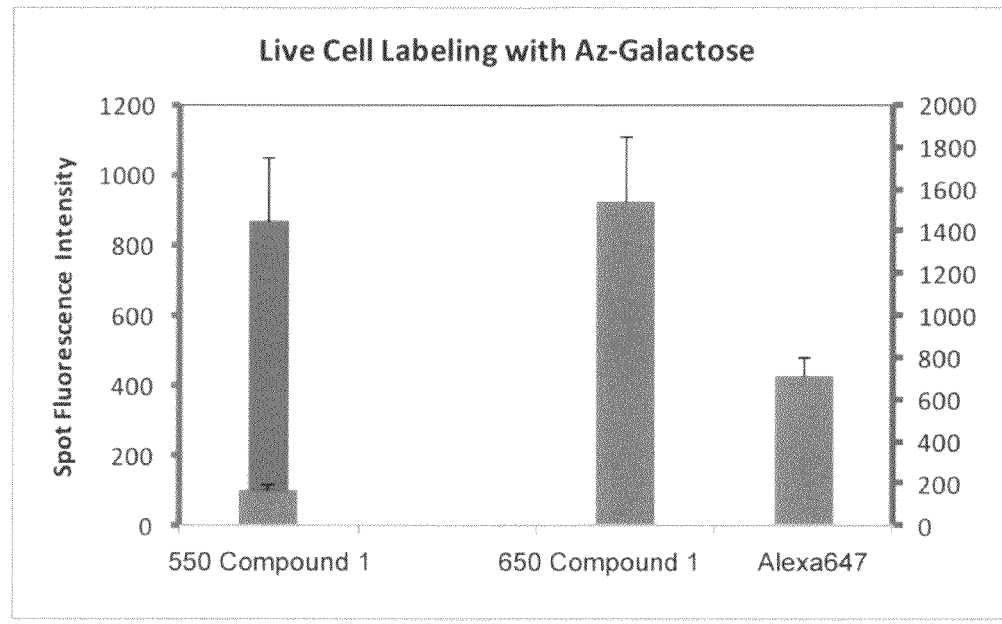
FIG. 53 shows Spot Fluorescence Intensity of the live cell images of FIG. 52.
Figure 54:
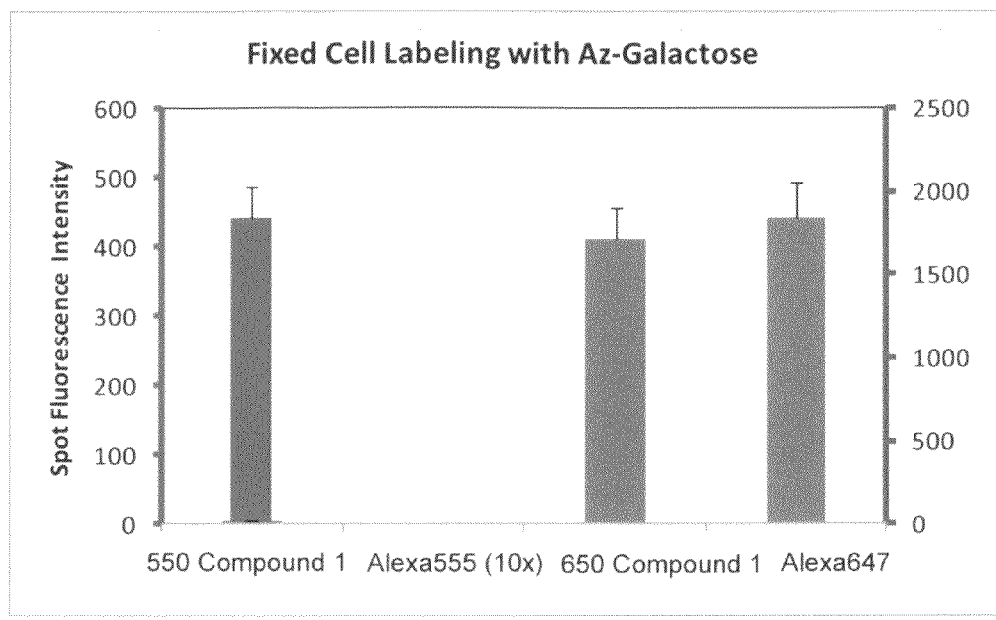
FIG. 54 shows Spot Fluorescence Intensity of the fixed cell images of FIG. 52.

HK2 cells, either live (column A) or fixed (column B), were labeled with N-azidoacetyl galactosamine followed by labeling with 550 Compound 1-phosphine (row 1), 650 Compound 1-phosphine (row 2), or Copperless CLICK-iT® using DIBO-Alexa647 (row 3), as shown in FIG. 52. A graphical representation of the spot average intensity for the images of FIG. 52 is shown for labeling live (FIG. 53) and fixed (FIG. 54) cells. As above, the results show that in live cells, 650 Compound 1-phosphine was better than Alexa647-DIBO CLICK-iT® labeling.

Figure 55:
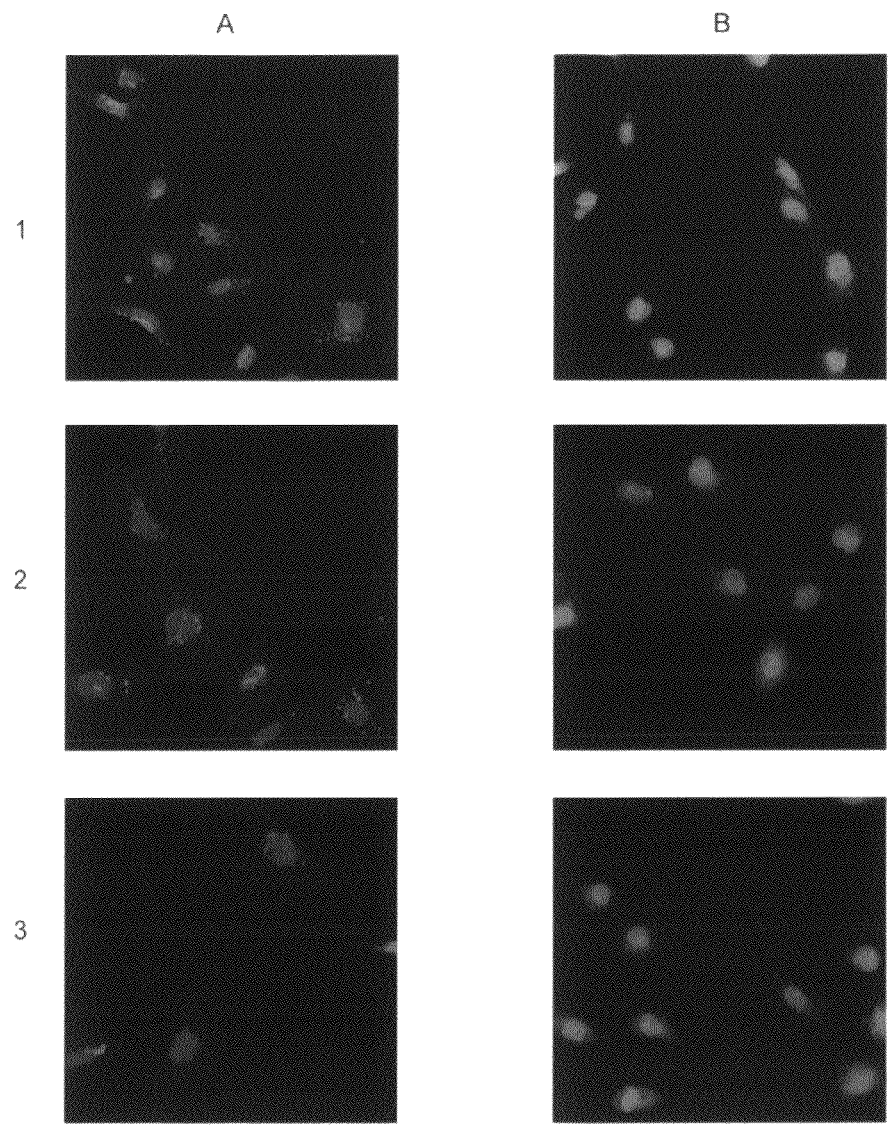
FIG. 55 shows fluorescence images of cells labeled with various phosphine-containing compounds.
Figure 56:
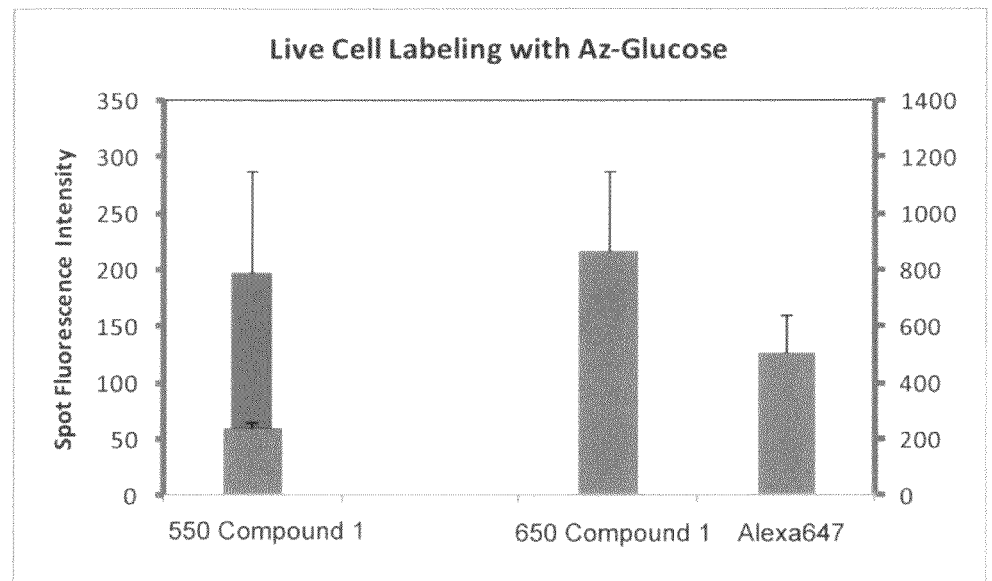
FIG. 56 shows Spot Fluorescence Intensity of the live cell images of FIG. 55.
Figure 57:
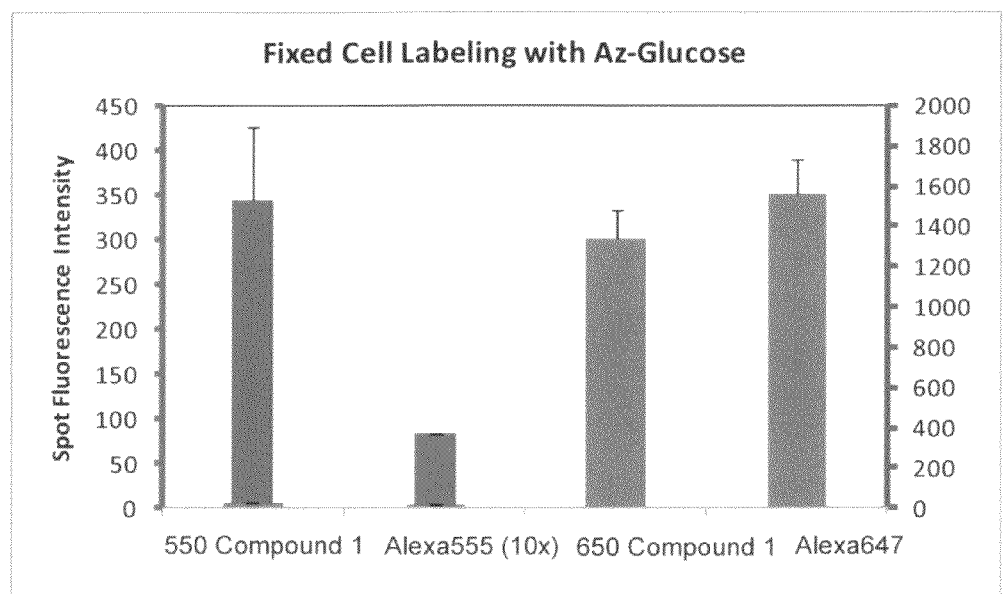
FIG. 57 shows Spot Fluorescence Intensity of the fixed cell images of FIG. 55.

HK2 cells, either live (column A) or fixed (column B), were labeled with N-azidoacetyl glucosamine followed by labeling with 550 Compound 1-phosphine (row 1), 650 Compound 1-phosphine (row 2), or Copperless CLICK-iT® using DIBO-Alexa647 (row 3), as shown in FIG. 55. A graphical representation of the spot average intensity for the images of FIG. 55 is shown for labeling live (FIG. 56) and fixed (FIG.

57) cells. As above, the results show that in live cells, 650 Compound 1-phosphine was better than Alexa647-DIBO CLICK-iT® labeling.

Figure 59:
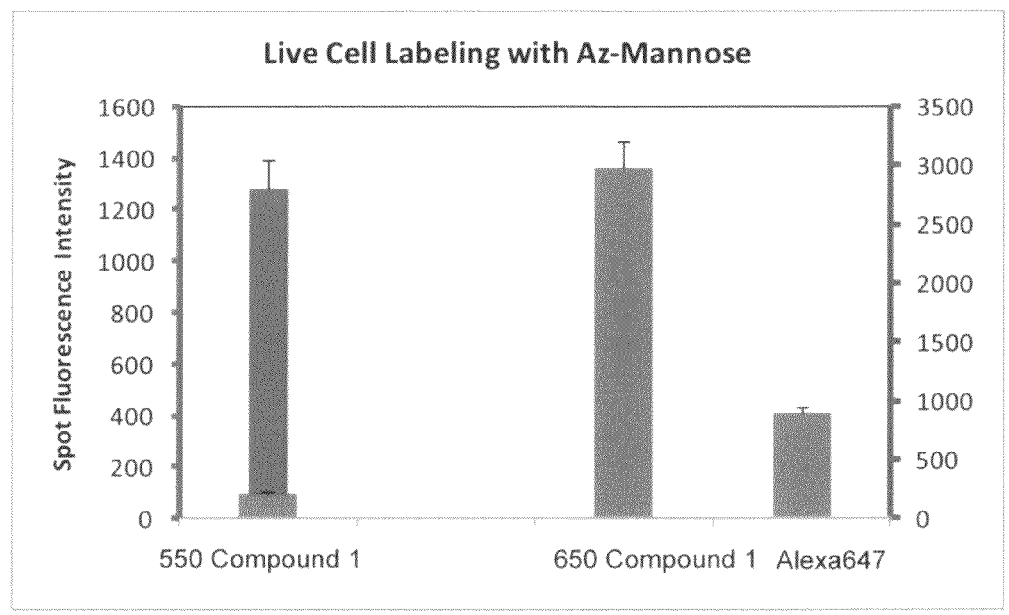
FIG. 59 shows Spot Fluorescence Intensity of the live cell images of FIG. 58.
Figure 60:
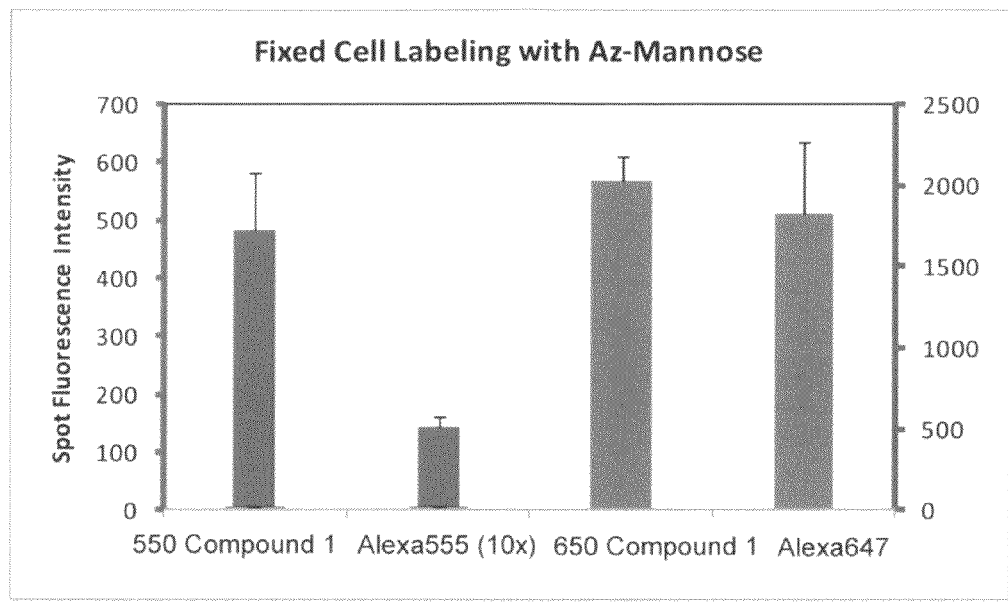
FIG. 60 shows Spot Fluorescence Intensity of the fixed cell images of FIG. 58.

HK2 cells, either live (column A) or fixed (column B), were labeled with N-azidoacetyl mannosamine followed by labeling with 550 Compound 1-phosphine (row 1), 650 Compound 1-phosphine (row 2), or Copperless CLICK-iT® using DIBO-Alexa647 (row 3), as shown in FIG. 58. A graphical representation of the spot average intensity for the images of FIG. 58 is shown for live cell labeling (FIG. 59) and for fixed cell labeling (FIG. 60). As above, the results show that in live cells, 650 Compound 1-phosphine was better than Alexa647-DIBO CLICK-iT® labeling.

EXAMPLE 25

Figure 61:
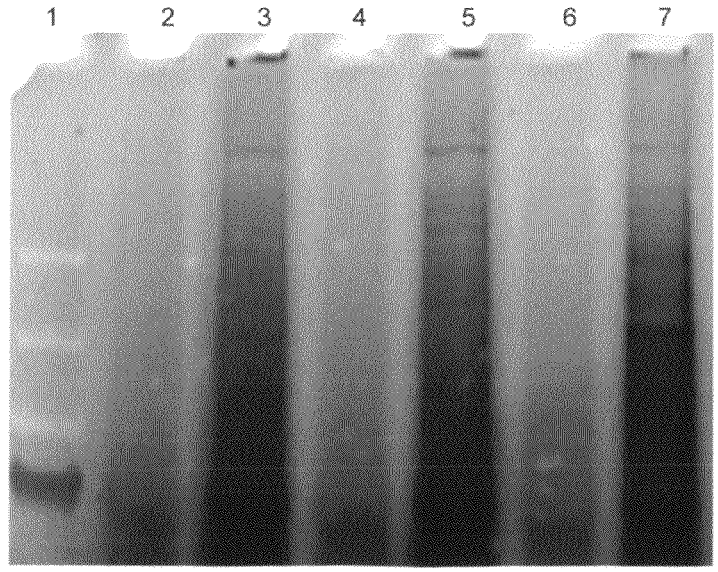
FIG. 61 shows SDS-PAGE of cell lysates labeled with various phosphine-containing compounds.

The inventive and commercial compounds were examined in A549 cell lysate labeling experiments using azido-sugars. Cell extracts were prepared from A549 incubated with azido-sugar N-azidoacetylgalactosamine (ManNAz), N-azidoacetylglucosamine (GlcNAz) or N-azidoacetylmannosamine (GalNAz). The cell extracts were incubated with either 550 Compound 1-phosphine, 650 Compound 1-phosphine, CLICK-iT® Alexa555-Alkyne, or CLICK-IT® Alexa Fluor 647 DIBO Alkyne and analyzed by SDS-PAGE. The resulting lysates were separated by electrophoresis. 10 µg protein was loaded onto a PAGE gel (4-12% Bis-Tris gel). FIG. 61 shows protein staining viewed using the Typhoon 9410 imager showing the conjugation of azido sugars from the cell extract labeled with either N-azidoacetyl galactosamine (Az-GalNAc; lanes 2 and 3), N-azidoacetyl glucosamine (Az-GlcNAc; lanes 4 and 5), or N-azidoacetyl mannosamine (Az-ManNAc; lanes 6 and 7) and conjugated with either CLICK-iT® Alexa555-Alkyne (lanes 2, 4, and 6) or 550 Compound 1-phosphine (lanes 3, 5, and 7), along with a molecular weight ladder (lane 1), as shown in FIG. 61.

Figure 62:
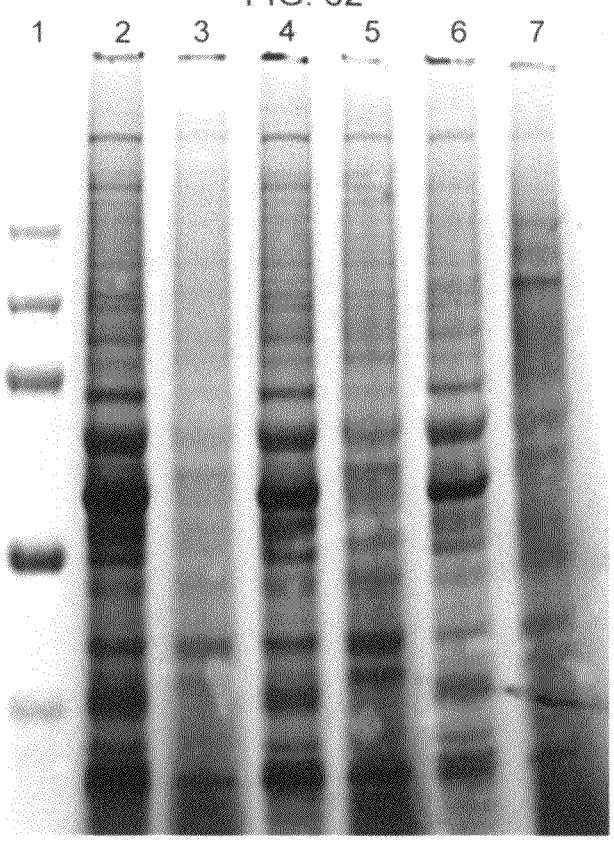
FIG. 62 shows SDS-PAGE of cell lysates labeled with various phosphine-containing compounds.

The resulting lysates were separated by electrophoresis. Protein staining is viewed using the Typhoon 9410 imager after labeling with the dyes that had been labeled with either N-azidoacetyl galactosamine (Az-GalNAc; lanes 2 and 3), N-azidoacetyl glucosamine (Az-GlcNAc; lanes 4 and 5), or N-azidoacetyl mannosamine (Az-ManNAc; lanes 6 and 7) and conjugated with either DIBO Alexa647 (lanes 2, 4, and 6) or 650 Compound 1-phosphine (lanes 3, 5, and 7), along with a molecular weight ladder (lane 1), as shown in FIG. 62. The samples incubated with 650 Compound 1-phosphine showed a different labeling pattern for each of the three incorporated azido-sugars, demonstrating that different types of glycosylation were detected specifically.

Figure 63:
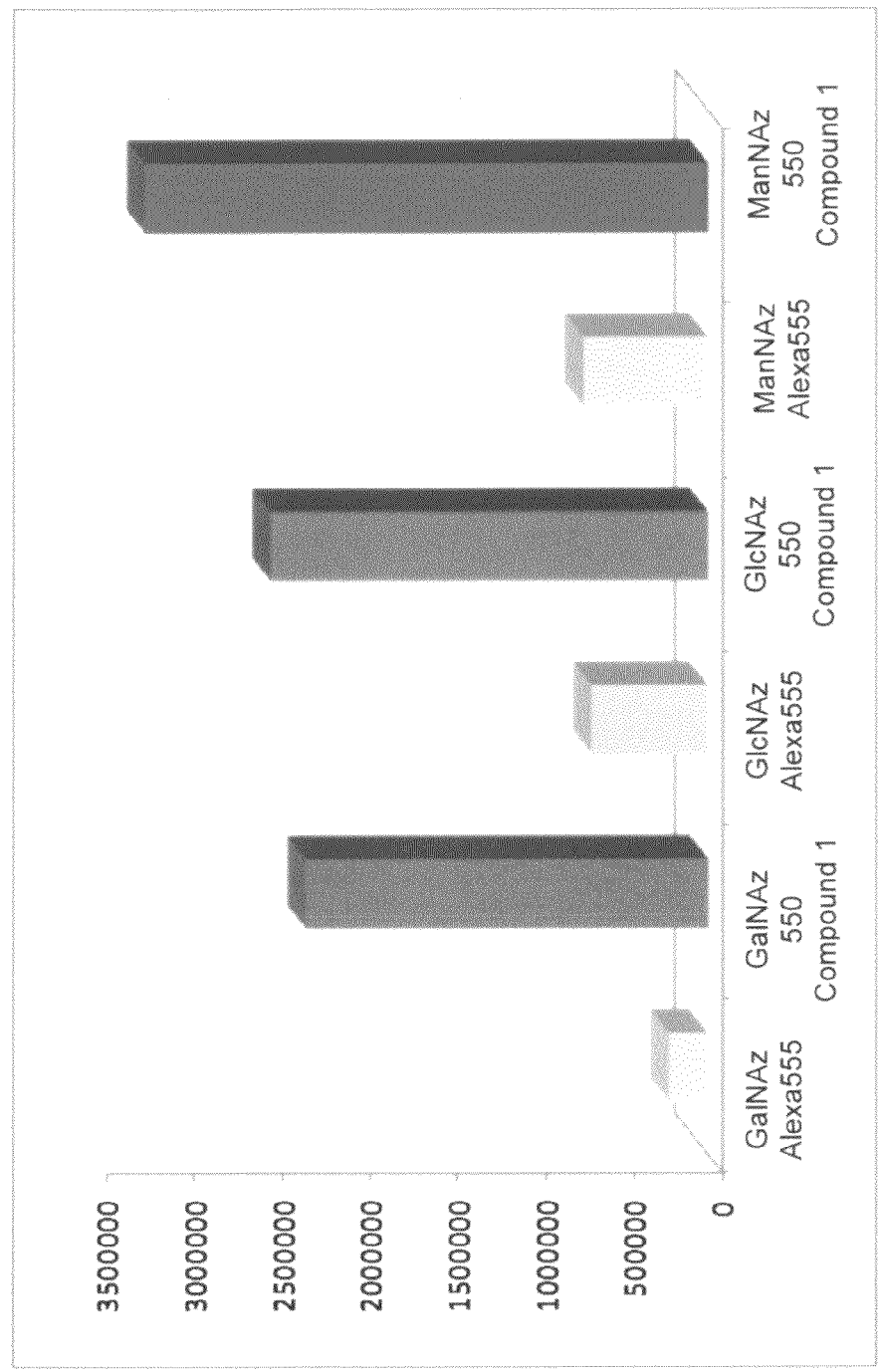
FIG. 63 shows band intensity of the gel image of FIG. 61.
Figure 64:
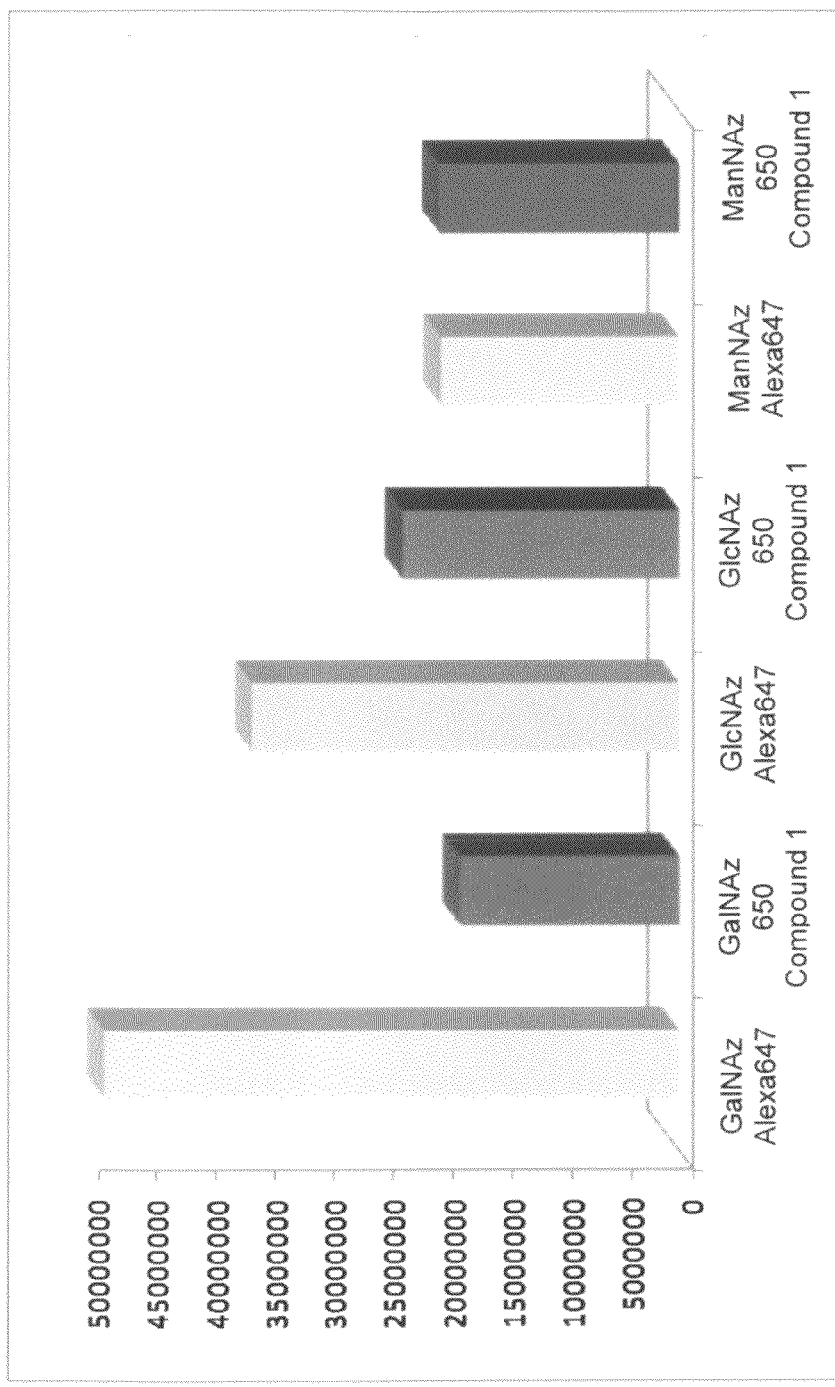
FIG. 64 shows band intensity of the gel image of FIG. 62.

FIGS. 63-64 graphically represent band intensity of FIGS. 61-62. FIG. 63 lanes 1-6 correspond to Gal-Alexa 555, Gal-550 Compound 1, Glc-Alexa 555, Glc-550 Compound 1, Man-Alexa 555, Man-550 Compound 1, respectively. FIG. 64 lanes 1-6 correspond to Gal-Alexa 647, Gal-650 Compound 1, Glc-Alexa 647, Glc-650 Compound 1, Man-Alexa 647, Man-650 Compound 1, respectively. Relative fluorescence intensity for the gel image of FIG. 61 comparing Alexa555 (copper) and 550 Compound 1-phosphine (FIG. 63) and for the gel image of FIG. 62 comparing Alexa647 (copper-less) and 650 Compound 1-phosphine (FIG. 64). Results shows that 550 Compound 1-phosphine was better than CLICK-iT® Alexa 555-alkyne.

EXAMPLE 26

Figure 65A:
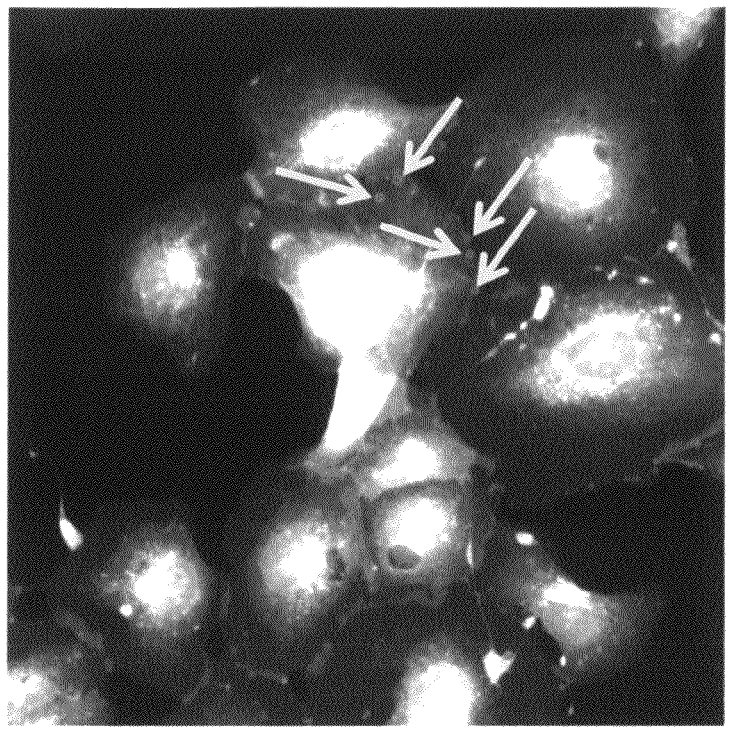
FIG. 65A shows a fluorescence image of a cell showing secretory vesicle labeling with a phosphine-containing compound.
Figure 65B:
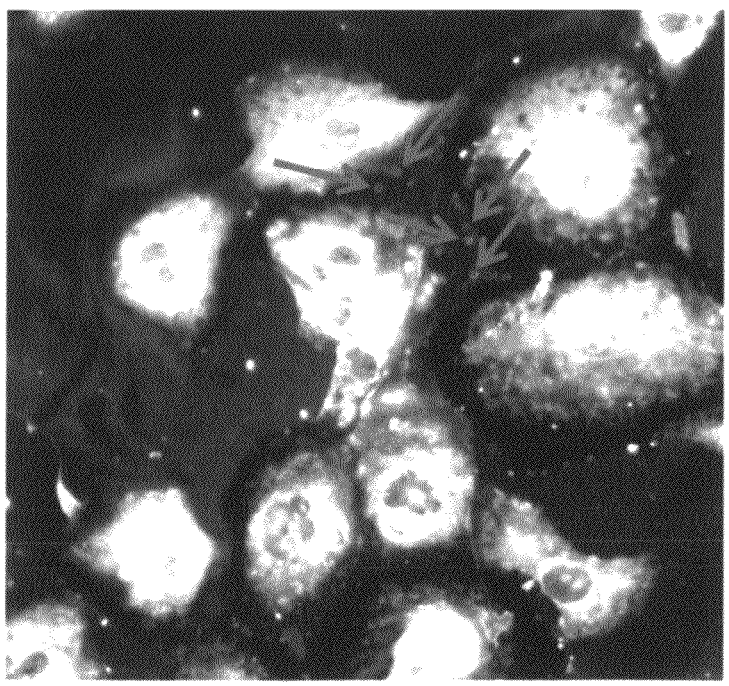
FIG. 65B shows a fluorescence image of a cell showing co-localization of a secretory protein with the image of FIG. 65A.
Figure 66A:
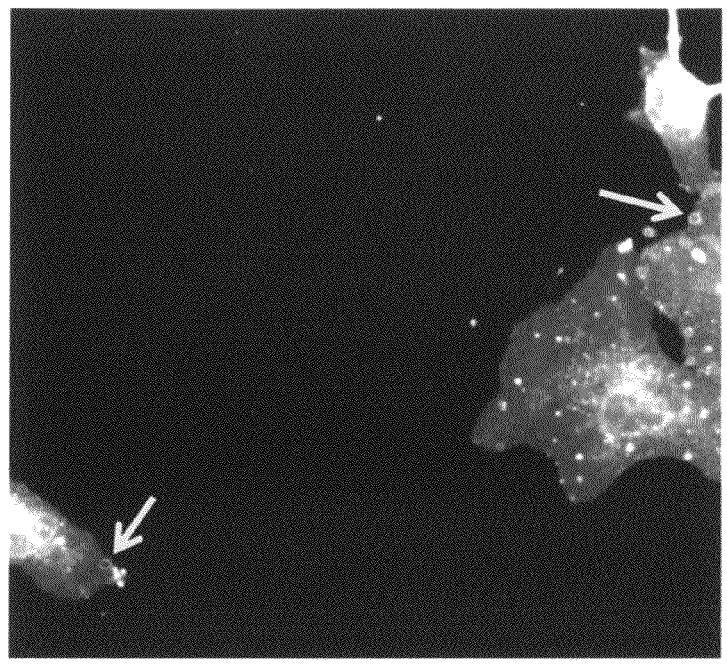
FIG. 66A shows a fluorescence image of a cell showing secretory vesicle labeling with a phosphine-containing compound.
Figure 66B:
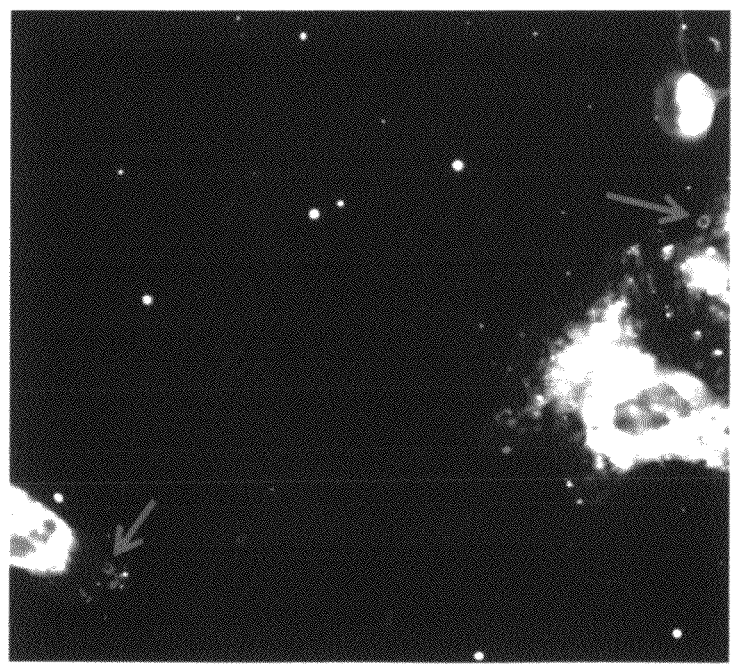
FIG. 66B shows a fluorescence image of a cell showing co-localization of a secretory protein with the image of FIG. 66A.

The inventive and commercial compounds were used to label secretory vesicles in various cell types using azido-sugars. Labeling all cell types (HK2, A549, and U2OS cells) showed successful secretory vesicle staining with N-azidoacetyl mannosamine (Az-ManNAc) and conjugation with 650 Compound 1-phosphine resulted in labeling of secretory vesicles, as shown in FIGS. 65A and 66A (yellow arrows). Co-localization of Man-650 Compound 1-phosphine, and this labeling was co-localized with PGP9.5, a secreted protein, as shown in FIGS. 65B and 66B (red arrows).

EXAMPLE 27

Figure 67:
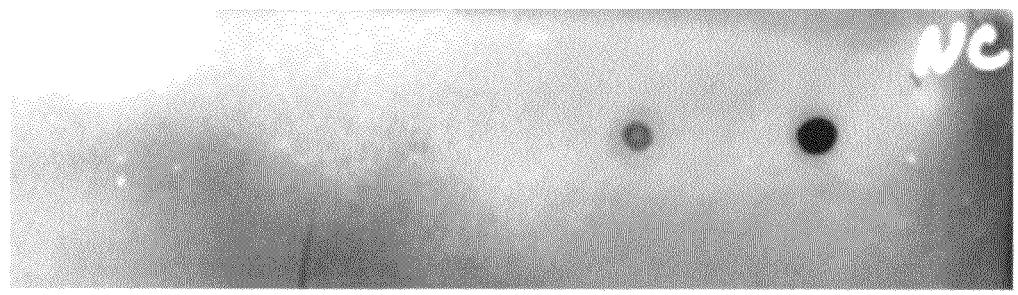
FIG. 67 shows protein detection on nitrocellulose (NC) using a phosphine-containing compound.

The inventive compounds were used in direct protein labeling on nitrocellulose (NC). As shown in FIG. 67, the inventive phosphine-containing compounds detect protein at nanogram level. It is also likely that blocking would reduce the background to achieve better sensitivity.

Overall, 550 Compound 1- and 650 Compound 1-phosphines performed equal to or better than DyLight 549- and DyLight 649-phosphines, respectively. In live cell labeling, the inventive phosphines outperformed the Copperless DIBO-Alexa Fluor CLICK-iT® reaction. In fixed cell labeling, the inventive phosphines showed similar performance to the Copperless DIBO-Alexa Fluor CLICK-iT® reaction. The original alkyne CLICK-IT® reaction is less desirable for both live cell and fixed cell labeling reactions.

The embodiments shown and described in the specification are not limiting in any way. Therefore, various changes, modifications, or alterations to those embodiments may be made without departing from the spirit of the invention in the scope of the following claims. All references cited are expressly incorporated by reference herein in their entirety.

What is claimed is:
1. A compound of general formula III

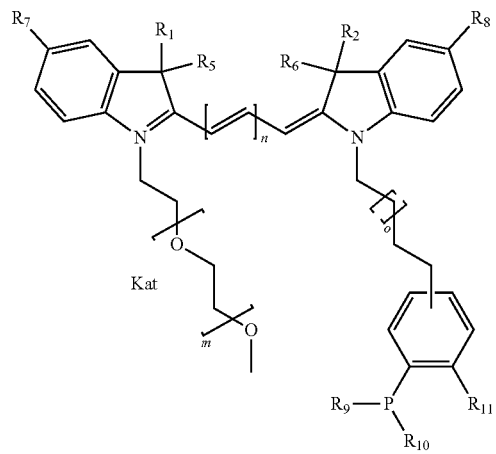

where
each of $R^1$, $R^2$, $R^5$, and $R^6$ is the same or different and is independently selected from the group consisting of an aliphatic, heteroaliphatic, sulfoalkyl group, or heteroaliphatic with terminal $SO_3$;
each of $R^7$ and $R^8$ is the same or different and is independently selected from either H, $SO_3$, sulfoalkyl, heteroaliphatic, or heteroaliphatic with terminal $SO_3$;
each of R9 and R10 is the same or different and is independently selected from either aryl groups, substituted aryl groups, or cycloalkyl groups;

R11 is an electrophilic group selected from the group consisting of a carboxylic acid, an alkyl ester, an aryl ester, a substituted aryl ester, an aldehyde, and amide, an aryl amide, an alkyl halide, a thioester, a sulfonyl ester, and alkyl ketone, an aryl ketone, a substituted aryl ketone, a halosulfonyl, a nitrile, and a nitro;

L is a linking group selected from the group consisting of a divalent linear ($-(CH_2)_o-$, o=1 to 15), crossed, cyclic, and combinations thereof alkylene group which can be substituted by at least one atom selected from the group consisting of oxygen, substituted nitrogen, and sulfur;

Kat is a number of $Na^+$, $K^+$, $Ca^{2+}$, ammonia, or other cation(s) needed to compensate the negative charge brought by the cyanine;

m is an integer from 0 to 5 inclusive; o is an integer from 0 to 12 inclusive; and n is an integer from 1 to 3 inclusive.

2. A compound of general formula IV

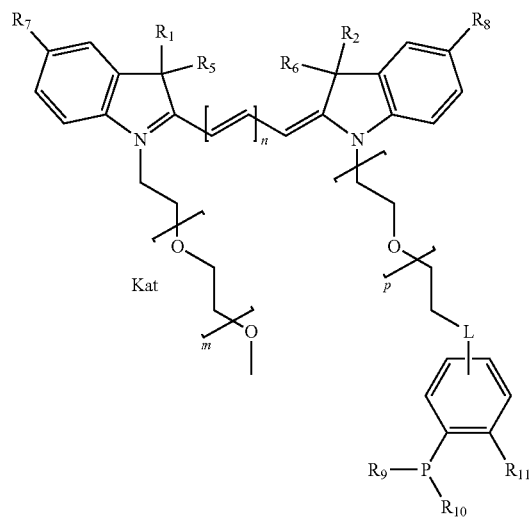

where
each of $R^1$, $R^2$, $R^5$, and $R^6$ is the same or different and is independently selected from the group consisting of an aliphatic, heteroaliphatic, sulfoalkyl group, or heteroaliphatic with terminal $SO_3$;

each of $R^7$ and $R^8$ is the same or different and is independently selected from either H, $SO_3$, sulfoalkyl, heteroaliphatic, or heteroaliphatic with terminal $SO_3$;

each of R9 and R10 is the same or different and is independently selected from either aryl groups, substituted aryl groups, or cycloalkyl groups;

R11 is an electrophilic group selected from the group consisting of a carboxylic acid, an alkyl ester, an aryl ester, a substituted aryl ester, an aldehyde, and amide, an aryl amide, an alkyl halide, a thioester, a sulfonyl ester, and alkyl ketone, an aryl ketone, a substituted aryl ketone, a halosulfonyl, a nitrile, and a nitro;

L is a linking group selected from the group consisting of a divalent linear ($-(CH_2)_o-$, o=1 to 15), crossed, cyclic, and combinations thereof alkylene group which can be substituted by at least one atom selected from the group consisting of oxygen, substituted nitrogen, and sulfur;

Kat is a number of $Na^+$, $K^+$, $Ca^{2+}$, ammonia, or other cation(s) needed to compensate the negative charge brought by the cyanine;

m is an integer from 0 to 5 inclusive; p is an integer from 1 to 6 inclusive; and n is an integer from 1 to 3 inclusive.

3. A compound of formula

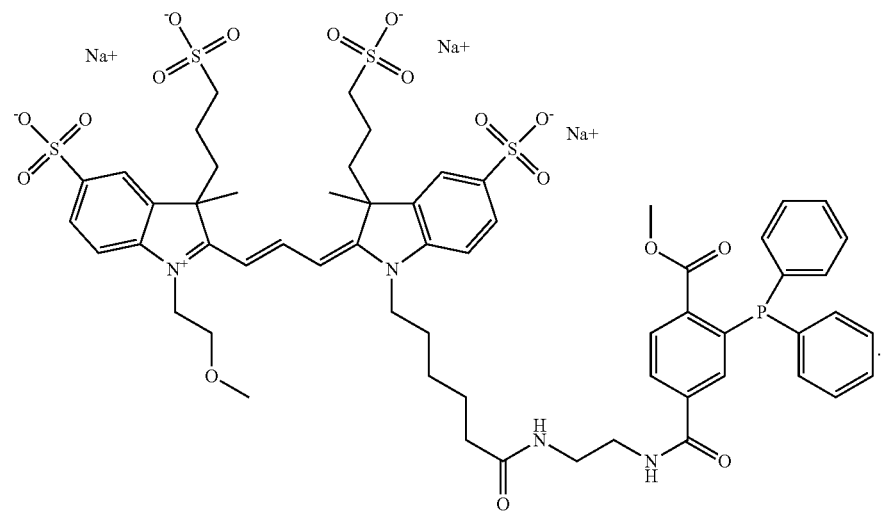

4. A compound of formula

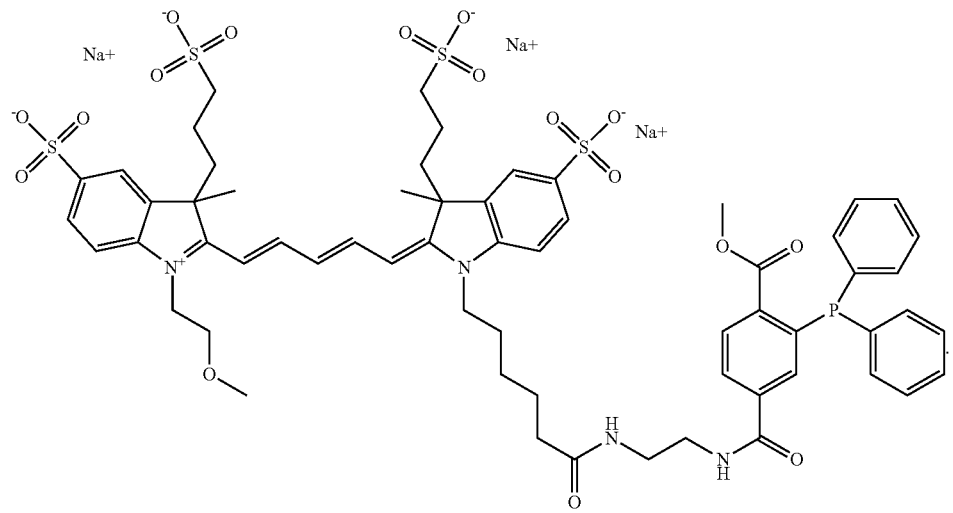

5. A compound of formula

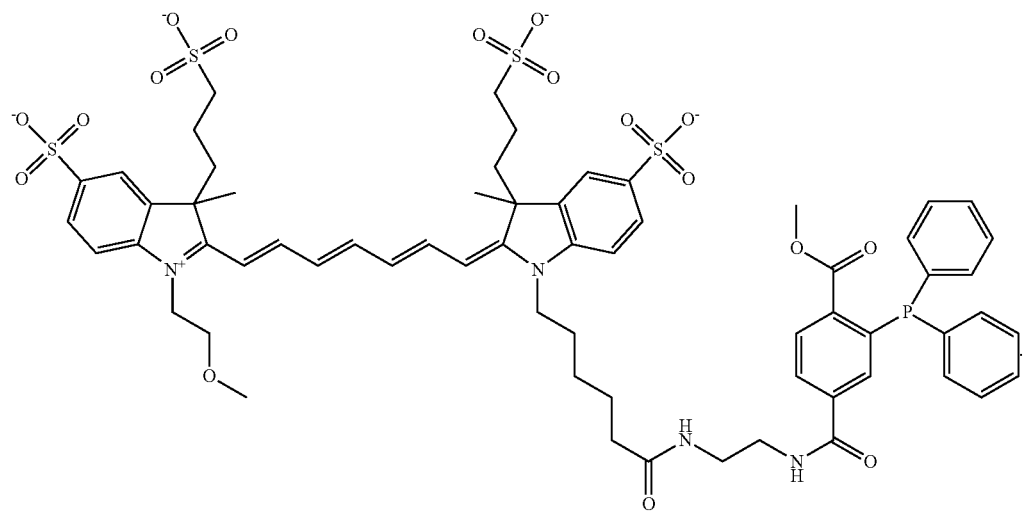

6. A method using the compound of claim 1 in a chemoselective ligation reaction with an azido compound.

7. A method using the compound of claim 2 in a chemoselective ligation reaction with an azido compound.

8. A method using the compound of claim 3 in a chemoselective ligation reaction with an azido compound.

9. A method using the compound of claim 4 in a chemoselective ligation reaction with an azido compound.

10. A method using the compound of claim 5 in a chemoselective ligation reaction with an azido compound.

11. A method of labeling at least one biomolecule, the method comprising providing a composition comprising at least one excipient and the compound of claim 1 in an effective concentration to the biomolecule under conditions sufficient for specifically binding the compound to the biomolecule, in the absence of non-specific binding, resulting in labeling of the biomolecule.

12. A method of labeling at least one biomolecule, the method comprising providing a composition comprising at least one excipient and the compound of claim 2 in an effective concentration to the biomolecule under conditions sufficient for specifically binding the compound to the biomolecule, in the absence of non-specific binding, resulting in labeling of the biomolecule.

13. The method of claim 11 further comprising reacting a linking moiety with the at least one biomolecule to result in an at least one biomolecule-linking moiety conjugate, and reacting the compound with the at least one biomolecule-linking moiety conjugate to result in an at least one biomolecule-linking moiety-compound conjugate.

14. The method of claim 12 further comprising reacting a linking moiety with the at least one biomolecule to result in an at least one biomolecule-linking moiety conjugate, and reacting the compound with the at least one biomolecule-linking moiety conjugate to result in an at least one biomolecule-linking moiety-compound conjugate.

15. The method of claim 13 where the linking moiety is a heterobifunctional linking moiety having a first terminal group reactive with an amine group and a second terminal azide.

16. The method of claim 14 where the linking moiety comprises a polyethylene glycol (PEG) group between the first and the second functional termini.

17. A method of detecting at least one biomolecule, the method comprising providing a composition comprising at least one excipient and the compound of claim 1 in an effective concentration to at least one biomolecule under conditions sufficient for binding the compound to the biomolecule, and detecting the biomolecule-bound compound.

18. A method of detecting at least one biomolecule, the method comprising providing a composition comprising at least one excipient and the compound of claim 2 in an effective concentration to at least one biomolecule under conditions sufficient for binding the compound to the biomolecule, and detecting the biomolecule-bound compound.

19. A kit comprising a compound of claim 1 and instructions for performing a chemoselective ligation reaction using the compound with an azido compound.

20. A kit comprising a compound of claim 2 and instructions for performing a chemoselective ligation reaction using the compound with an azido compound.

* * * * *